United States Patent [19]

Kelly et al.

[11] Patent Number: 5,739,350
[45] Date of Patent: Apr. 14, 1998

[54] CC-1065 ANALOGS

[75] Inventors: Robert C. Kelly, Augusta; Mark A. Mitchell; Paul A. Aristoff, both of Kalamazoo, all of Mich.

[73] Assignee: Pharmacia & Upjohn Company, Kalamazoo, Mich.

[21] Appl. No.: 479,231

[22] Filed: Jun. 7, 1995

Related U.S. Application Data

[63] Continuation of Ser. No. 279,767, Jul. 25, 1994, abandoned, which is a continuation of Ser. No. 966,139, Oct. 23, 1992, abandoned, which is a continuation of PCT/US91/02704, Apr. 24, 1996 which is a continuation of Ser. No. 513,501, Apr. 25, 1990, abandoned.

[51] Int. Cl.$^6$ .................................................. C07D 487/08
[52] U.S. Cl. .................... 548/421; 548/433; 548/300; 548/237; 548/181; 544/355; 544/405; 546/168; 546/271
[58] Field of Search .......................... 548/421; 530/300, 530/323

[56] References Cited

U.S. PATENT DOCUMENTS

| | | | |
|---|---|---|---|
| 4,169,888 | 10/1979 | Hanka et al. | 424/121 |
| 4,741,900 | 5/1988 | Alvarez et al. | 424/85 |
| 4,912,227 | 3/1990 | Kelley et al. | 548/421 |

FOREIGN PATENT DOCUMENTS

| | | |
|---|---|---|
| 088 695 | 9/1983 | European Pat. Off. . |
| 154 445 | 9/1985 | European Pat. Off. . |
| 173 629 | 3/1986 | European Pat. Off. . |
| 175 617 | 3/1986 | European Pat. Off. . |
| 247 792 | 12/1987 | European Pat. Off. . |
| 302 473 | 2/1989 | European Pat. Off. . |
| WO/04659 | of 1988 | WIPO . |
| WO 88/04659 | 6/1988 | WIPO . |

OTHER PUBLICATIONS

D.G. Martin et al., Journal of Antibiotics, 38, 746–752 (1985).
W. Wierenga, J. Am. Chem. Soc., 103, No. 18, 5621–5623 (1981).
P.D. Senter et al., Proc. Natl. Acad. Sci. USA, vol. 85, 4842–46, Jul. 1988 (Immunology).

Warpehoski, M.A. et al., Stereoelectronic Factors Influencing the Biological Activity and DNA Interaction of Synthetic Antitumor Agents Modeled on CC-1065, J. Med. Chem. 31:590–603 (1988).

Primary Examiner—Mukund J. Shah
Assistant Examiner—Pavanaram K. Sripada
Attorney, Agent, or Firm—William G. Jameson

[57] ABSTRACT

This invention provides some new synthetically obtained compounds of formula I and II

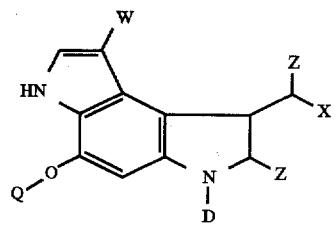

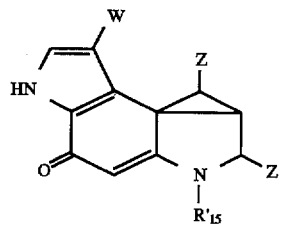

which are useful as chemical intermediates. Representative formula I or II compounds have also been shown to possess useful ranges of antitumor activity in standard laboratory animal tests.

In addition, the compounds of formula I or II can be linked to monoclonal antibodies, either directly or via known linking group, as a means of selectively delivering the CC-1065 analogs (Compounds of Formula I and II) to those target cells expressing the target antigen and thus selectively eliminating those diseased cells from the animal or human. Further, the compounds of formula I and II can be linked to soluble human CD4 or a soluble human CD4 protein fragment capable of binding to the gp120 envelope protein of the human immuno-virus and thus eliminate virally infected cells.

23 Claims, No Drawings the tether $-C(O)-(-R_{11}-)-C(O)-X_7-(-CH_2CH_2-X_7)n4-C(O)(-R_{11}-)-C(O)-$ where

CC-1065 ANALOGS

This is a continuation of U.S. Ser. No. 08/279,767 filed 25 Jul. 1994 now abandoned; which is a continuation of U.S. Ser. No. 07/966,139, filed 23 Oct. 1992, abandoned; which is a continuation of Ser. No. PCT/US91/02704, filed 24 Apr. 1991; which is a continuation of U.S. Ser. No. 07/513,501, filed 25 Apr. 1990, abandoned.

BACKGROUND OF THE INVENTION

Antibiotic CC-1065, (7bR,8aS)-7-[[1,6-dihydro-4-hydroxy-5-methoxy-7-[(4,5,8,8a -tetrahydro-7-methyl-4-oxocyclopropa[c]pyrrolo[3,2-e]indol-2(1H)-yl)carbonyl]benzo[1,2-b:4,3-b']dipyrrole-3(2H)-yl]carbonyl]1,6-dihydro-4-hydroxy-5-methoxy-benzo[1,2-b:4,3-b'] dipyrrole-3(2H)-carboxamide, is disclosed and claimed in L. J. Hanka et al U.S. Pat. No. 4,169,888 together with a process for preparing antibiotic CC-1065 by aerobic fermentation procedures, and recovering antibiotic CC-1065 therefrom.

In The Journal of Antibiotics, 1985, 38, 746, D. G. Martin et al reported that acetic acid adds across the spirocyclopropylcyclohexadienyl (SCPCH) system of CC-1065 to produce the phenolic, acetic acid product (AAP), 7-[[7-[[1-[(acetyloxy)methyl]-1,6-dihydro-5-hydroxy-8-methylbenzo[1,2-b:4,3-b']dipyrrol-3(2H)-yl]carbonyl]-1,6-dihydro-4-hydroxy-5-methoxybenzo[1,2-b:4,3-b']-dipyrrol-3(2H)-yl]carbonyl]-1,6-dihydro-4-hydroxy-5-methoxybenzo[1,2-b:4,3-b']dipyrrole-3(2H)-carboxamide. AAP was tested in vitro and in vivo and found to be less potent than CC-1065 by a factor of $10^3$ to $10^4$ depending upon the particular test system and therefore tended to divert attention from adducts of the SCPCH system as useful antitumor agents or as prodrugs to CC-1065 analogs.

In J. Am. Chem. Soc., 103, No. 18, 1981, W. Wierenga published a "Synthesis of the Left-Hand Segment of the Antitumor Agent CC-1065".

EP Application 0 154 445 (published Nov. 9, 1985) discloses various analogs of antibiotic CC-1065, including compounds of formula EP-I and EP-II (see General Formula chart of EP 0154 445), wherein $R_1$ in formula EP-II is $CH_3-$, $-CH_2Ph$, $CH=CHCH_2-$, $-CH_2SCH_3$, $-CH_2OCH_3$, $-CH_2OCH_2CH_2OCH_3$, $-CH_2CCl_3$, $-CH_2CH_2Si(R_2)_3$ or H, where Ph is phenyl; R is alkyl ($C_1$-$C_5$), phenyl, or H; $R_2'$ is $C_1$ to $C_5$-alkyl, phenyl or hydrogen, and is not necessarily the same as R in one compound; $R_3$ is alkyl($C_1$-$C_5$), phenyl, or H; and X is Cl, Br, or I—, or $OSO_2R_4O$, where $R_{40}$ is $C_1$ to $C_5$-alkyl, phenyl, tolyl, bromophenyl, nitrophenyl, or trifluromethyl. (See also U.S. Pat. No. 4,912,227.) The O-protected compounds of formula EP-II are chemically stable and only removable under specific chemical conditions. However, when the compounds of formula EP-II are O-deprotected, they can be cyclized to yield the compounds of EP-I. Other analogs of antibiotic CC-1065 are disclosed in EP Application 340-243A (published Aug. 11, 1989).

EP Application 0 154 445 also discloses CPI dimers joined by $-CO-(CH_2)n_1-CO-$ where $n_1$ is 2–12 and CPI dimers joined by the tether $-C(O)-(-R_{11}-)-C(O)-X_7-(-CH_2CH_2-X_7)n4-C(O)-(-R_{11}-)-C(O)-$ where $R_{11}=CH_2CH_2$, $CH=CH$; and $X_7=O$, NH, and n4=1–4, and the HCl and MeI salts for $X_7=NH$.

Additional dimers of CPI prodrugs joined by $-CO-(CH_2)n_1-CO-$ where n is 2–12 and CPI dimers joined by $R_{11}=CH_2CH_2$, $CH=CH$; and $X_7=O$, NH, and n4=1–4, and the HCl and MeI salts for $X_7=NH$ are disclosed in U.S. patent application Ser. No. 944,633, filed 19 Dec. 1986, now abandoned, and PCT/US Application 87/03227, filed 11 Dec. 1987, published 14 Jul. 1988.

Various oral and poster presentations of material in U.S. patent application Ser. No. 944,633, filed 19 Dec. 1986 and EP Application 340 243A, published Aug. 11, 1989, have been made.

Various oral and poster presentations of the CC-1065 analogs having two CPI subunits disclosed in U.S. patent application Ser. No. 07/243,350, filed 12 Sep. 1988 (now abandoned) and EP Application PCT/US89/03329, filed 7 Aug. 1989 (Case 4305.P).

The use of tumor-associated monoclonal antibody (Mab) -conjugates and Mab-toxin conjugates for the treatment of cancer is described in many publications. For example, European Patent Application 87304516.5 (Publication No. 70 247 792) discloses immunoglobulin conjugates formed by reaction of an antineoplastic indole-dihydroindole vinca alkaloid containing a hydrazide group with an oxidized glycoprotein containing aldehyde groups. Other European Patent Applications disclosing antibody conjugates include EP 83400461.6 (Publication No. 0 088 695), 85401695.3 (Publication No. 0 173 629, see also U.S. Pat. No. 4,741,900) and 85401776.1 Publication No. 0 175 617).

SUMMARY OF THE INVENTION

This invention provides some new synthetically obtained compounds of formula I and II (see General Formulae Chart), as defined hereinafter, which am useful as chemical intermediates. Representative formula I and II compounds have also been shown to possess useful ranges of antitumor activity in standard laboratory animal tests. The compounds of this invention are obtained by chemical processes shown in Schemes 1–15 and detailed in the examples.

In addition, the compounds of formula I or II can be linked to monoclonal antibodies, either directly or via known linking group, as a means of selectively delivering the CC-1065 analogs (Compounds of Formula I and II) to those target cells expressing the target antigen and thus selectively eliminating those diseased cells from the animal or human. Further, the compounds of formula I and II can be linked to soluble human CD4 or a soluble human CD4 protein fragment capable of binding to the gp120 envelope protein of the human immuno-virus and thus eliminate virally infected cells.

DETAILED DESCRIPTION OF THE INVENTION

More specifically, this invention provides new chemical compounds of Formula I or II (see FORMULAE sheet)

wherein W is selected from $C_1$-$C_5$ alkyl, phenyl or hydrogen;

wherein X is selected from azido, a halogen atom, cyanate, thiocyanate, isocyanate, thioisocyanate, phosphate diester (O—PO(OR)$_2$), phosphonyl (—O—PO$_2$R), thiophosphonyl (—O—PSOR), sulfinyl (—O—SOR) or sulfonyl (—O—SO$_2$R);

wherein D is $R_{15}$ or $R'_{15}$;

wherein Q is Y when D is $R'_{15}$;

wherein Q is Y' when D is $R_{15}$;

wherein Y is selected from hydrogen, —C(O)R, —C(S)R, —C(O)OR$_1$, —S(O)$_2$R$_1$, —C(O)NR$_2$R$_3$, —C(S)

$NR_2R_3$, —$C(O)NHSO_2R_4$, —$C(O)CH_2(OCH_2CH_2)_{n7}$ $O(C_1-C_3\text{ alkyl})$ and n7 is 0–5 (preferably 2 or 3), or —$C(O)(CH_2)_{n8}C(O)R_b$, where n8 is 0–10 (preferably 2, 3 or 4) and $R_b$ is selected from —OH (or a metal or amine salt thereof), —$OR_c$ where $R_c$ is —$CH_2C(CH_2OH)_3$ or $R_{70}$, and —$N(R_d)R_e$ where $R_d$ is hydrogen or $C_1-C_4$ alkyl, and $R_e$ is selected from —$C(CH_2OH)_3$, —$CH_2C(CH_2OH)_3$, —$CH_2C(CH_2NH_2)_3$, $R_{70}$, $R_{71}$ or $R_{72}$ where n9 is 1 or 2 and n10 is 1–3;

wherein Y' is selected from —$C(O)R_{10}$, —$C(S)R_{10}$, —$C(O)OR_{10}$, —$S(O)_2R_{10}$, —$C(O)NR_{12}R_{13}$, —$C(S)NR_{12}R_{13}$, or —$C(O)NHSO_2R_{14}$;

wherein Z is selected from the group consisting of $C_1-C_5$ alkyl, phenyl or hydrogen;

wherein R is selected from the group consisting of $C_1-C_{20}$ alkyl; $C_2-C_6$ alkenyl; $C_2-C_6$ alkynyl; phenyl optionally substituted with one, 2 or 3 $C_1-C_4$ alkyl, $C_1-C_3$ alkoxy, halo, $C_1-C_3$ alkylthio, trifluoromethyl, $C_2-C_6$ dialkylamino, or nitro; naphthyl optionally substituted with one or 2 $C_1-C_4$ alkyl, $C_1-C_3$ alkoxy, halo, trifluoromethyl, $C_2-C_6$ dialkylamino, $C_1-C_3$ alkylthio or nitro;

wherein $R_1$ is selected from $C_1-C_{20}$ alkyl or phenyl optionally substituted with one, 2 or 3 $C_1-C_4$ alkyl, $C_1-C_3$ alkoxy, halo, $C_1-C_3$ alkylthio, trifluoromethyl, $C_2-C_6$ dialkylamino, or nitro;

wherein $R_2$ and $R_3$, being the same or different, are selected from hydrogen, $C_1-C_{20}$ alkyl, or phenyl optionally substituted with one, 2 or 3 $C_1-C_4$ alkyl, $C_1-C_3$ alkoxy, halo, $C_1-C_3$ alkylthio, trifluoromethyl, $C_2-C_6$ dialkylamino, or nitro; with the proviso that both $R_2$ and $R_3$ can not be phenyl or substituted phenyl;

wherein $R_4$ is selected from $C_1-C_{10}$ alkyl; phenyl optionally substituted with one, 2 or 3 $C_1-C_4$ alkyl, $C_1-C_3$ alkoxy, halo, $C_1-C_3$ alkylthio, trifluoromethyl, $C_2-C_6$ dialkylamino, or nitro; naphthyl optionally substituted with one or 2 $C_1-C_4$ alkyl, $C_1-C_3$ alkoxy, halo, trifluoromethyl, $C_2-C_6$ dialkylamino, $C_1-C_3$ alkylthio or nitro;

wherein $R_{10}$, $R_{13}$ and $R_{14}$, being the same or different, are selected from —$(C_1-C_{20}\text{ alkyl})(CH_2)_nR_{50}$ or -(phenyl optionally substituted with one or two $C_1-C_4$ alkyl, $C_1-C_3$ alkoxy, halo, $C_1-C_3$ alkylthio, trifluoromethyl, $C_2-C_6$ dialkylamino, or nitro)$(CH_2)_nR_{50}$;

wherein n is 0–10;

wherein $R_{50}$ is selected from the group consisting of
(i) —$CO_2H$;
(ii) —$CH_2NH_2$;
(iii) —SH;
(iv) —$C(R_{60})(R_{61})$—SH wherein $R_{60}$ and $R_{61}$, being the same or different, are $C_1-C_4$ alkyl or H;
(v) —$NHC(O)$—$(CH_2)_{n_1}$—$C(R_{60})(R_{61})$—SH wherein $R_{60}$ and $R_{61}$ are defined above and $n_1$ is 0–5;
(vi) —$C(O)NHNH_2$ (hydrazido);
(vii) —$NHNH_2$ (hydrazino);
(viii) —$CH_2OH$ (hydroxymethyl);
(ix) —$NHC(S)NH_2$ (thioureido);
(x) —$CH_2NHC(O)NH_2$;
(xi) —$NHC(S)NHNH_2$;
(xii) —$C(O)CH_2X_1$ ($X_1$ is a halogen);
(xiii) —$CH_2X_1$ (halomethyl) wherein $X_1$ is a halogen;
(xiv) —CHO (aldehyde);

(xv)
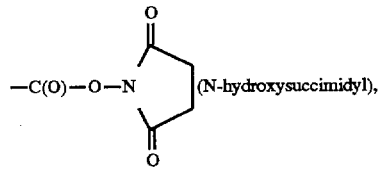

(xvi)
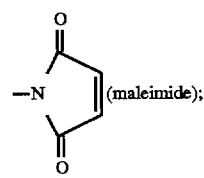

(xvii) —$C(R_{60})(R_{61})C(O)NHNH_2$ wherein $R_{60}$ and $R_{61}$, being the same or different, are $C_1-C_4$ alkyl or H;
(xviii) —$O(CH_2)_{n_1}C(R_{60})(R_{61})C(O)NHNH_2$ wherein $R_{60}$, $R_{61}$, and $n_1$ are defined above;
(xix) —$N(R_{62})(CH_2)_{n_1}C(R_{60})(R_{61})C(O)NHNH_2$ wherein $R_{60}$, $R_{61}$ and $R_{62}$ are independently selected from $C_1-C_4$ alkyl or H and $n_1=0–5$;
(xx) —$O(CH_2)_{n_2}C(R_{60})(R_{61})C(O)NHNH_2$ ($n_2=1–5$);
(xxi) —$NHR_{51}$;
(xxii) —$C(O)NHNHR_{51}$;
(xxiii) —$NHNHR_{51}$;

wherein $R_{51}$ is an amine protecting group such as BOC (t-butoxycarbonyl), FMOC (9-fluorenylmethyloxycarbonyl, TFA (trifluoroacetate) amide), ALLOC (alloxycarbonyl), CBZ (benzoxycarbonyl), or TROC (trichloroethoxycarbonyl);

(xxiv) —$NHC(=NH)NH_2$ (guanadinyl); or
(xxv) —B—M—$(CH_2)n_3R_{52}$ wherein $n_3=0–5$; $R_{52}$ is the same as $R_{50}$ above (groups (i)–(xxiv) only);

wherein B is an ester [—OC(O)— or —C(O)O—] or amide [—NHC(O)— or —C(O)NH—] bond;

wherein M is defined below as any compatible peptide, carbohydrate, or other organic moiety imparting to the embodiment of this invention specific properties (e.g. chemical, photochemical, or enzymatic cleavability; branching for multiple site attachment of additional therapeutic agents of the invention; optimal spacing between therapeutic agent and antibody); for cleavage of linkers by serum compliment M can be chosen from Table III;

wherein in Table III (a.a) represents any naturally occurring amino acid (and can be the same or different) and $n_4=0–5$;

wherein $R_{12}$ is selected from hydrogen, $C_1-C_{20}$ alkyl, or phenyl optionally substituted with one, 2 or 3 $C_1-C_4$ alkyl, $C_1-C_3$ alkoxy, halo, $C_1-C_3$ alkylthio, trifluoromethyl, $C_2-C_6$ dialkylamino, or nitro;

wherein $R_{15}$ is a carbonylaryl group selected from the group consisting of
Formula (a) wherein $X_8$ is —O—, —S—, —NH—; $X_9$ is —CH— or N; $X_{10}$ is —O—, —S—, —NH—; $X_{11}$ is —CH— or —N—; $X_5$ may be the same or different and is H, $OCH_3$, $NO_2$, $NHC(O)CH_3$, OH, halo, $C_1-C_4$ alkyl, $C_1-C_3$ alkoxy, $C_2-C_6$ dialkylamino, or $NHC(O)C_6H_5$; and $X_6$ is H, $OCH_3$, NO$_2$, NHC(O)CH$_3$, OH, halo, C$_1$-C$_4$ alkyl, C$_1$-C$_3$ alkoxy, C$_2$-C$_6$ dialkylamino, or NHC(O)C$_6$H$_5$;

Formula (b) wherein X$_5$, X$_8$, X$_9$ have the meanings defined above;

Formula (c) wherein X$_5$, X$_6$, X$_8$, X$_9$ have the meanings defined above;

wherein R'$_{15}$ is a carbonylaryl group selected from the group consisting of

Formula (d) wherein X$_8$ is —O—, —S—, —NH—; X$_9$ is —CH— or N; X$_{10}$ is —O—, —S—, —NH—; X$_{11}$ is —CH— or —N—; X$_5$ can be the same or different and is H, OCH$_3$, NO$_2$, NHC(O)CH$_3$, OH, halo, C$_1$-C$_4$ alkyl, C$_1$-C$_3$ alkoxy, C$_2$-C$_6$ dialkylamino, or NHC(O)C$_6$H$_5$; X$_6$ is H, OCH$_3$, NO$_2$, NHC(O)CH$_3$, OH, halo, C$_1$-C$_4$ alkyl, C$_1$-C$_3$ alkoxy, C$_2$-C$_6$ dialkylamino, or NHC(O)C$_6$H$_5$; n and R$_{50}$ have the meanings defined above;

Formula (e) wherein X$_8$ is —O—, —S—, —NH—; X$_9$ is —CH— or N; X$_{10}$ is —O—, —S—, —NH—; X$_{11}$ is —CH— or —N—; X$_5$ is H, OCH$_3$, NO$_2$, NHC(O)CH$_3$, OH, halo, C$_1$-C$_4$ alkyl, C$_1$-C$_3$ alkoxy, C$_2$-C$_6$ dialkylamino, or NHC(O)C$_6$H$_5$; X$_6$ is H, OCH$_3$, NO$_2$,NHC(O)CH$_3$, OH, halo, C$_1$-C$_4$ alkyl, C$_1$-C$_3$ alkoxy, C$_2$-C$_6$ dialkylamino, or NHC(O)C$_6$H$_5$; n and R$_{50}$ have the meanings defined above;

Formula (f) wherein X$_5$, X$_8$, X$_9$, n and R$_{50}$ have the meanings defined above;

Formula (g) wherein X$_5$, X$_6$, X$_8$, X$_9$, n and R$_{50}$ have the meanings defined above; and Formula (h) wherein X$_5$, X$_6$, X$_8$, X$_9$, n and R$_{50}$ have the meanings defined above. (Formulae a–h are set forth in the General Formulae Sheets).

W is preferably methyl.

X is preferably halogen, more preferably chloro or bromo.

Z is preferably hydrogen.

R$_{15}$ is preferably Formula aa (General Formulae Sheet), wherein X$_5$ and X$_6$ are hydrogen and X$_{10}$ is —O— or —NH—; or any of the foregoing optionally substituted with X$_5$ and/or X$_6$, independently selected from NO$_2$, halogen, OH, C$_1$-C$_3$ alkoxy or C$_2$-C$_6$ dialkylamino.

R'$_{15}$ is preferably Formula dd, ddd, or dddd (General Formulae Sheet), wherein X$_5$ and X$_6$ are hydrogen, or any of the foregoing optionally substituted with X$_5$ and/or X$_6$, independently selected from NO$_2$, NHX(O)CCH$_3$, halogen, C$_1$-C$_4$ alkyl, C$_1$-C$_3$ alkoxy or C$_2$-C$_6$ dialkylamino.

—(CH$_2$)$_m$R$_{50}$ is preferably —(CH$_2$)$_{n1}$—C(R$_{60}$)(R$_{61}$)C(O)NHNH$_2$; —NHC(O)—(CH$_2$)$_{n2}$—C(R$_{60}$)(R$_{61}$)SH; or —(CH$_2$)$_{m2}$C(R$_{60}$)(R$_{61}$)SH, wherein R$_{60}$ and R$_{61}$ are independently methyl or H, m is 1–3, and m$_2$ is 0–3.

Q is preferably Y.

Y is preferably hydrogen, 3,6,9-trioxadecanoyl, N-[2-hydroxy-1,1-bis(hydroxymethyl)ethyl]glutaramyl, 7-glutaramyl-naphthalene-1,3-disulfonic acid salts, —C(O)R, —C(O)OR$_1$, —SO$_2$R$_1$ or —C(O)NR$_2$R$_3$ wherein R, R$_1$ and R$_2$ is phenyl optionally substituted with one, two or three halogen, NO$_2$, C$_1$-C$_4$ alkyl, C$_1$-C$_3$ alkoxy, C$_1$-C$_3$ thioalkyl, trifluoromethyl or C$_2$-C$_6$ dialkylamino.

X$_6$ is preferably hydrogen, NO$_2$, halo (most preferably chloro), methyl, ethyl, methoxy, ethoxy, dimethylamino, diethylamino, dipropylamino or dibutylamino.

X$_9$ is preferably —CH—.

X$_8$ is preferably —NH—.

X$_{11}$ is preferably —CH—.

X$_{10}$ is preferably —NH— or —O—.

Halogen atom (halo) refers to a bromo, chloro, iodo or fluoro atom.

Examples of C$_1$-C$_{20}$ alkyl are methyl, ethyl, propyl, butyl and the like, including isomeric forms thereof. Examples of C$_1$-C$_3$ alkoxy are methoxy, ethoxy, propoxy and isomeric forms thereof. Examples of C$_2$-C$_6$ dialkylamino are dimethylamino, diethylamino, methylethylamino, dipropylamino and ethylpropylamino.

The compounds of formula I and II on the FORMULAE sheet can be named as derivatives of the numbering system (B$_1$ and B$_2$) shown on the FORMULAE sheet. Such compounds will contain the 1,2,3,6-tetrahydro-3-R$_5$-8-W-5-Y-benzo[1,2-b:4,3-b']dipyrrol-1-[Z—CH(X)]-structure.

The compounds of Formula I and II are drawn as the racemic mixture and include the natural isomer of Formula Ia and IIa, which can be resolved from the racemic mixture and/or prepared from starting materials or intermediates of the natural, i.e. 1(S)-configuration.

Examples of compounds of Formula I and II of this invention include:

(S)-2-[[[2-[[1-(chloromethyl)-1,6-dihydro-5-hydroxy-8-methylbenzo[1,2-b:4, 3-b'][dipyrrol-3(2H)-yl]carbonyl] 1H-indol-5-yl]amino]-carbonyl]-2-benzofuran-5-carboxylic acid phenylmethyl ester (Cpd #1);

(S)-2-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-2-benzofuran-5-carboxylic acid (Cpd #2);

(S)-2-[[[2-[(4,5,8,8a-tetrahydro-7-methyl-4-oxocyclopropa-[c]pyrrol[3,2-e]indol-2(1H)-yl)-carbonyl]-1H-indol-5-yl]amino]carbonyl]-2-benzofuran-5-carboxylic acid (Cpd #3);

(S)-2-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-1H-indol-5-yl]-carbamic acid, 1,1-dimethylethyl ester (Cpd #4);

(S)—N-[2-[[1-(chloromethyl)-1,6-dihydro-8-methyl-5-[[[[4-[[[(1,1-dimethylethyl)oxy]-carbonyl]aminomethyl]phenyl]amino]car-bonyl]oxy]benzo[1,2-b:4,3-b']-dipyrrol-3(2H)-yl]carbonyl]-1H-indol-5-yl]-2-benzofurancarboxamide (Cpd #5);

5-[(2-mercaptopropionyl)amino]-N-[2-(4,5,8,8a-tetrahydro-7-methyl-4-oxocyclopropa-[c]pyrrolo[3,2-e]indol-2(1H)-yl)-1H-indol-5-yl]-1H-indole-2-carboxamide (Cpd #8);

(S)-N-[2-[[1-(chloromethyl)-1,6-dihydro-8-methyl-5-[[[[4-[[(phenylmethyl)oxy]carbonyl]phenyl]amino]carbonyl]oxy]benzo[1,2-b: 4,3-b']dipyrrol-3(2H)-2-yl]carbonyl]1H-indol-5-yl]-2-benzofurancarboxamide (Cpd #10);

(S)-2-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[[2-[[(1,1-dimethylethyl)-oxy]carbonyl]hydrazino]carbonyl]-1H-indol (Cpd #11A);

(S)-2-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-(hydrazinocarbonyl)-1H-indol monohydrochloride (Cpd #11B);

(S)-N-[2-[[1-(chloromethyl)-1,6-dihydro-8-methyl-5-[[[[4-[[2-[[(1,1-dimethylethyl)-oxy]carbonyl]hydrazino]carbonyl]phenyl]amino]carbonyl]oxy]benzo[1,2-b:4,3-b']dipyrrol-3(2H)-yl]carbonyl]-1H-indol-5-yl]-2-benzofurancarboxamide (Cpd #12);

(S)-N-[2-[[1-(chloromethyl)-1,6-dihydro-8-methyl-5-[[[[4-[[2-[[(1,1-dimethylethyl-)oxy]carbonyl]hydrazino]carbonyl]ethyl]phenyl]amino]carbonyl]oxy]benzo[1,2-b:4,3-b']dipyrrol-3(2H)-yl]carbonyl]-1H-indol-5-yl]-2-benzofurancarboxamide (Cpd #13);

(S)-N-[2-[[1-(chloromethyl)-1,6-dihydro-8-methyl-5-[[[[4-[2-[(hydrazinocarbonyl)ethyl]phenyl]amino]carbonyl]oxy]benzo[1,2-b:4,3-b']dipyrrol-3(2H)-yl]carbonyl]-1H-indol-5-yl]-2-Benzofurancarboxamide, monohydrochloride (Cpd #14);

(S)-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-[[2-[[(1,1-dimethylethyl) oxy]carbonyl]hydrazino]carbonyl]ethyl]-2-Benzofuran (Cpd #15);

(S)-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl-5-[2-(hydrazinocarbonyl)ethyl]-2-benzfuran monohydrochloride (Cpd #16);

(7bR)-N-[2-[[4,5,8,8a-tetrahydro-7-methyl-4-oxocyclopropa[c]pyrrolo[3,2-e]indol-2(1H)-yl-carbonyl]-1H-indol-5-yl]aminocarbonyl]-5-[2-[[2-[[(1,1-dimethylethyl)oxy]carbonyl]hydrazino]carbonyl]ethyl-2-benzofuran (Cpd #17);

(S)-[[[-2[[1-(chloromethyl)-1,6-dihydro-5-hydroxy-8-methylbenzo[1,2-b:4,3-b']dipyrrol-3-(2H)-yl]carbonyl]-1H-indol-5-yl]amino]carbonyl]-5-[2-[[2-[[(1,1-dimethylethyl)oxy]carbonyl]hydrazino]carbonyl]ethyl-2-benzofuran 3,6,9-trioxadecanoic acid ester (Cpd #18);

(S)-[[[-2[[1-(chloromethyl)-1,6-dihydro-5-hydroxy-8-methylbenzo[1,2-b:4,3-b']dipyrrol-3-(2H)-yl]carbonyl]-1H-indol-5-yl]amino]carbonyl]-5-[2-(hydrazino)carbonyl]ethyl-2-benzofuran 3,6,9-trioxadecanoic acid ester (Cpd #19);

(S)-[[[-2[[1-(chloromethyl)-1,6-dihydro-5-hydroxy-8-methylbenzo[1,2-b:4,3-b']dipyrrol3-(2H)-yl]carbonyl]-1H-indol-5-yl]amino]carbonyl]-5-[2-[[2-[[(1,1-dimethylethyl) oxy]carbonyl]hydra-zino]carbonyl]ethyl]-2-benzofuran glutaric acid monoester (Cpd #20);

(S)-[[[-2[[1-(chloromethyl)-1,6-dihydro-5-hydroxy-8-methylbenzo[1,2-b:4,3-b']dipyrrol-3-(2H)-yl]carbonyl]-1H-indol-5-yl]amino]carbonyl]-5-[2-[[2-[[(1,1-dimethylethyl) oxy]carbonyl]hydra-zino]carbonyl]ethyl]-2-benzofuran ester of N-[2-hydroxy-1,1-bis(hydroxymethyl) ethyl]glutaramic acid (Cpd #21);

(S)-[[[-2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-(hydrazino)carbonyl]ethyl-2-benzofuran ester of N-[2-hydroxy-1,1-bis(hydroxymethyl)ethyl]glutaramic acid (Cpd #22);

(S)-[[[-2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-[[2-[[(1,1-dimethylethyl)oxy]carbonyl]hydra-zino]carbonyl]ethyl]-2-benzofuran glutaric acid monoester mono amide of 7-amino-naphthalene-1,3-disulfonic acid disodium salt (Cpd #23); and (S)-[[[-2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-(hydrazino)carbonyl]ethyl-2-benzofuran glutaric acid monoester mono amide of 7-amino-naphthalene 1,3-disulfonic acid disodium salt (Cpd #24).

An embodiment of the subject invention are compounds of Formula I, wherein W is methyl; Z is hydrogen; X is halogen (most preferably a chloro atom); and Q is Y' and Y' is selected from —C(O)$R_{10}$, —SO$_2$$R_{10}$, —C(O)NR$_{12}$R$_{13}$; $R_{10}$ and $R_{13}$ are selected from -(phenyl optionally substituted one or two $C_1$-$C_4$ alkyl, $C_1$-$C_3$ alkoxy, halo, $C_1$-$C_3$ alkylthio, trifluoromethyl, $C_2$-$C_6$ dialkylamino, or nitro)(CH$_2$)$_n$R$_{50}$ wherein n is zero, one or two, and R$_{50}$ is —CO$_2$H, —CH$_2$NH$_2$, —SH, —C(R$_{60}$)(R$_{61}$)SH, —NHC(O)—(CH$_2$)$_{n1}$C(R$_{60}$) (R$_{61}$)—SH, —C(O)NHNH$_2$, —CH$_2$OH, —C(R$_{60}$)(R$_{61}$)C(O)NHNH$_2$, —N(R$_{62}$)(CH$_2$)$_{n1}$C(R$_{60}$) (R$_{61}$)C(O)NHNH$_2$, —O(CH$_2$)$_{n2}$C(R$_{60}$)(R$_{61}$)C(O)NHNH$_2$; wherein $n_1$ is 1-3; $n_2$ is 0-2; $R_{60}$, $R_{61}$ and $R_{62}$, being the same or different, are H, methyl or ethyl; $R_{12}$ is hydrogen; and $R_{15}$ is (aa) (see General Formulae Chart) wherein $X_{10}$ is —NH— or —O—; $X_5$ and $X_6$, being the same or different are hydrogen, OCH$_3$, NO$_2$, NHC(O)CH$_3$, halo, $C_1$-$C_4$ alkyl, $C_1$-$C_3$ alkoxy or $C_2$-$C_6$ dialkylamino.

A preferred embodiment of the subject invention are compounds of Formula I, wherein W is methyl; Z is hydrogen; X is halogen (most preferably a chloro atom); and Q is Y' and Y' is selected from —C(O)$R_{10}$, —SO$_2$$R_{10}$, —C(O)NR$_{12}$R$_{13}$; $R_{10}$ and $R_{13}$ are selected from -(phenyl optionally substituted one or two $C_1$-$C_4$ alkyl, $C_1$-$C_3$ alkoxy, halo, $C_1$-$C_3$ alkylthio, trifluoromethyl, $C_2$-$C_6$ dialkylamino, or nitro)(CH$_2$)$_n$R$_{50}$ wherein n is zero, one or two, and R$_{50}$ is —CO$_2$H, —CH$_2$NH$_2$, —SH, —C(R$_{60}$)(R$_{61}$)SH, —NHC(O)—(CH$_2$)$_{n1}$—C(R$_{60}$) (R$_{61}$)—SH, —C(O)NHNH$_2$, —CH$_2$OH, —C(R$_{60}$)(R$_{61}$)C(O)NHNH$_2$, —N(R$_{62}$)(CH$_2$)$_{n1}$C(R$_{60}$) (R$_{61}$)C(O)—NHNH$_2$, —O(CH$_2$)n$_2$C(R$_{60}$)(R$_{61}$)C(O)NHNH$_2$; wherein $n_1$ is 1-3; $n_2$ is 0-2; $R_{60}$, $R_{61}$ and $R_{62}$, being the same or different, are H, methyl or ethyl; $R_{12}$ is hydrogen; and $R_{15}$ is (aa) (see General Formulae Chart) wherein $X_{10}$ is —NH— or —O—; $X_5$ and $X_6$ are hydrogen.

Another embodiment of the subject invention are compounds of Formula I, wherein W is methyl; Z is hydrogen; X is halogen (most preferably a chloro atom); and Q is Y' and Y' is selected from —C(O)$R_{10}$, —SO$_2$$R_{10}$, —C(O)NR$_{12}$R$_{13}$; $R_{10}$ and $R_{13}$ are selected from -(phenyl optionally substituted one or two $C_1$-$C_4$ alkyl, $C_1$-$C_3$ alkoxy, halo, $C_1$-$C_3$ alkylthio, trifluoromethyl, $C_2$-$C_6$ dialkylamino, or nitro)(CH$_2$)$_n$R$_{50}$ wherein n is zero, one or two, and R$_{50}$ is N-hydroxysuccimidyl or maleimide; $R_{12}$ is hydrogen; and $R_{15}$ is (aa) (see General Formulae Chart) wherein $X_{10}$ is —NH— or —O—; $X_5$ and $X_6$, being the same or different are hydrogen, OCH$_3$, NO$_2$, NHC(O)CH$_3$, halo, $C_1$-$C_4$ alkyl, $C_1$-$C_3$ alkoxy or $C_2$-$C_6$ dialkylamino.

Another embodiment of the subject invention are compounds of Formula I wherein W is methyl; Z is hydrogen; X is halogen; and Q is Y' and Y' is selected from —C(O)NR$_{12}$R$_{13}$, —C(O)R$_{10}$, —SO$_2$R$_{10}$, —C(O)NR$_{12}$R$_{13}$; $R_{12}$ is hydrogen, $R_{10}$ and $R_{13}$ are selected from -(phenyl optionally substituted with one or two $C_1$-$C_4$ alkyl, $C_1$-$C_3$ alkoxy, halo, $C_1$-$C_3$ alkylthio, trifluoromethyl, $C_2$-$C_6$ dialkylamino, or nitro)(CH$_2$)$_n$R$_{50}$; n is zero or one; R$_{50}$ is —B—M—(CH$_2$)n$_3$R$_{52}$ wherein R$_{52}$ is —NH$_2$, —C(O)NHNH$_2$, —CO$_2$H, or —SH; and R$_{15}$ is (aa) (see General Formulae Chart) wherein $X_{10}$ is —NH— or —O—; $X_5$ and $X_6$, being the same or different are hydrogen, OCH$_3$, NO$_2$, NHC(O)CH$_3$, halo, $C_1$-$C_4$ alkyl, $C_1$-$C_3$ alkoxy or $C_2$-$C_6$ dialkylamino.

Another embodiment of the subject invention are compounds of Formula I wherein W is methyl; Z is hydrogen; X is halogen (most preferably a chloro atom); and Q is Y and Y is selected from hydrogen, —C(O)R, —SO$_2$R$_1$, —C(O)NR$_2$R$_3$; R$_3$ is hydrogen, R and R$_1$ and R$_2$ (being the same or different) are selected from phenyl optionally substituted with one to three $C_1$-$C_4$ alkyl, $C_1$-$C_3$ alkoxy, halo, $C_1$-$C_3$, alkylthio, trifluoromethyl, $C_2$-$C_6$ dialkylamino, or nitro; and R'$_{15}$ is selected from (dd), (ddd), (dddd), (ee) or (eee) wherein n is 0–6; $X_{10}$ is —NH— or —O—; $X_5$ and $X_6$ are independently H, OH, NO$_2$, NHC(O)CH$_3$, halo, $C_1$-$C_4$ alkyl, $C_1$-$C_3$ alkoxy or $C_2$-$C_6$ dialkylamino; and R$_{50}$ is selected from either i) N-hydroxysuccinimidyl or maleimidyl; ii) —B—M—(CH$_2$)$_{n3}$R$_{52}$ wherein R$_{52}$ is —NH$_2$, —C(O)NHNH$_2$, —CO$_2$H, or —SH; or iii) —CO$_2$H, —CH$_2$NH$_2$, —SH, —C(R$_{60}$)(R$_{61}$)SH, —NHC(O)—(CH$_2$)$_{n1}$—C(R$_{60}$)(R$_{61}$)—SH, —C(O)NHNH$_2$, —CH$_2$OH, —C(R$_{60}$)(R$_{61}$)C(O)NHNH$_2$, —N(R$_{62}$)(CH$_2$)$_{n1}$C(R$_{60}$)(R$_{61}$)C(O)—NHNH$_2$, —O(CH$_2$)n$_2$C(R$_{60}$)(R$_{61}$)C(O)NHNH$_2$; wherein n$_1$ is 1–3; n$_2$ is 0–2; and R$_{60}$, R$_{61}$ and R$_{62}$, being the same or different, are H, methyl or ethyl.

Another preferred embodiment of the subject invention are compounds of Formula I wherein W is methyl; Z is hydrogen; X is halogen (most preferably a chloro atom); and Q is Y and Y is selected from hydrogen, —C(O)R, —SO$_2$R$_1$, —C(O)NR$_2$R$_3$; R$_3$ is hydrogen, R and R$_1$ and R$_2$ (being the same or different) are selected from phenyl optionally substituted with one to three C$_1$–C$_4$ alkyl, C$_1$–C$_3$ alkoxy, halo, C$_1$–C$_3$, alkylthio, trifluoromethyl, C$_2$–C$_6$ dialkylamino, or nitro; and R'$_{15}$ is selected from (dd), (ddd), (dddd), (ee) or (eee) wherein n is 0–6; X$_{10}$ is —NH— or —O—; X$_5$ and X$_6$ are both hydrogen; and R$_{50}$ is selected from either i) N-hydroxysuccimidyl or maleimidyl; ii) —B—M—(CH$_2$)n$_3$R$_{52}$ wherein R$_{52}$ is —NH$_2$, —C(O)NHNH$_2$, —CO$_2$H, or —SH; or iii) —CO$_2$H, —CH$_2$NH$_2$, —SH, —C(R$_{60}$)(R$_{61}$)SH, —NHC(O)—(CH$_2$)$_{n1}$—C(R$_{60}$)(R$_{61}$)—SH, —C(O)NHNH$_2$, —CH$_2$OH, —C(R$_{60}$)(R$_{61}$)C(O)NHNH$_2$, —N(R$_{62}$)(CH$_2$)$_{n1}$C(R$_{60}$)(R$_{61}$)C(O)—NHNH$_2$, —O(CH$_2$)n$_2$C(R$_{60}$)(R$_{61}$)C(O)NHNH$_2$; wherein n$_1$ is 1–3; n$_2$ is 0–2; and R$_{60}$, R$_{61}$ and R$_{62}$, being the same or different, are H, methyl or ethyl.

Another embodiment of the subject invention are compounds of Formula II wherein W is methyl; Z is hydrogen; and R'$_{15}$ is selected from (dd), (ddd), (dddd), (ee) or (eee) wherein n is 0–6; X$_{10}$ is —NH— or —O—; X$_5$ and X$_6$ are independently H, OH, NO$_2$, NHC(O)CH$_3$, halo, C$_1$–C$_4$ alkyl, C$_1$–C$_3$ alkoxy or C$_2$–C$_6$ dialkylamino; and R$_{50}$ is preferably —CO$_2$H, —CH$_2$NH$_2$, —SH, —C(R$_{60}$)(R$_{61}$)SH, —NHC(O)—(CH$_2$)$_{n1}$—C(R$_{60}$)(R$_{61}$)—SH, —C(O)NHNH$_2$, —CH$_2$OH, —C(R$_{60}$)(R$_{61}$)C(O)NHNH$_2$, —N(R$_{62}$)(CH$_2$)$_{n1}$C(R$_{60}$)(R$_{61}$)C(O)—NHNH$_2$, —O(CH$_2$)n$_2$C(R$_{60}$)(R$_{61}$)C(O)NHNH$_2$; wherein n$_1$ is 1–3; n$_2$ is 0–2; R$_{60}$, R$_{61}$ and R$_{62}$, being the same or different, are H, methyl or ethyl.

A preferred embodiment of the subject invention are compounds of Formula II wherein W is methyl; Z is hydrogen; and R'$_{15}$ is selected from (dd), (ddd), (dddd), (ee) or (eee) wherein n is 0–6; X$_{10}$ is —NH— or —O—; X$_5$ and X$_6$ are both hydrogen; and R$_{50}$ is preferably —CO$_2$H, —CH$_2$NH$_2$, —SH, C(R$_{60}$)(R$_{61}$)SH, —NHC(O)—(CH$_2$)$_{n1}$—C(R$_{60}$)(R$_{61}$)—SH, —C(O)NHNH$_2$, —CH$_2$OH, —C(R$_{60}$)(R$_{61}$)C(O)NHNH$_2$, —N(R$_{62}$)(CH$_2$)$_{n1}$C(R$_{60}$)(R$_{61}$)C(O)—NHNH$_2$, —O(CH$_2$)$_{n2}$C(O)NHNH$_2$; wherein n$_1$ is 1–3; n$_2$ is 0–2; R$_{60}$, R$_{61}$and R$_{62}$, being the same or different, are H, methyl or ethyl.

Another embodiment of the subject invention are compounds of Formula II wherein W is methyl; Z is hydrogen; and R'$_{15}$ is (dd); X$_{10}$ is —NH— or —O—; X$_5$ and X$_6$ are independently H, OH, NO$_2$, NHC(O)CH$_3$, halo, C$_1$–C$_4$ alkyl, C$_1$–C$_3$ alkoxy or C$_2$–C$_6$ dialkylamino; and R$_{50}$ is preferably —CO$_2$H, —CH$_2$NH$_2$, —SH, —C(R$_{60}$)(R$_{61}$)SH, —NHC(O)—(CH$_2$)$_{n1}$—C(R$_{60}$)(R$_{61}$)—SH, —C(O)NHNH$_2$, —CH$_2$OH, —C(R$_{60}$)(R$_{61}$)C(O)NHNH$_2$, —N(R$_{62}$)(CH$_2$)$_{n1}$C(R$_{60}$)(R$_{61}$)C(O)—NHNH$_2$, —O(CH$_2$)$_{n2}$C(R$_{60}$)(R$_{61}$)C(O)NHNH$_2$; wherein n$_1$ is 1–3; n$_2$is 0–2; R$_{60}$, R$_{61}$ and R$_{62}$, being the same or different, are H, methyl or ethyl; or ii) N-hydroxysuccimidyl or maleimide.

A preferred embodiment of the subject invention are compounds of Formula II wherein W is methyl; Z is hydrogen; and R'$_{15}$ is (dd) wherein n is 0–6; X$_{10}$ is —NH— or —O—; X$_5$ and X$_6$ are both hydrogen; and R$_{50}$ is preferably i) —CO$_2$H, —CH$_2$NH$_2$, —SH, —C(R$_{60}$)(R$_{61}$)SH, —NHC(O)—(CH$_2$)$_{n1}$—C(R$_{60}$)(R$_{61}$)—SH, —C(O)NHNH$_2$, —CH$_2$OH, —C(R$_{60}$)(R$_{61}$)C(O)NHNH$_2$, —N(R$_{62}$)(CH$_2$)$_{n1}$C(R$_{60}$)—(R$_{61}$)C(O)—NHNH$_2$, —O(CH$_2$)$_{n2}$C(R$_{60}$)(R$_{61}$)C(O)NHNH$_2$; wherein n$_1$ is 1–3; n$_2$is 0–2; R$_{60}$, R$_{61}$ and R$_{62}$, being the same or different, are H, methyl or ethyl; or ii) N-hydroxysuccimidyl or maleimide.

Another embodiment of the subject invention are compounds of Formula I wherein Y is selected from hydrogen, —C(O)R, —C(S)R, —C(O)OR$_1$, —S(O)$_2$R$_1$, —C(O)NR$_2$R$_3$, —C(S)NR$_2$R$_3$, —C(O)NHSO$_2$R$_4$, —C(O)CH$_2$(OCH$_2$CH$_2$)$_{n7}$O(C$_1$–C$_3$ alkyl) and n7 is 0–5 (preferably 2 or 3) or —C(O)(CH$_2$)$_{n8}$C(O)R$_b$ where n8 is 0–10 (preferably 2, 3 or 4) and R$_b$ is selected from —OH (or a metal or amine salt thereof), —OR$_c$ where R$_c$ is —CH$_2$C(CH$_2$OH)$_3$ or R$_{70}$, and —N(R$_d$) R$_e$ where R$_d$ is hydrogen or C$_1$–C$_4$ alkyl, and R is selected from —C(CH$_2$OH)$_3$, —CH$_2$C(CH$_2$OH)$_3$, —CH$_2$C(CH$_2$NH$_2$)$_3$, R$_{70}$, R$_{71}$ or R$_{72}$ where n9 is 1 or 2 and n10 is 1–3.

Examples of preferred compounds include the relatively more water soluble compounds of Formula I include those where Y is 3,6,9-trioxadecanoyl, N-[2-hydroxy-1,1-bis (hydroxymethyl)ethyl]glutaramyl or 7-glutaramyl-naphthalene-1,3-disulfonic acid salts. See for example, compounds 18, 19 and 21–24.

The compounds of Formula I and II are readily prepared by reacting the appropriate spirocyclopropylcyclohexadienyl analog (Formula II) with the Y'—X reagent or with H—X and then acylating with Y—X' where X' is an active leaving group, for example halide, azide, sulfonate, and the like. The starting spirocyclopropylcyclohexadienyl analog (Formula II) is dissolved in an inert solvent such as methylene chloride, tetrahydrofuran (THF), N,N-dimethylformamide (DMF, DMFA), dimethylacetamide (DMA), pyridine, dioxane, N-methylpyrrolidone and the like. The resultant solution is treated with the reagent Y'—X and the solution stirred at ambient temperature until thin layer chromatography (TLC) shows the reaction to be complete (normally for reactive acyl halides in a few minutes but for weak acids or acylating agents a few hours or days may be required. For very reactive reagents the temperature may be lowered to –20° C. or less and for relatively unreactive addents the temperature may be raised to 80° C. or higher depending upon the solvent). When the reaction is complete, the solution is diluted with an appropriate solvent (methylene chloride, ethyl acetate, ether, THF (with brine), and the like. The organic layer is extracted with a mild base such as sodium or potassium bicarbonate, washed with water, dried by a suitable drying agent such as anhydrous magnesium sulfate or anhydrous sodium sulfate. Filtration of the drying agent and evaporation of the solvent leaves the desired product which may be used as such or purified by crystallization or chromatography by methods well know to those skilled in the art.

EXAMPLE 1

Preparation of (S)-2-[[[2-[[1-(chloromethyl)-1,6-dihydro-5-hydroxy-8-methylbenzol[1,2-b:4,3-b']dipyrrol-3(2H)-yl]carbonyl]-1H-indol-5-yl]amino]carbonyl]-2-benzofuran-5-carboxylic acid phenylmethyl ester (Cpd #1);

Part A. Preparation of benzofuran-2,5-dicarboxylic acid bis-(phenylmethyl) ester (Formula B, General Formulae Chart).

A 2.48 g (12 mmole) quantity benzofuran-2,5-dicarboxylic acid (Formula A: General Formulae Chart) is stirred at room temperature (~25° C.) under nitrogen in 20 ml dimethyl acetamide. To this is added 1.29 ml (12 mmoles) benzyl alcohol, 170 mg dimethylaminopyridine and 2.49 g 1-ethyl-3-(3-dimethylaminopropyl)carbodiimide. The reaction is left to react for 24 hours, when TLC shows some staining material left, some bis ester but mostly a mono ester-mono acid.

The reaction mixture is partitioned between ethyl acetate-water. The layers are separated and the aqueous layer reextracted with ethyl acetate. The organic layers are combined, dried over sodium sulfate and evaporated under vacuum.

The crude product is redissolved in ethyl acetate and the solution evaporated under vacuum onto 40 g of silica gel. This as added to the top of a 400 g silica gel column and eluted with 15% ethyl acetate, 83% hexane, 2% acetic acid. A forerun of 400 mL is collected followed by 50 mL fractions. The desired bis benzyl ester elutes in fractions 24–43. Evaporation of these fractions leaves 308 mg of benzofuran 2,5-dicarboxylic acid bis benzyl ester.

TLC: Silic gel: Uv visualization; 15% ethyl acetate, 85% hexane, 2% acetic acid; $R_f$ 0.54.

Mass Spectrum: M+H and M at 387 and 386 respectively. Other fragment ions at 279 and 91.

NMR(CDCl$_3$, TMS) δ 5.39 (S, 2H); 5.43 (s, 2H); 7.30–7.53 (m, 10H); 7.57–7.69 (d 2H); 8.16–8.25 (dd, 1H); 8.45 and 8.46 (d, 1H).

The elution is continued with 25% ethyl acetate, 73% hexane, 2% acetic acid. The benzofuran 2,5-dicarboxylic acid 2-phenylmethyl ester is isolated by evaporation of fractions 56–208 (1.53 g).

TLC: Silic gel: Uv visualization; 15% ethyl acetate, 85% hexane, 2% acetic acid; $R_f$ 0.36. NMR(CDCl$_3$, TMS): δ 2.7–3.2 (bs, 1H); 5.45 (s, 2H); 7.3–7.5 (m, 3H); 7.5–7.6 (m, 2H); 7.75 and 7.78 (d, 1H); 7.85 (d, 1H); 8.17–8.23 (dd, 1H); 8.53 (d, 1H).

Resubmission of the above benzofuran-2,5-dicarboxylic acid 2-phenyl methyl ester to the esterification conditions of pan A gives the benzofuran 2,5-dicarboxylic acid his phenylmethyl ester in 80% yield.

Part B: Preparation of the benzofuran-2,5-dicarboxylic acid 5-phenylmethyl ester (Formula C, General Formulae Chart).

A 1.11 g (2.87 mmole) quantity of the bis benzyl ester (Part A; Formula B), is dissolved with stirring at room temperature (~25° C.) under nitrogen in 20 ml THF-5 ml DMF. To this added two 2.5 ml batches of 1N NaOH, following the reaction by TLC to make sure the reaction is stopped at the mono ester stage.

After 45 minutes reaction time 6 ml 1N HCl is added. The reaction is partitioned between ethyl acetate-brine. The layers are separated and the aqueous layer reextracted with ethyl acetate. The organic layers are combined, dried over sodium sulfate and evaporated, using high vacuum at the end.

The crude product is coated on 10 g silica gel and chromatographed over 100 g silica gel. Elute with 700 ml 30% ethyl acetate-2% acetic acid-68% hexane, followed by 800 ml 40% ethyl acetate-2% acetic acid-58% hexane. Fractions of 20 ml are collected, analyzing them by TLC. The product is found in fractions 28–54, which upon combining and evaporating leaves 870 mg solid, 94% yield.

TLC: silica gel; UV visualization; 15% ethyl acetate-85% hexane-2% acetic acid; Rf: 0.08 Mass spectrum: Major ions at 296, 278, 251, 189, 91. NMR(d$_6$-acetone,TMS): δ 5.42 (s, 2H); 7.3–7.5 (m, 3H); 7.5–7.6 (m, 2H); 7.75 and 7.78 (d, 1H); 7.8 (d, 1H); 8.19–8.25 (dd, 1H); 8.54 (d, 1H).

Part C: Preparation of the amide of Formula E (General Formulae Chart).

A 40 mg (0.13 mmole) quantity of the amine of Formula D (General Formulae Chart) is stirred at room temperature (~25° C.) in the dark and under nitrogen in 1 ml DMF. To this solution is added 39 mg (0.13 mmole) of the acid (Formula C) and 27 mg 1-ethyl-3-(3-dimethylaminopropyl) carbodiimide. The reaction starts out as two phases but everything dissolves during the 17 hour reaction time.

After the given reaction time the reaction mixture is partitioned between ethyl acetate-water. The layers are separated and the aqueous layer reextracted with ethyl acetate. The organic layers are combined, dried over sodium sulfate and evaporated under vacuum.

The crude product is coated on 1 g silica gel and chromatographed over 9 g silica gel. The column is eluted with the following mounts of ethyl acetate-hexane: 80 ml 30–70, 40 ml 40–60, 60 ml 50–50, 20 ml 60–40, 20 ml 70–30, 20 ml 80–20, 20 ml 90–10, and 100 ml pure ethyl acetate, the product dragging off due to insolubility. Fractions of 2 ml are collected, analyzing them by TLC. Product is found in fractions 26–110, which upon combining and evaporating under vacuum leave 68 mg (89% yield) solid.

Mass spectrum: M+H at 585, 587, 589; other major ions at 279, 91. TLC: silica gel; UV visualization; 30% ethyl acetate-70% hexane; Rf: 0.59 NMR(d$_6$-DMSO, TMS): δ 5.19 (s, 2H); 5.41 (s, 2H); 7.3–7.6 (m, 7H); 7.66–7.74 (d, 1H); 7.83–7.90 (d, 1H); 7.90 (s, 1H); 8.10–8.17 (d, 1H); 8.23 (s, 1H); 8.54 (s, 1H); 10.65 (s, 1H); 12.17 (s, 1H).

Part D: Hydrolysis of the trichloroethyl ester (Formula E, Part C).

A 50 mg (0.085 mmole) quantity of the trichloroethyl ester (Formula E, General Formulae Chart) is stirred at 60° C. under nitrogen in 10 ml acetic acid. To this partially solubilized mixture is added 75 mg zinc. After a few minutes most of the solids dissolve and then a new solid forms. The reaction is left to react for one hour at 60° C. and then cooled to room temperature (~25° C.), diluted with DMF and filtered. The solid is washed with DMF, combining filtrate and wash and evaporating under high vacuum.

The above crude product is coated on 500 mg silica gel and chromatographed over 5 g silica gel. The column is eluted with 30 ml 10%DMF-90% toluene-2% acetic acid and 50 ml of 20-80-2 of the same solvents. Fractions of 2 ml are collected, analyzing them by TLC. Fractions 12–30 contained the major product (Formula F, General Formulae Chart) and are combined and evaporated under vacuum. This leaves 25 mg solid, 67% yield.

Mass spectrum: M+Na at 447; M+H at 455; other major ion at 279. TLC: silica gel; UV visualization; 10% DMF-90% toluene-2% acetic acid; Rf: 0.16. NMR: d$_6$-DMSO, TMS: δ 5.41 (s, 2H); 7.10 (s, 1H); 7.3–7.7 (m, 7H); 7.85 and 7.88 (d, 1H); 7.89 (s, 1H); 8.12 and 8.15 (d, 1H); 8.17 (s, 1H); 8.54 (s, 1H); 10.58 (s, 1H); 11.77 (s, 1H); 12.6–13.1 (bs, 1H).

Part E: Preparation of (S)-2-[[[[2-[[1-(chloromethyl)-1,6-dihydro-5-hydroxy- 8-methylbenzo[1,2-b:4,3-b')dipyrrol-3 (2H)yl]carbonyl]-1H-indol-5-yl]amino]carbonyl]2-benzofuran-5-carboxylic acid phenylmethyl ester (Cpd #1).

A 56 mg (0. 17 mmole) quantity, (S)-1-(chloromethyl)-1,6-dihydro-5-hydroxy-8-methylbenzo[1,2b:4,3-b'] dipyrrole-3(2H)-carboxylic acid 1,1-dimethyl ester (BOC chlorophenol), is stirred at room temperature (~25° C.) in the dark and under nitrogen for one hour in 2 ml ethyl acetate and 3 ml ethyl acetate saturated with gaseous HCl. Silica gel TLC in 30% ethyl acetate-70% hexane shows all of the starting material spot is replaced by a spot at the origin. The solvent is then evaporated under vacuum, and then methylene chloride is added to the residue which is reevaporated under vacuum.

The resultant solid residue is dissolved in 1.5 ml dimethylacetamide. To this solution is added 77 mg (0.17 mmoles) of the acid (Formula F) and 32 mg (0.17 mmoles) 1-ethyl-3-(3-dimethylaminopropyl)-carbodiimide (EDC). The solution is left to react for one hour, after which is added 20 mg more acid and 8 mg more EDC. The reaction is allowed to react for 3 hours more.

The reaction mixture is partitioned between brine-ethyl acetate-THF. The layers are separated and the aqueous layer reextracted with ethyl acetate. The organic layers are combined, dried over sodium sulfate and evaporated.

The crude product is coated on 1 g silica gel and chromatographed over 10 g silica gel. The column is eluted with a gradient of 10% DMF-90% toluene to 20% DMF-80% toluene. Fractions of 2 ml are collected, analyzing them by TLC. The product is found in fractions 30–43, which upon combining and evaporating under high vacuum leave 84 mg yellow solid, a 74% yield.

TLC: silica gel; UV visualization; 10% DMF-90% toluene; RF: 0.30 UV(MeOH): 295 nm (35,670); 340 nm (24,900). Mass spectrum: M+H at 673, 675; M at 672, 674; other major ions at 437, 279, 237, 236, 199, 187. NMR: $d_6$-DMSO, TMS: δ 2.36 (s, 3H); 3.5–3.67 (t, 1H); 3.83–3.95 (d, 1H); 3.95–4.07 (t, 1H); 4.47–4.59 (d, 1H); 4.59–4.74 (t, 1H); 5.41 (s, 2H); 7.06 (s, 1H); 7.16 (s, 1H); 7.32–7.75 (m, 8H); 7.86 and 7.89 (d, 1H); 7.90 (s, 1H); 8.12 and 8.15 (d, 1H); 8.22 (s, 1H); 8.54 (s, 1H); 9.82 (s, 1H); 10.61 (s, 1H); 10.75 (s, 1H); 11.73 (s, 1H).

EXAMPLE 2

Preparation of (S)-2-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-2-benzofuran-5-carboxylic acid (Cpd #2);

A 10 mg (0.015 mmole) quantity of (S)-2-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]- 2-benzofuran-5-carboxylic acid phenylmethyl ester (Cpd #1) is stirred at room temperature (~25° C.) in 0.3 ml THF-0.1 ml MeOH in the dark. To this solution is added 10 mg 10% palladium on carbon and 8 mg ammonium formate. The mixture is heated to 50° C. for 15 minutes, when TLC shows the reaction to be complete.

The reaction is cooled to room temperature (~25° C.) and partitioned between ethyl acetate, 1 ml 1N HCl-25 ml water. The layers are separated and the aqueous layer reextracted with ethyl acetate. The organic layers are combined, dried over sodium sulfate and evaporated under vacuum, leaving 8 mg (S)-2-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-2-benzofuran-5-carboxylic acid, 89% yield.

NMR($d_6$-DMSO, TMS): δ 2.36 (s, 3H); 3.53–3.67 (m, 1H); 3.86–3.97 (d, 1H); 3.97–4.09 (t, 1H); 4.48–4.60 (d, 1H); 4.60–4.75 (t, 1H); 7.05 (s, 1H); 7.15 (s, 1H); 7.44–7.54 (s, 1H); 7.56–7.64 (d, 1H); f7.65 (bs, 1H); 7.78–7.87 (d, 1H); 7.90 (s, 1H); 8.05–8.13 (d, 1H); 8.21 (s, 1H); 8.48 (s, 1H); 9.83 (s, 1H); 10.59 (s, 1H); 10.75 (s, 1H); 11.71 (s, 1H); 12.6–13.3 (bs, 1H).

UV(MeOH): 340 nm (21,860); 294 nm (32,360). Mass spectrum: M+H at 583, 585; M at 582, 584. Other ions at 347,237,236. TLC: silica gel; UV visualization; 20% DMF-80% toluene-2% acetic acid; Rf: 0.44.

EXAMPLE 3

Preparation of (S)-2-[[[-2-[(4,5,8,8a-tetrahydro-7-methyl-4-oxocyclopropa[c]pyrrol[3,2-e]indol-2(1H)-yl)-carbonyl]-1H-indol-5-yl]amino]carbonyl]-2benzofuran-5-carboxlyic acid (Cpd #3);

A 61 mg (0.01 mmole) quantity of (S)-2-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-2-benzofuran-5-carboxylic acid (Cpd #2); is stirred at room temperature (~25° C.) in the dark under nitrogen in 2.4 ml acetonitrile, 1.2 ml triethylamine, 1.2 ml water for 30 minutes, resulting in complete solution.

The reaction mixture is partitioned between ethyl acetate-water. The organic layer is dried over sodium sulfate and evaporated. Insufficient material is recovered by the above extraction. Thus, the aqueous layer is acidified with pH3 phosphate buffer and extracted twice with a 50-50 mixture of ethyl acetate and freshly distilled THF. The organic layers are dried over sodium sulfate, combined with the first ethyl acetate extract and evaporated under vacuum. This leaves 53 mg product (Cpd #3), 93% yield.

TLC: silica gel; UV visualization; 20% DMF-80% toluene-2% acetic acid: Rf: 0.37. NMR($d_6$-DMSO, TMS): δ 1.42–1.52 (m, 1H); 1.95–2.05 (m, 1H); 2.05 (s, 3H); 3.15–3.30 (m, 1H); 4.45–4.55 (d, 1H); 4.56–4.67 (dd, 1H); 6.77 (s, 1H); 6.94 (s, 1H); 7.27 (s, 1H); 7.48–7.58 (d, 1H); 7.64–7.75 (d, 1H); 7.84–7.92 (d, 1H); 7.93 (s, 1H); 8.10–8.20 (d, 1H); 8.28 (s, 1H); 8.52 (s, 1H); 10.64 (s, 1H); 11.60 (s, 1H); 11.89 (s, 1H). UV(MeOH): 356 nm (19670); 309 nm (26,230). Mass spectrum: M+H at 547; other ions at 347, 201. Adding HCl gives an M+HCl+H at 583.

EXAMPLE 4

Preparation of (S)-2-[[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-1H-indol-5-yl]-carbamic acid, 1,1-dimethylethyl ester (Cpd #4);

Part A: Preparation of Formula H (General Formulae Chart).

A 0.5 g (2.45 mmole) quantity of the amine (Formula G: General Formulae Chart), is stirred at room temperature (~25° C.) in the dark under nitrogen in 5 ml freshly distilled THF. To this is added 610 mg (2.45 mmole) BOC-ON and 350 ul (2.45 mmole) triethylamine. After 3 days at room temperature (~25° C.) the reaction is found by TLC to be essentially completed.

The reaction is then partitioned between ethyl acetate, brine. The layers are separated and the aqueous layer reextracted with ethyl acetate. The combined organic layers are dried over sodium sulfate and evaporated under vacuum.

The crude product is coated on 10 g silica gel and chromatographed over 90 g silica gel. The column is eluted with a gradient of 10% ethyl acetate-90% hexane to 25% ethyl acetate-75% hexane. Fractions of 15 ml are collected, analyzing them by TLC. The product is found in fractions 55–119 which upon combining and evaporating under vacuum leaves 617 mg solid, (Formula H), 83% yield.

TLC: silica gel; UV visualization; 30% ethyl acetate-70% hexane; Rf: 0.63. Mass spectrum: Major ions at 304, 248, 202, 158, 130, 102, 57. NMR(CDCl3), TMS): δ 1.38–1.47 (t, 3H); 1.53 (s, 9H); 4.35–4.45 (q, 2H); 6.50 (s, 1H); 7.13–7.16 (d, 1H); 7.18–7.24 (dd, 1H); 7.30–7.38 (d, 1H); 7.79 (s, 1H); 8.85 (bs, 1H).

Part B: Hydrolysis of the ethyl ester (Formula H).

A 617 mg (2.03 mmole) quantity of the ethyl ester (Part A, Formula H) is stirred at room temperature (~25° C.) under nitrogen in 10 ml pyridine-10 ml MeOH-10 ml water-5 ml 1N NaOH, resulting in complete solution. The reaction is followed by TLC and is found to be complete after 20 hours.

The reaction is then treated with 5 ml 1N HCl and evaporated under vacuum. The residue is partitioned between ethyl acetate-water-3 ml 1N HCl. The layers are separated and the aqueous layer reextracted with ethyl acetate. The organic layers are combined, dried over sodium sulfate and evaporated under vacuum. This leaves 620 mg solid (Formula J), 100% yield.

TLC: silica gel; UV visualization; 30% ethyl acetate-70% hexane-2% acetic acid; Rf: 0.25. Mass spectrum: major ions at 276, 220, 202, 176, 158, 130. NMR($d_6$-DMSO, TMS): δ 1.50 (s, 9H); 7.13–7.17 (d, 1H); 7.37–7.49 (m, 2H); 7.97 (s, 1H); 8.31 (bs, 1H); 10.77 (bs, 1H).

Part C: Preparation of the ethyl ester (amide) (Formula L, General Formulae Chart).

A 620 mg (2.03 mmoles) quantity of the acid (Part B: Formula J, General Formulae Chart), is stirred at room temperature (~25° C.) under nitrogen and in the dark with 4 ml dry DMF, giving a complete solution. To this is added 415 mg (2.03 mmoles) amine and 390 mg 1-ethyl-3-(3-dimethylaminopropyl) carbodiimide. After 5 days the reaction mixture is partitioned between ethyl acetate-water. The layers are separated and the aqueous layer reextracted with ethyl acetate. The organic layers are combined, dried over sodium sulfate and evaporated under vacuum.

The crude product is coated on 10 g silica gel and chromatographed over 90 g silica gel. The column is eluted with 10% DMF-90% toluene. Fractions of 20 ml are collected, analyzing them by TLC. Fractions 24–53 contained the product and are combined and evaporated under vacuum. This leaves 890 mg solid (Formula L), 95% yield.

TLC: silica gel; UV visualization; 10% DMF-90% toluene; Rf: 0.45. Mass spectrum: major ions at 539, 463, 462, 407, 406, 259, 204, 203, 159, 158, 57. NMR($d_6$-DMSO, TMS): δ 1.3–1.4 (t, 3H); 1.49 (s, 9H); 4.3–4.4 (q, 2H); 7.16 (s, 1H); 7.20–7.27 (d, 1H); 7.28–7.38 (m, 2H); 7.4–7.5 (d, 1H); 7.55–7.64 (d, 1H); 7.80 (s, 1H); 8.14 (s, 1H); 9.17 (s, 1H); 10.13 (s, 1H); 11.58 (s, 1H); 11.89 (s, 1H).

Part D: Hydrolysis of ethyl ester (Formula L).

An 890 mg (1.92 mmole) quantity of the ethyl ester (Part C, Formula L), is stirred at room temperature (~25° C.) under nitrogen and in the dark in 10 ml pyridine-3 ml 1N NaOH, giving a complete solution. The reaction is followed by TLC and after 20 hours shows no starting material left.

At this time 3 ml 1N HCl is added and the mixture evaporated under vacuum. The residue is partitioned between brine-5 ml 1N HCl-freshly distilled THF-ethyl acetate. The layers are separated and the aqueous layer reextracted with ethyl acetate. The organic layers are combined, dried over sodium sulfate and evaporated under vacuum.

The crude product is coated on 10 g silica gel and chromatographed over 70 g silica gel. The column is eluted with 500 ml 20% DMF-80% toluene-2% acetic acid, followed by 300 ml 30-70-2 and 40-60-2 of the same. A forerun of 100 ml is collected, followed by 15 ml fractions. The fractions are analyzed by TLC and product is found in fractions 30–52. These are combined and evaporated under vacuum, leaving 930 mg (Formula M), 100% yield.

Mass spectrum: major ions at 435, 434, 379, 378, 361, 177, 176, 159, 158, 57. TLC: silica gel; UV visualization; 20% DMF-80% toluene-2% acetic acid; Rf: 0.35. NMR($d_6$-DMSO, TMS): δ 1.49 (s, 9H); 7.08 (s, 1H); 7.18–7.27 (d, 1H); 7.27–7.38 (m, 2H); 7.38–7.46 (d, 1H); 7.5–7.6 (d, 1H); 7.80 (s, 1H); 7.95 (s, 1H); 8.12 (s, 1H); 9.16 (s, 1H); 10.10 (s, 1H); 11.58 (s, 1H); 11.73 (s, 1H).

Part E: Preparation of (S)-2-[[[[2-[[1-(chloromethyl)-1,6-dihydro-5-hydroxy-8-methylbenzo[1,2-b:4,3-b']dipyrrol-3 (2H)-yl]carbonyl]-1H-indol-5-yl]amino]carbonyl]-1H-indol-5-yl]-carbamic acid, 1,1-dimethylethyl ester (Cpd #4).

A 120 mg (0.36 mmole) quantity of (S)-1-(chloromethyl)-1,6-dihydro-5-hydroxy-8-methyl-benzol[1,2b:4,3-b']dipyrrole-3(2H)-carboxylic acid 1,1-dimethyl ester (BOC chlorophenol), is stirred for 1.5 hours at room temperature (~25° C.) in the dark and under nitrogen in 4 ml ethyl acetate-6 ml ethyl acetate saturated with gaseous HCl. TLC shows all of the starting material to have reacted at that time.

The solvent is evaporated under vacuum. Methylene chloride is added to the residue and the mixture reevaporated under vacuum. The residue is dissolved in 4 ml dimethylacetamide.

A 1.7 ml aliquot of the DMA solution (0.15 mmoles) is stirred at room temperature (~25° C.) in the dark under nitrogen, and treated with 65 mg (0.15 mmoles) acid (Part D: Formula M) and 28 mg 1-ethyl-3-(3-dimethylaminopropyl) carbodiimide (EDC). After 45 minutes an additional 16 mg of acid and 7 mg of EDC are added.

After an additional 3 hrs file reaction mixture is partitioned between ethyl acetate-THF-brine. The layers are separated and the aqueous layer reextracted with THF-ethyl acetate. The organic layers are combined, dried over sodium sulfate and evaporated under vacuum.

The crude product is coated on 1 g silica gel and chromatographed over 10 g silica gel. The column is eluted with a gradient of 10% DMF-90% toluene to 20% DMF-80% toluene. Fractions of 2 ml are collected, analyzing them by TLC. The product is found in fractions 16–30, which upon combining and evaporating under vacuum leaves 92 mg solid, 94% yield.

UV(MeOH): 298 nm (35,920); 340 nm (30,040). TLC: silica gel; UV visualization; 10% DMF-90% toluene; Rf: 0.21. NMR($d_6$-DMSO, TMS): δ 1.50 (s, 9H); 2.08 (s, 3H); 3.54–3.66 (t, 1H); 3.85–3.95 (d, 1H); 3.98–4.09 (t, 1H); 4.5–4.6 (d, 1H); 4.6–4.74 (t, 1H); 7.06 (s, 1H); 7.15 (s, 1H) 7.20–7.29 (d, 1H); 7.3–7.4 (m, 2H); 7.45–7.53 (d, 1H); 7.53–7.60 (d, 1H); 7.67 (bs, 1H); 7.83 (s, 1H); 7.95 (s, 1H); 8.23 (s, 1H); 9.17 (s, 1H); 9.81 (s, 1H); 10.15 (s, 1H); 10.74 (s, 1H); 11.63 (s, 1H); 11.69 (s, 1H).

Mass spectrum: M+H at 653, 655; M at 652, 654; other major ions at 729, 597, 361, 237, 236, 159, 57.

EXAMPLE 5

Preparation of (S)-N-[2-[[1-(chloromethyl)-1,6-dihydro-8-methyl-5-[[[[4-[[[(1,1-dimethylethyl)oxy]carbonyl]aminomethyl]phenyl]amino]carbonyl]oxy]benzo[1,2-b:4,3-b']-dipyrrol-3(2H)-yl]carbonyl]-1H-indol-5-yl]-2-benzofurancarboxamide (Cpd #5).

Part A: Preparation of Formula N (General Formulae Chart).

A 1.0 g (5.3 mmoles) quantity p-nitrobenzylamine hydrochloride is stirred at room temperature (~25° C.) under nitrogen in 14 ml freshly distilled THF in the dark. To this is added 1.51 ml triethylamine and 1.32 g BOC-ON. This results in a mixture which does not completely dissolve in 24 hrs, so 15 ml more THF is added. The reaction still does not dissolve after another 24 hrs stirring.

At this point, the reaction mixture is partitioned between ethyl acetate -brine. The layers are separated and the aqueous layer reextracted with ethyl acetate. The organic layers are combined, dried over sodium sulfate and evaporated under vacuum.

The crude product is chromatographed over 100 g silica gel, eluting with 20% ethyl acetate-80% hexane. Fractions of 15 ml are collected, analyzing them by TLC. The following fractions are combined and evaporated under vacuum:

Fractions 33–44, desired product and side product

Fractions 45–67, desired product

Other TLC systems tried for separating mixed fractions: 10% acetone-90% hexane (worse); toluene (worse); methylene chloride (worse); 10% ethyl acetate-90% toluene (similar).

Fractions 33–44 are flash chromatographed over 100 g silica gel 60, eluting with 10% ethyl acetate-90% toluene. A forerun of 100 ml is collected, followed by 20 ml fractions. TLC analysis shows fractions 18–23 to be mixed and fractions 24–42 to be pure product, the latter combined with pure product above. The mixed fractions are rechromatographed over the same column, pure product being found in fractions 21–42. These are combined with pure product above to give a total of 1.28 g, 95% yield.

TLC: silica gel; UV visualization; 10% ethyl acetate-90% hexane; Rf: 0.10 Mass spectrum: major ions at 252, 237, 197, 196, 179, 57. NMR(CDCl3), TMS): δ 1.50 (s, 9H); 4.35–4.48 (d, 2H); 5.01 (bs, 1H); 7.43 and 7.46 (d, 2H); 8.18 and 8.21 (d, 2H).

Part B: Preparation of Formula O (General Formulae Chart).

A 500 mg (1.98 mmole) quantity of the nitro compound (Part A: Formula P), is dissolved in 5 ml freshly distilled THF and 15 ml absolute ethanol. The solution is treated with 75 mg platinum oxide and hydrogenated under pressure at room temperature (~25° C.) for 2 hours.

The reaction mixture is filtered and the catalyst washed with more freshly distilled THF. The filtrate and wash are combined and evaporated under vacuum, giving a solid in a 100% yield.

TLC: silica gel; UV visualization; 20% ethyl acetate-80% hexane; Rf: 0.28. Mass spectrum: major ions at 222, 165, 121, 106, 77, 57. NMR(CDCl3), TMS): δ 1.45 (s, 9H); 3.5–3.8 (bs, 2H); 4.13–4.20 (d, 2H); 4.70–4.85 (bs, 1H); 6.60–6.65 (d, 2H); 7.03–7.10 (d, 2H).

Part C: Preparation of (S)-N-[2-[[1-(chloromethyl)-1,6-dihydro-8-methyl-5-[[[[4-[[[(1,1-dimethylethyl)oxy]carbonyl]aminomethyl]phenyl]amino]carbonyl]oxy]benzo[1,2b:4,3-b']-dipyrrol-3(2H)-yl]carbonyl]-1H-indol-5-yl]-2-benzofurancarboxamide (Cpd #5).

A 5 ml quantity 20% phosgene in toluene (1.93 molar, 9.65 mmoles) is stirred at room temperature (~25° C.) under nitrogen. To this is added dropwise over one minute 47 mg (0.2 mmoles) amine (Part B: Formula O) dissolved in 1 ml ethyl acetate. After one hour reaction time the solvent is evaporated under vacuum.

The resultant residue is stirred at room temperature (~25° C.) under nitrogen with 1 ml freshly distilled THF. To this is added 57 mg (0.105 mmoles) (S)-N-[2-[[1-(chloromethyl)-1,6-dihydro-5-hydroxy-8-methylbenzo[1,2-b:4,3-b']dipyrrol-3(2HO-yl]carbonyl]-1H-indol-5-yl]-2-benzofurancarboxamide (see U.S. Pat. No. 4,912,227; incorporated herein by reference) dissolved in 1 ml freshly distilled THF, following by the dropwise addition of 14 ul triethylamine to the isocyanate-urea mixture during one minute. The reaction is heated to 65° C. for 3 hours, and the reaction followed by TLC. 10 ul more triethylamine is added and the heating continued for 2 hours more. The reaction is then allowed to cool to room temperature (~25° C.) overnight followed by 2 hrs more heating at 65° C.

At this point the reaction is cooled to room temperature (~25° C.), filtered, and the solid washed with THF. The filtrate and wash are combined and evaporated under vacuum. The crude residue from evaporation is coated on 1 g silica gel and chromatographed over 9 g silica gel. The column is eluted with 40% acetone-60% hexane, followed by 50-50 of the same. Fractions of 2 ml are collected, analyzing them by TLC. The following fractions are combined and evaporated:

Fractions 35–42, desired product, 29 mg

Fractions 29–34 and 43–56, desired product plus impurities

The mixed fractions are rechromatographed as above except eluting with 10% DMF-90% toluene. Product (Cpd #5) is found in fractions 20–35, giving 28 mg. This gives a total yield of 57 mg or 69% based on (S)-N-[2-[[1-(chloromethyl)-1,6-dihydro-5-hydroxy-8- methylbenzol[1,2-b:4,3-b']dipyrrol-3(2HO-yl]carbonyl]-1H-indol-5-yl]-2-benzofurancaboxamide.

TLC: silica gel; UV visualization; 50% acetone-50% hexane; RF: 0.49. UV(MeOH): 320 nm (31,490); 292 mn (40,150). Mass spectrum: M at 787, 789; other major ions at 687, 670, 538, 303, 236, 200, 199, 187, 145, 106, 57. NMR($d_6$DMSO, TMS): δ 1.40 (s, 9H); 2.42 (s, 3H); 3.70–3.82 (t, 1H); 3.95–3.15 (m, 3H); 4.13–4.24 (t, 1H); 4.59–4.68 (d, 1H); 4.70–4.84 (t, 1H); 7.17–7.25 (m, 4H); 7.30–7.44 (m, 2H); 7.44–7.57 (m, 4H); 7.57–7.66 (d, 1H); 7.73–7.78 (d, 1H); 7.79 (s, 1H); 7.81–7.87 (d, 1H). 7.91 (bs, 1H); 8.23 (s, 1H); 10.33 (s, 1H); 10.50 (s, 1H); 11.22 (s, 1H); 11.74 (s, 1H).

EXAMPLE 6

Preparation of Formula P (General Formulae Chart).

A 1.85 g (10 mmole) quantity of p-nitrobenzoyl chloride is stirred about 10 min at room temperature (~25° C.) under nitrogen in 20 ml pyridine. To the solution is then added 1.08 g benzyl alcohol and the resultant solution is left to react about 65 hrs.

At this point water is added resulting in the precipitation of a white solid. The solid (Formula P) is collected by filtration, washed with water and dried under vacuum, giving 1.79 g product, 70% yield.

TLC: silica gel; UV visualization; 20% ethyl acetate-80% hexane; Rf: 0.75 NMR(CDCl3, TMS): δ 5.41 (s, 2H); 7.31–7.50 (m, 5H); 8.20–8.34 (m, 4H). UV(EtOH): 217 nm (9,780); 259 nm (13,850). IR (Mull): major peaks at 1713, 1523, 2925, 716, 1282, 2953, 745, 1348, 2855, 1123, 695, 2869, 1104, 1323, 1381, 1455, 870, 1605, 1299, 851, 1363, 954, 3114, 787, 1023 $cm^{-1}$. Mass spectrum: major ions at 257, 150, 91.

EXAMPLE 7

Preparation of Formula Q (General Formulae Chart), the amine. A 500 mg (1.94 mmoles) quantity of Formula P (Example 6), is dissolved in 5 ml THF-15 ml 95% ethanol. To this is added 75 mg platinum oxide and the mixture hydrogenated under pressure at room temperature (~25° C.) for 80 minutes. TLC shows no starting material but two more polar products, one moving off the origin only with acid present in the developing solvent.

The catalyst is filtered off, washing it with THF. The filtrate and wash are combined and evaporated under vacuum. The crude product is coated on 5 g silica gel and chromatographed over 50 g silica gel. The column is eluted with 30% ethyl acetate -70% hexane until the less polar product has come off. Then the solvent is switched to 40% ethyl acetate-60% hexane-2% acetic acid. Fractions of 15 ml are collected, analyzing them by TLC. The following fractions are combined and evaporated under vacuum.

Fractions 11–17, 287 mg, 65% yield, desired product

Fractions 33–47, 140 mg, 53% yield, side product

TLC and NMR data indicate the side product to be p-amino benzoic acid from hydrogenolysis of the benzyl ester.

Reducing the hydrogenation time to 20 min. still shows all of the starting material gone as well as overhydrogenation and a 69% yield of desired product.

TLC: silica gel; UV visualization; 20% ethyl acetate-80% hexane; Rf: 0.27 NMR(CDCl3), TMS): δ 4.06 (s, 2H); 5.31 (s, 2H); 6.6–6.7 (d, 2H); 7.3–7.6 (m, 5H); 7.85–7.94 (d, 2H).

IR(Mull): major peaks at 1282, 1171, 3361, 1687, 3457, 1601, 1633, 1118, 2926, 1311, 1381, 2954, 1317, 1519, 730, 2855, 772, 1437, 2868, 1572, 694, 703, 847, 1453, 3225 cm$^{-1}$. UV(EtOH): 215 nm (12,400;) 223 nm (9,000); 296 nm (21,660).

EXAMPLE 8

Preparation of 5-[(2-mercaptopropionyl)amino]-N-[2-(4,5,8,8a-tetrahydro-7-methyl-4-oxocyclopropa[c]pyrrolo[3,2-e]indol-2((1H)-yl)-1H-indol-5-yl]-1H-indole-2-carboxamide, (Cpd #8).

A 2 mg (0.003 mmole) quantity of (S)-2-[[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-1H-indol-5-yl]-carbamic acid, 1,1-dimethylethyl ester (Cpd #4, Example 4) is dissolved in the dark in 100 ul trifluoroacetic acid. TLC after 5 min shows all of the starting material to have reacted. After 30 min reaction time the sample is evaporated under a stream of nitrogen.

1 g Dowex 2-X$_8$ anion exchange resin (50–100 mesh, chloride form, quaternary ammonium styrene type, 3.2 meg/dry frame capacity) is mixed with 10 ml 1N HCl, filtered off and washed with deionized water until the pH of the effluent is 6. To this mixture is added 10 ml DMF, mixed well. The resultant mixture is allowed to sit for 5 min, then the solvent is removed by filtration under vacuum. The resin is placed in a small column.

The evaporate residue from the above steps is dissolved in 100 ul DMF and applied to resin and eluted with 5 ml DMF to give the product (Compound JJ).

TLC: reverse phase C18, 80% DMF-20% water, UV visualization, Rf of starting material and product are 0.39 and 0.73 respectively.

NMR(DMSO, TMS): δ 2.50, (s, 3H); 3.54–3.65 (t, 1H); 3.86–3.94 (d, 1H); 3.96–4.08 (t, 1H); 4.47–4.58 (d, 1H); 4.59–4.73 (t, 1H); 7.06 (s, 1H); 7.11–7.23 (m, 2H); 7.43–7.53 (m, 2H); 7.53–7.70 (m, 4H); 8.21 (s, 1H); 9.80 (s, 1H); 9.76–9.98 (bs, 2H); 10.30 (s, 1H); 10.74 (s, 1H); 11.70 (s, 1H); 12.07 (s, 1H).

Part B: Preparation of thiocaetate analog.

A 0.043 mmole quantity of (S)-5-amino-2-[[[2-[[1-(chloromethyl)-1,6-dihydro-5-hydroxy-8-methylbenzo[1,2b:4,3-b']dipyrrol-3(2H)-yl]carbonyl]-1H-indol-5-yl]amino]carbonyl]-1H-indol (Cpd JJ, Part A) is dissolved in 200 ul DMA in the dark with stirring under nitrogen. To this is added 7 mg (0.047 mmole) of S-acetyl-thiolactic acid (Chem. Ber. 1966, 99, 1523, 1528) and 10 mg (0.053 mmole) of EDC. The mixture is left to react for 18 hrs and 3 mg more of EDC is added. The reaction is stirred for an additional 5 hrs.

The reaction mixture is then coated on 500 mg silica gel and chromatographed over 5 mg silica gel, eluted with 20% DMF-80% toluene, to give 17 mg solid, which by NMR appears to be a 1:1 mixture of product and starting acid.

The impure product is chromatographed over 1.5 g reverse phase C18 silica gel, and eluted with 70% DMF-30% water to give 8 mg of product.

NMR and HPLC of the product shows an impurity (12%) which could be increased on treatment with acetonitrile-water-triethylamine and which shows the appearance of a new UV peak at 364 nm, the impurity being the cyclopropyl compound, formed during the chromatography.

TLC: UV visualization; reverse phase C18 silica gel, 75% DMF-25% water, Rf 0.44; regular silica gel, 20% DMF-80% toluene, Rf 0.38.

HPLC: Altex Ultrashere, 1.5 ml/minute, 295 nm, 55% acetonitrile-45% water-0.1% TFA; two major peaks adding up to more than 95%, with the following retention times and percentages: 3.49 minutes, 12.4%; 6.38 minutes, 87.6%.

UV(MeOH): 324 nm (35,047).

Mass spectrum: M+H at 683,685; other ions at 705, 682, 669, 647, 447, 405, 187.

Part C: Hydrolysis of thioacetate and cyclopropyl ring closing of Part B.

A sample of Part B is stirred at RT in the dark and under nitrogen in acetonitrile-water-triethylamine. The reaction mixture is diluted with ethyl acetate-water which has been purged with nitrogen and keeping everything under nitrogen the layers are separated, the organic layer dried over sodium sulfate and evaporated to yield 5-[(2-mercaptopropionyl)amino]-N-[2-(4,5,8,8a-tetrahydro-7-methyl-4-oxocyclopropa[c]pyrrol[3,2-e]indol-2((1H)-yl)-1H-indol-5-yl]-1H-indole-2-carboxamide (Cpd #8).

UV: Acetonitrile-water-triethylamine; 318 nm, 28,410; 364 nm; 22,860.

EXAMPLE 10

Preparation of (S)-N-[2-[[1-(chloromethyl)-1,6-dihydro-8-methyl-5-[[[[4-[[(phenylmethyl)oxy]carbonyl]phenyl]amino]carbonyl]oxy]benzo[1,2-b:4,3-b']dipyrrol-3(2H)-2-yl]carbonyl]-1H-indol-5-yl]-2-benzofurancarboxamide (Cpd #10).

A 5 ml solution of phosgene (20% in toluene, 1.93 molar, 9.65 mmoles) is stirred at room temperature (~25° C.) under nitrogen. To this is added slowly from a syringe 48 mg (0.21 mmoles) of the compound of Formula S (General Formulae Chart) dissolves in 1 ml EtOAc. Some solid is formed at first which dissolves during the one hour reaction time. The reaction is then evaporated under vacuum, high vacuum at end.

The residue is stirred at room temperature (~25° C.) under nitrogen in 1 ml freshly distilled THF. To this is added slowly from a syringe 57 mg (0.105 mmoles) (S)-N-[2-[[1-(chloromethyl)-1,6-dihydro-5hydroxy-8-methylbenzo[1,2-b:4,3-b']dipyrrol-3(2H)-yl]carbonyl]-1H-indol-5-yl]-2-benzofurancarboxamide (see U.S. Pat. No. 4,912,227, Chart IV), in 1 ml freshly distilled THF and 14 ul triethylamine. The reaction mixture is heated to 65° C. for 2.5 hours when TLC shows the reaction to be complete.

The reaction mixture is cooled to room temperature (~25° C.), coated on 1 g silica gel and chromatographed over 9 g silica gel. Elute with a gradient of 40% acetone-60% hexane to 50% acetone-50% hexane. Fractions of 2 ml are collected, analyzing them by TLC. The product is found in fractions 17–45, which upon combining and evaporating leave 68 mg, 82% yield based on (S)-N-[2-[[1-(chloromethyl)-1,6-dihydro-5-hydroxy-8-methylbenzo[1,2-b:4,3-b']dipyrrol-3(2HO-yl]carbonyl]-1H-indol-5-yl]-2-benzofurancarboxamide (see U.S. Pat. No. 4,912,227, Chart IV).

TLC: UV visualization; silica gel; 40% acetone-60% hexane; Rf: 0.42 UV(MeOH): 285 nm (46,740); sh 325 mn (30,100). NMR(d$_6$-DMSO, TMS): δ 2.43 (s, 1H); 3.70–3.83 (t, 1H); 3.95–4.07 (d, 1H); 4.15–4.27 (t, 1H); 4.62–4.71(d, 1H); 4.72–4.84 (t, 1H); 5.35 (s, 2H); 7.21 (s, 1H); 7.2 (s, 1H);; 7.33–7.57 (m, 8H); 7.63–7.66 (d, 1H); 7.70–7.78 (m, 3H); 7.80 (s, 1H); 7.83–7.85 (d, 1H); 7.98 (bs, 1H); 8.01 (s, 1H); 8.04 (s, 1H); 8.28 (s, 1H); 10.52 (s, 1H); 10.83 (s, 1H); 11.29 (s, 1H); 11.77 (s, 1H).

Mass spectrum: Major ions at 794, 792, 684, 538, 303, 237, 236, 199, 187, 145, 91.

EXAMPLE 11A

Part A: Preparation of Hydrazide.

A 200 mg quantity (0.86 mmoles) of impure acid (Formula T, General Formulae Chart) is stirred at RT under nitrogen in 5 ml dry DMF. To the solution is added 165 mg (0.86 mmoles) EDC and 114 mg (0.86 mmoles) t-butylcarbazate giving a complete solution.

After 24 hrs the reaction mixture is partitioned between ethyl acetate-water. The layers are separated and the water layer reextracted with ethyl acetate. The organic layers are combined, dried over sodium sulfate and evaporated under vacuum. The residue is coated on 3 g silica gel and chromatographed over 30 g silica gel, eluting with 40% ethyl acetate-60% hexane followed by 50% ethyl acetate-50% hexane. Fractions of 5 ml are collected analyzing them by TLC. Impure product is found in fractions 49–84 which are combined and evaporated. This material is rechromatographed three times over 5 g silica gel, eluting with 30% acetone-70% hexane, separating out pure product (Formula U, General Formulae Chart) each time to give a total of 13 mg, 44% yield.

TLC: silica gel; UV visualization; 50% ethyl acetate-50% hexane; Rf: 0.42. Mass spectrum: Major ions at 424, 348, 292, 248, 216, 202, 57. NMR($d_6$-acetone, TMS): δ 1.33–1.43 (t, 3H); 1.46 (s, 9H); 4.33–4.46 (q, 2H); 7.30 (s, 1H); 7.59 (s, 1H); 7.62 (s, 1H); 7.87 (s, 1H); 7.90 (s, 1H); 7.97 (bs, 1H); 8.35 (s, 1H); 9.43 (bs, 1H); 11.24 (bs, 1H).

Part B: Ethyl ester hydrolysis.

A 100mg (0.29 mmoles) quantity ethyl ester is (Formula U) stirred at room temperature under nitrogen in 2 ml MeOH— 1 ml 1N NaOH— 1 ml water for 5 hours, when TLC shows the reaction not quite complete. At this point 0.5 ml 1N HCl is added and the reaction allowed to stand.

After 16 hrs TLC shows the reaction to be finished. The reaction mixture is partitioned between ethyl acetate-water. TLC shows the ethyl acetate layer to contain impurity only and is discarded. The water layer is acidified with 1 ml 1N HCl and extracted twice with ethyl acetate. No product is left in the water layer as seen by TLC. The organic layers are combined, dried over sodium sulfate and evaporated under vacuum. This leaves 85 mg (Formula V, General Formulae Chart), 92% yield.

TLC: silica gel; UV visualization; 50% ethyl acetate-50% hexane-2% acetic acid; Rf: 0.28. Mass spectrum: major ions at: 474, 396, 320, 264, 220, 188, 57. UV(EtOH): 210 nm (11,230); 252 nm (48,600); 305 nm (10,760); 315 nm, sl sh (8,470). NMR ($d_6$-DMSO, TMS): δ 1.44 (s, 9H); 7.21 (s, 1H); 7.46, 7.49 (d, 1H); 7.75, 7.77 (d, 1H); 8.25 (s, 1H); 8.88 (s, 1H); 10.12 (s, 1H); 12.07 (s, 1H); 12.9–13.3 (bs, 1H).

Part C: Amide preparation.

An 85 mg (0.27 mmoles) quantity acid (Formula V) is stirred at RT under nitrogen in the dark in 1 ml dry DMF. To this is added 55 mg (0.27 mmoles) amine (Formula G, General Formulae Chart) and 52 mg (0.27 mmoles) EDC and the mixture allowed to react for 3 days. TLC at this time indicates incomplete reaction and another 10 mg EDC is added and reaction continued for 2 days at which point the reaction appears to be complete.

The crude reaction mixture is coated on 1 g silica gel and chromatographed over 15 g silica gel, eluting with a gradient of 10-90 to 20-80 DMF-toluene to give 138 mg of product (Formula X, General Formulae Chart).

TLC: silica gel; UV visualization; 10% DMF-90% toluene; Rf: 0.28. Mass spectrum: major ions at 506, 406, 374, 302, 57. NMR ($d_6$-DMSO, TMS): δ 1.30–1.41 (t, 3H); 1.46 (s, 9H); 4.30–4.43 (q, 2H); 7.22 (s, 1H); 7.50–7.74 (m, 4H); 7.77–7.87 (d, 1H); 8.24 (s, 1H); 8.35 (s, 1H); 8.94 (s, 1H); 10.19 (s, 1H); 10.33 (s, 1H); 11.94 (s, 1H); 12.08 (s, 1H).

Part D: Ester hydrolysis.

A 138 mg (0.27 mmole) quantity ethyl ester (Formula X) is dissolved in 2 ml freshly distilled THF with stirring at RT under nitrogen. To this is added 1 ml EtOH and 1 ml 1N NaOH. Reaction is allowed to proceed for 21 hours when TLC shows it to be complete.

The reaction mixture is treated with 1 ml 1N HCl and evaporated under vacuum. The residue is treated with 20 ml water containing 1 ml 1N HCl. The resultant suspension is transferred to a centrifugation tube and spun down. The supernatant is decanted and the solid mixed with water. The suspension is again spun down and the liquid decanted. The solid is dried under vacuum, leaving 106 mg (Formula Y, General Formulae Chart), 82% yield.

TLC: silica gel; UV visualization; 20% DMF-80% toluene-2% HOAc; Rf: 0.32. Mass spectrum: major ions at 500, 478, 422, 346, 144, 57. NMR ($d_6$-DMSO, TMS): δ 1.45 (s, 9H); 7.09 (s, 1H); 7.40–7.61 (m, 4H); 7.73–7.78 (d, 1H); 8.16 (s, 1H); 8.27 (s, 1H); 8.86 (s, 1H); 10.11 (s, 1H); 10.29 (s, 1H); 11.73 (s, 1H); 12.05 (s, 1H).

Part E: Preparation of (S)-2-[[[2-[[1-(chloromethyl)-1,6-dihydro-5-hydroxy-8-methylbenzo[1,2-b:4,3-b']dipyrrol-3(2H)yl]-carbonyl]-1H-indol-5-yl]amino]carbonyl]-5-[[2-[[(1,1-dimethylethyl)oxy]carbonyl]hydrazino]carbonyl]-1H-indol (Cpd 11A).

A 57 mg (0.17 mmole) quantity of (S)-1-(chloromethyl)-1,6-dihydro-5-hydroxy-8-methyl-benzo[1,2b:4,3-b']dipyrrole-3(2H)-carboxylic acid 1,1-dimethyl ester (BOC chlorophenol) is stirred at RT in the dark and under nitrogen for one hour in 2 ml EtOAc and 3 ml EtOAc saturated with gaseous HCl. TLC in 30% ethyl acetate-70% hexane shows all of the starting material spot to have moved to the origin, indicating complete reaction. The reaction is then evaporated under vacuum, and the residue treated with methylene chloride md reevaporated under vacuum. The solid residue is dissolved in 1.5 ml DMA, giving a dark brown solution. To this is added 81 mg (0.17 mmoles) acid (Formula Y) and 32 mg EDC. The resultant mixture is stirred at RT under nitrogen in the dark for one hour, followed by the addition of 20 mg more acid and 8 mg more EDC and stirred for 3 more hours.

The reaction mixture is transferred to a centrifuge tube and the product precipitated with water. The solid is spun down and file liquid phase decanted. The cloudy liquid from decantation is extracted with EtOAc-THF. The organic layer is dried over sodium sulfate and evaporated under vacuum. The residue from this is combined with the solid from decantation.

The crude product is coated on 1 g silica gel and chromatographed over 13 g silica gel, eluting with 30% DMF-70% toluene to give 90 mg (76%) of product (Cpd #11A).

TLC: silica gel; UV visualization; 30% DMF-70% toluene; Rf: 0.47. NMR ($d_6$-DMSO, TMS): δ 1.45 (s, 9H); 2.37 (s, 3H); 3.55–3.68 (t, 1H); 3.87–3.97 (d, 1H); 4.00–4.10 (t, 1H); 4.51–4.60 (d, 1H); 4.63–4.77 (t, 1H); 7.06 (s, 1H); 7.16 (s, 1H); 7.46–7.83 (m, 6H); 8.25 (s, 1H); j8.31 (s, 1H); 8.91 (s, 1H); 9.83 (s, 1H); 10.15 (s, 1H); 10.30 (s, 1H); 10.76 (s, 1H); 11.71 (s, 1H); 12.08 (s, 1H). UV(MeOH): 319 nm (34,810); 293 nm (36,550). Mass spectrum: major ions at 772, 696, 695, 595, 564, 360, 237, 236, 199, 187, 170, 144,57.

EXAMPLE 11B

Preparation of (S)-2-[[[2-[[1-(chloromethyl)-1,6-dihydro-5-hydroxy-8-methylbenzo[1,2b:4,3-b']dipyrrol-3(2H)-yl]carbonyl]-1H-indol-5-yl]amino]carbonyl]-5-(hydrazinocarbonyl)-1H-indol monohydrochloride (Cpd #11B).

A 5.14 mg (0.0074 mmole) quantity of (S)-2-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[[2-[[(1,1dimelhylethyl)oxy]carbonyl]hydrazino]carbonyl]-1H-indol (Cpd #11A) is stirred at room temperature (~25° C.) under nitrogen in the dark with 2 ml ethyl acetate saturated with gaseous HCl for one hour. TLC in 20% DMF-80% toluene shows all of the starting material spot to move to the origin. The reaction mixture is evaporated under vacuum, and the residue treated with methylene chloride and reevaporated under high vacuum.

UV(MeOH): 320 nm (30,360); 293 nm (32,890). Mass spectrum: M+H at 596, 598; M at 595, 597. HPLC: Altex Ultrasphere C18; 1.5 ml/min; 295 nm; 40% acetonitrile-60% water-0.2% TFA; 98% pure; retention time: 5.13 min. NMR ($d_6$-DMSO, TMS): δ 2.36 (s, 3H); 3.56–3.70 (m, 1H); 3.85–3.96 (d, 1H); 3.98–4.10 (t, 1H); 4.50–4.60 (d, 1H); 4.62–4.75 (t, 1H); 7.06 (s, 1H); 7.15 (s, 1H); 7.47–7.54 (d, 1H); 7.55–7.73 (m, 4H); 7.77–7.87 (d, 1H); 8.24 (s, 1H); 8.38 (s, 1H); 9.77–9.90 (bs, 1H); 10.39 (s, 1H); 10.4–10.7 (bs, 2H); 10.78 (s, 1H); 11.46 (s, 1H); 11.72 (s, 1H); 12.25 (s, 1H).

EXAMPLE 12

Preparation of (S)-N-[2-[[1-(chloromethyl)-1,6-dihydro-8-methyl-5-[[[[4-[[2-[[(1,1dimethylethyl)oxy]carbonyl]hydrazino]carbonyl]phenyl]amino]carbonyl]oxy]benzo[1,2-b:4,3-b']dipyrrol-3(2H)-yl]carbonyl]-1H-indol-5-yl]-2-benzofurancarboxamide (Cpd #12);

Part A: BOC hydrazide.

A 500 mg (2.76 mmole) quantity 4-nitrobenzoic hydrazide is stirred at room temperature (~25° C.) under nitrogen in 5 ml freshly distilled THF. 680 mg (2.76 mmoles) of [2-(tert-butoxycarbonyloxyimino)-2-phenylacetonitrile] (BOC-ON) and 385 ul (2.76 mmoles) triethylamine are added. The resulting mixture is then treated with 3 ml more THF, followed by 2 ml DMF, stirred for 48 hours, then heated to 50° C. for 8 hrs, and allowed to proceed at room temperature (~25° C.) 16 additional hrs. The reaction is then condensed to about ½ volume by passing a stream of nitrogen above the liquid with heating to 50° C. Then 380 ul of triethylamine is added and the reaction allowed to stand for 4 days at room temperature (~25° C.). TLC shows almost complete reaction.

The reaction mixture is partitioned between methylene chloride-water. The layers are separated and the aqueous layer reextracted with ethyl acetate. The organic layers are combined, dried over sodium sulfate and evaporated under vacuum.

The crude product is coated on 10 g silica gel and chromatographed over 100 g silica gel, eluting with ethyl acetate-hexane: 300 ml , 20-80; 250 ml , 30-70; 250 ml , 40-60; 500 ml , 50-50; and 250 ml , 60-40 to give 661 mg (85%) of desired product (Compound Z in General Formulae Chart).

TLC: silica gel; UV visualization; 20% ethyl acetate-80% hexane; Rf: 0.14 IR(Mull): peaks at 2925, 1525, 1675, 3325, 3320, 2953, 1719, 3399, 1278, 2855. 1159, 1731, 1256, 1510, 2869, 1484, 1350, 1370, 1373, 606, 851, 3235, 2986, 1460, 1456. Mass spectrum: major ions at: 435, 282, 226, 182, 150, 57. UV (EtOH): 212 nm sh (8,460); 262 nm (11,850). NMR ($d_6$-acetone, TMS): δ 1.46 (s, 9H); 8.10–8.23 (d+s, 3H); 8.33–8.41 (d, 2H); 9.81 (s, 1H).

Part B: Preparation of Formula AA (General Formulae Chart) amine.

A 100 mg (0.35 mmole) quantity of Formula Z (General Formulae Chart) (Part A) compound is dissolved in 2 ml THF. To this is added 5 ml 95% EtOH and 20 mg platinum oxide. The mixture is hydrogenated at room temperature (~25° C.) under pressure for 50 minutes. The reaction mixture is filtered, washing the solid with ethanol. The combined filtrate and wash is evaporated under vacuum, leaving 87 mg solid (Formula A).

TLC: silica gel; UV visualization; 60% ethyl acetate-40% hexane; Rf: 0.47. NMR ($d_6$acetone, TMS): δ 1.43 (s, 9H); 5.17–5.3 (d, 2H); 6.65–6.72 (d, 2H); 7.65–7.74 (d, 2H); 7.77 (bs, 1H); 9.05 (bs, 1H). Mass spectrum: major ions at 252, 251, 196, 178, 120, 57. IR(Mull): peaks at 1719, 1631, 1607, 2925, 1274, 1518, 2954, 1487, 3356, 1259, 1167, 2855, 3239, 1182, 2869, 1371, 2981, 3374, 1306, 3438, 1463, 1460, 1574, 839, 779 $cm^{-1}$. UV(EtOH): 213 nm (11,800); 285 nm (16360).

Part C: Preparation of (S)-N-[2-[[1-(chloromethyl)-1,6-dihydro-8-methyl-5[[[[4-[[2-[[-( 1,1-dimethylethyl)oxy] carbonyl]hydrazino]carbonylphenyl]amino]carbonyl]oxy] benzo[1,2-b:4,3-b']dipyrrol-3(2H)-yl]carbonyl]-1H-indol-5-yl]-2-benzofurancarboxamide (Cpd #12).

A 4 ml quantity phosgene in toluene (20% , 1.93 molar) is stirred at room temperature (~25° C.) under nitrogen. To this is added 50 mg (0.20 mmoles) of the amine (Part B, Formula A), dissolved in 2 ml dry THF, by syringe during one minute. After 5 minutes, the reaction is still clear and 28 ul triethylamine is added. A precipitate forms. After 2 hrs another 28 ul triethylamine is added and reaction continued for 17 hours. A 100 ul aliquot is removed and evaporated under vacuum. The residue is dissolved in 0.5 ml THF and an IR spectrum run. An isocyanate peak is seen at 2250.

The remainder of the reaction mixture is evaporated under vacuum. The residue is stirred under nitrogen in 1 ml dry THF. To this is added 57 mg (S)-N-[2-[[1-(chloromethyl)-1,6-dihydro-5-hydroxy-8-methylbenzo[1,2-b:4,3-b'] dipyrrol-3(2H-yl]carbonyl]-1H-indol-5-yl]-2-benzofurancarboxamide (see U.S. Pat. No. 4,912,227, Chart IV), (0.106 mmoles) in 15 ul triethylamine and 2 ml dry THF. The resultant mixture is heated to 70° C. for one hour when another 10 ul triethylamine is added. Heating is continued for one hour more. The resultant mixture is cooled to room temperature (~25° C.) and the solid filtered off by washing it with THF. The combined filtrate and wash are evaporated under vacuum.

The residue is coated on 1 g silica gel and chromatographed over 10 g silica gel, eluting with 20% DMF-80% toluene to give a major product (71 mg of solid) which is still impure.

The impure product is coated on 1 g Celite and chromatographed over 7 g preparative C18 reverse phase silica gel (Waters, 55–105 microns). The column is eluted with 10 ml 60% acetone-40% water, followed by 70-30 of same to give 31 mg (36%) of product (Cpd #12).

TLC: silica gel; UV visualization; 10% DMF-90% toluene; Rf: 0.21 UV (MeOH): 330 nm (21,220); 280 nm (31,830). NMR ($d_6$-DMSO,TMS): δ 1.44 (s, 9H); 3.72–3.83 (t, 1H); 3.95–4.08 (d, 1H); 4.15–4.28 (t, 1H); 4.60–4.72 (d, 1H); 4.73-jj4.84 (t, 1H); 7.21 (s, 1H); 7.23 (s, 1H); 7.35–7.45 (t, 1H); 7.45–8.00 (m, 11H); 8.25 (s, 1H); k8.91 (s, 1H); 10.13 (s, 1H); 10.52 (s, 1H); 10.73 (s, 1H); 11.28 (s, 1H); 11.76 (s, 1H). Mass spectrum: major ions at 819, 818, 817, 816, 684, 538, 303, 237, 236, 199, 187, 177, 145, 120, 57.

EXAMPLE 13

Preparation of (S)-N-[2-[[1-(chloromethyl)-1,6-dihydro-8-methyl-5-[[[[4-[[[2-[[(1,1-dimethylethyl)oxy]carbonyl]hydrazino]carbonyl]ethyl]phenyl]amino]carbonyl]oxy]

benzo[1,2-b:4,3-b']dipyrrol-3(2H)-yl]carbonyl]-1H-indol-5-yl]-2-benzofurancarboxamide (Cpd #13).

Part A: Ester hydrolysis.

A 2 g quantity of p-nitro ethyl cinnamate (9.04 mmoles) is stirred at room temperature (~25° C.) under nitrogen in 20 ml THF-10 ml MeOH-20 ml 1N NaOH for 30 minutes at which time everything has gone into solution and TLC shows no staffing material left.

A 20 ml volume of 1N HCl is then added resulting in the precipitation of a solid. The solid (Formula BB, General Formulae Chart), is collected by filtration and dried under vacuum to give Crop 1: 1.58 g, 90% yield. The filtrate is concentrated under vacuum and a second crop is obtained: 40 mg, 2% yield. Total yield 92%.

TLC: silica gel; UV visualization; 50% EtOAc-50% hexane; Rf: origin. IR (Mull): peaks at 1351, 1687, 2924, 1532, 1631, 1521, 1343, 849, 1310, 2953, 2855, 2869, 1622, 1429, 988, 717, 1321, 1285, 1606, 1597, 713, 961, 1497, 760, 3054 $cm^{-1}$. UV (EtOH): 211 nm, sh(14,690); 222 nm, sh(10,130); 302 nm (18,930). Mass spectrum: ions at 193, 176, 147, 146, 102, 91, 77.

Part B: Preparation of Formula CC (General Formulae Chart).

A 0.5 g quantity (2.6 mmoles) of Formula BB (Part A) acid is stirred at room temperature (~25° C.) under nitrogen in 10 ml dry DMF, resulting in a partial solution. To this is added 396 mg (3 mmoles) of t-butylcarbazate and 575 mg (3 mmoles) of EDC. The mixture is left to react for 1.5 hours, during which time everything dissolves. Another 192 mg of EDC is added and the reaction allowed to continue for 3.5 days.

At this time the reaction mixture is partitioned between ethyl acetate-water. The layers are separated and the water layer reextracted with ethyl acetate. The organic layers are combined, dried over sodium sulfate and evaporated under vacuum. The crude product is coated on 10 g silica gel and chromatographed over 100 g silica gel. The column is eluted with a gradient of 40-60 to 60-40 ethyl acetate-hexane, giving 623 mg of product (Formula CC) as a solid, 78% yield.

TLC: silica gel; UV visualization; 50% ethyl acetate-50% hexane; Rf: 0.72 IR(Mull): peaks at 1515, 2925, 1675, 1348, 2954, 3299, 1715, 2855, 1252, 1637, 1367, 2867, 1166, 1297, 3218, 1282, 1373, 1149, 1543, 835, 1456, 989, 1594, 848, 719 $cm^{-1}$. UV(EtOH): 212 nm (15400); 223 nm sh(11400); 244 nm sh(13100); 307 nm, 22440. Mass spectrum; peaks at 307, 251, 234, 207, 176, 57.

Part C: Preparation of Formula DD (General Formulae Chart).

A 200 mg (0.65 mmole) quantity of Formula CC (Part B) is dissolved in 4ml freshly distilled THF. To this is added 10 ml 95% EtOH and 40 mg platinum oxide and the mixture hydrogenated at room temperature (~25° C.) under pressure for 45 minutes. The reaction mixture is filtered, washing the solid with THF. The combined filtrate and wash is evaporated under vacuum, treated with toluene and reevaporated twice, leaving 201 mg, 100% yield of product (Formula DD).

TLC: silica gel; UV visualization; 50% ethyl acetate-50% hexane; Rf: 0.31 NMR (CDCl3, TMS): δ 1.46 (s, 9H); 2.40–2.5 (t, 2H); 2.80–2.90 (t, 2H); 3.59 (bs, 2H); 3.59 (bs, 2H); 6.58–6.64 (d, 2H); 6.92–7.00 (d, 2H). Mass spectrum: major ions at 559, 279, 224, 180, 106, 57. IR(Mull): major peaks at 2926, 2955, 2856, 1672, 1730, 1519, 1168, 2868, 1237, 1715, 1368, 3285, 1456, 1466, 1272, 1258, 1484, 1288, 1298, 3327, 1393, 1617, 1632, 831, 3389 $cm^{-1}$. UV(EtOH): 238 nm (9580); 290 nm (1360).

Part D: Preparation of (S)-N-[2-[[1-(chloromethyl)-1,6-dihydro-8-methyl-5-[[[[4-[[[2-[[(1,1-dimethylethyl)oxy]carbonyl]hydrazino]carbonyl]ethyl]phenyl]amino]carbonyl]oxy]benzo[1,2-b:4,3-b']dipyrrol-3(2H)-yl]carbonyl]-1H-indol-5-yl]-2-benzofurancarboxamide (Cpd #13).

A 1 ml quantity phosgene in toluene (20%, 1.93 molar) is stirred at room temperature (~25° C.) under nitrogen. A total of 50 mg (0.18 mmoles) of Formula DD (Part C) amine dissolved in 80 ul triethylamine and 1 ml dry THF is added over 1 minute via syringe. The reaction is stirred for 5 hrs whereupon another 50 ul of triethylamine is added and the reaction stirred another hour. The reaction is then evaporated under reduced pressure.

The residue is then stirred under nitrogen in 2 ml dry THF, giving a suspension. To this is added 30 mg (0.056 mmoles) (S)-N-[2-[[1-(chloromethyl)-1,6-dihydro-5-hydroxy-8-methylbenzo[1,2-b:4,3-b']dipyrrol-3(2H-yl]carbonyl]-1H-indol-5-yl]-2-benzofurancarboxamide (see U.S. Pat. No. 4,912,227, Chart IV), dissolved in 1 ml dry THF and 10 ul triethylamine. The mixture is heated to 70° C. for two hours, when 5 ul more triethylamine is added. The reaction is then cooled to room temperature (~25° C.) and allowed to proceed. After 16 hr the reaction is reheated to 70° C. for 2 hours more and again cooled to room temperature (~25° C.).

The crude product is coated on 1 g silica gel and chromatographed over 10 g silica gel, eluting with a gradient of 5% DMF-95% toluene to 10% DMF-90% toluene to give impure product. This material is coated on 1 g Celite and chromatographed over 10 g reverse phase C18 silica gel (waters, 55–105 microns). The column is made up in acetone and conditioned with 10 ml each of 90-10, 80-20, 70-30, and 60-40 acetone-water. The product is then eluted with 10 ml 60% acetone-40% water, 100 ml 70-30 and 20 ml 80-20 of the same solvents to give 28 mg (60%) of pure product (Compound 13).

TLC: silica gel; UV visualization; 10% DMF-90% toluene; Rf: 0.53 UV(MeOH): 320 nm (41,370); 292 nm (54,030). NMR ($d_6$-acetone, TMS): δ 1.57 (s, 9H); 2.44 (s, 3H); 2.83–3.05 (m, 6H); 3.67–3.77 (t, 1H); 3.96–4.04 (dd, 1H); 4.18–4.28 (t, 1H); 4.73–4.87 (m, 2H); 7.11 (s, 1H); 7.23 (s, 1H); 7.28 (s, 1H); 7.31 (s, 1H); 7.33–7.41 (t, 1H); 7.46–7.54 (t, 1H); 7.54–7.70 (m, 6H); 7.77–7.83 (d, 1H); 8.14 (s, 1H); 8.42 (s, 1H); 9.30 (s, 1H); 9.69 (s, 1H); 10.47 (s, 1H); 10.98 (s, 1H); Mass spectrum: major ions at 844, 770, 539, 538, 303, 237, 236, 199, 187, 145, 73, 57.

EXAMPLE 14

Preparation of (S)-N-[2-[[1-(chloromethyl)-1,6-dihydro-8-methyl-5-[[[[4-[2-[(hydrazinocarbonyl)ethyl]phenyl]amino]carbonyl]oxy]benzo[1,2-b:4,3-b']dipyrrol-3(2H)-yl]carbonyl]1H-indol-5-yl]-2-Benzofurancarboxamide, monohydrochloride (Cpd #14).

A 5.32 mg (0.0063 mmole) quantity of (S)-N-[2-[[1-(chloromethyl)-1,6-dihydro-8-methyl-5-[[[[4-[[[2-[[(1,1-dimethylethyl)oxy]carbonyl]hydrazino]carbonyl]ethyl]phenyl]amino]carbonyl]oxy]benzo[1,2-b:4,3-b']dipyrrol-3 (2H)-yl]carbonyl]-1H-indol-5-yl]-2-benzofurancarboxamide (Cpd #13), is stirred at room temperature (~25° C.) in the dark under nitrogen in 2 ml ethyl acetate saturated with gaseous HCl for one hour. TLC in 20% DMF-80% toluene shows all of the starting material spot to have moved to the origin. The solvent is evaporated under vacuum. The residue is extracted with methylene chloride and reevaporated under high vacuum to give Compound 14.

UV(MeOH): 320 nm (31,230); 292 nm (39,420). HPLC: Altex Ultrasphere C18; 1.5 ml/min; 295 nm; 55% acetonitrile-45% water-0.2% TFA; 91% pure; retention time: 10.22 min. NMR (DMSO, TMS): δ 2.42 (s, 3H); 2.76–2.93 (m, 4H); 3.70–3.82 (t, 1H); 3.96–4.05 (d, 1H); 4.13–4.25 (t, 1H); 4.58–4.67 (d, 1H); 4.70–4.84 (t, 1H); 7.15–7.25 (m, 4H); 7.34–7.43 (t, 1H); 7.43–7.54 (m, 4H); 7.55–7.64 (d, 1H); 7.70–7.93 (m, 4H); 8.23 (s, 1H); 10.33 (s, 1H); 10.51 (s, 1H); 11.22 (s, 1H); 11.75 (s, 1H); 12.07 (s, 1H).

EXAMPLE 15

Preparation of (S)-[[[2-[[1-(chloromethyl)-1,6-dihydro-5-hydroxy-8-methylbenzo[1,2-b:4,3-b']dipyrrol-3(2H)-yl] carbonyl]1H-indol-5-yl]amino]carbonyl]-5-[2-[[2-[[(1,1-dimethylethyl)oxy]carbonyl]hydrazino]carbonyl]ethyl]-2-Benzofuran (Cpd #15).

Part A: Preparation of 3-[(benzofuran-2-carboethoxy)-5-yl]-propenoic acid.

A mixture of 5-bromobenzofuran-2-carboxylic acid ethyl ester (0.76 mM), palladium acetate (0.14 mM), triphenylphosphine (0.31 mM), acrylic acid (7.3 mM), distilled triethylamine (14.3 mM) and dimethylformamide (0.3 ml) is heated under argon at 110° C. for 1.5 hours. The reaction is cooled and partitioned between 1N HCl and ethyl acetate. The acidic product is extracted into 5% sodium bicarbonate solution.

Acidification and extraction of the bicarbonate solution gives after drying and concentration 279 mg of crude yellow solid. The product is chromatographed on reversed phase C18 silica in methanol-water-acetic acid mixtures. A 20% yield of desired product is obtained.

NMR (d$_4$-MeOH, TMS): δ 1.41 (t, 3H); 4.41 (q, 2H); 6.53 (d, 1H, J=18 hz); 7.62 (m, 2H); 7.76 (m, 2H); 7.99 (s, 1H). C-13 NMR (DMSO-d$_6$, TMS): δ 14.15, 61.43, 112.80, 114.19, 119.32, 123.66, 127.24, 127.75, 130.68, 143.49, 146.08, 155.89, 158.54, 167.69. MS(EI): M+. at m/z 260; major ions at m/z 232, 215, 188, 159. TLC(RP C18 silica): Rf=0.28 in (70-30-0.2) methanol-water-acetic acid.

Part B: Preparation of 3-(5-benzofuran-2-carboethoxy)-propanoic acid.

The olefin of Part A (0.18 mM) is dissolved in THF (1 ml) and methanol (1 ml). The resultant solution is treated with 10% palladium on carbon (36 mg). Four aliquots of ammonium formate (approximately 50 mg each) are added over the course of 3.8 hrs. The reaction is filtered, and the solids washed with methanol. The filtrate is evaporated, redissolved in ethyl acetate, and washed with water and brine. The ethyl acetate solution is dried over anhydrous sodium sulfate and evaporated. An 82% yield of desired product is obtained. Mp 96°–108° C.

NMR (d$_4$-MeOH, TMS): δ 1.40 (t, 3H); 2.64 (t, 2H); 3.02 (t, 2H); 4.40 (q, 2H); 7.37 (dd, 1H); 7.55 (m, 3H). C-13NMR (d$_4$-MeOH, TMS): δ 14.60, 31.87, 37.15, 62.57, 112.81, 114.78, 123.20, 128.50, 129.72, 138.19, 147.13, 155.92, 161.02, 176.69. MS(EI): M+. at m/262. Other ions at m/z 217, 203, 175, 115. TLC (Silica gel GF, acetic acid washed): Rf=0.55 in (20-80) ethyl acetate-toluene.

Part C: Coupling of Propanoic acid-3-(5-benzofuran-2-carboethoxy) with t-butyl carbazate.

The acid of Part B (0.14 mM) is dissolved in N,N-dimethylacetamide (0.5 ml) is treated with tert-butyl carbazate (0.28 mM). Approximately one half of a weighed quantity of 1-ethyl-3-(3-dimethylaminopropyl)carbodiimide hydrochloride (EDC, 0.32 mM) is added to the reaction and it is stirred at room temperature (~25° C.) for 1.3 h. The remainder of the EDC is added and stirring is continued overnight. The reaction is partitioned between ethyl acetate and water. The organic layer is washed with 0.1N HCl and brine, dried and evaporated. The crude product is chromatographed on 5 g HPLC grade silica in ethyl acetate-toluene mixtures. An 83% yield of product (Formula EE, General Formulae Chart) is realized.

NMR (CDCl$_3$, TMS): δ 1.42 (s+t, 12H); 2.57 (t, 2H); 3.06 (t, 2H); 4.43 (q, 2H); 6.82 (bs, 1H); 7.26 (dd, 1H); 7.45 (m, 3H); 8.16 (bs, 1H). C-13 NMR (CDCl$_3$, TMS): δ 14.18, 27.96, 30.81, 35.82, 61.39, 81.73, 112.10, 113.51, 121.90, 127.03, 128.19, 136.03, 145.78, 154.39, 155.67, 159.48, 171.60. MS(CI): M+. at m/z 376. Other ions at m/z 276, 203, 175, 57. TLC(Silica gel GF): Rf=0.08 in (20-80) ethyl acetate-toluene.

Part D: Hydrolysis of Ethyl Ester.

The product of Part C (Formula EE, 0.11 mM) is stirred in a mixture of pyridine (1 ml) and 1N NaOH (0.25 ml) at room temperature (~25° C.) for 4 h. The reaction is diluted with 1N HCl and ethyl acetate. The ethyl acetate layer is dried and evaporated to give a white solid of Formula FF (93% yield) which is used in the next reaction without further purification.

NMR (MeOH-d$_4$, CDCl$_3$, TMS): δ 1.47 (s, 9H); 2.57 (t, 2H); 3.07 (t, 2H); 7.33 (dd, 1H); 7.50 (m, 4H).

Part E: Coupling of 5-Amino-2-carboxyethyl-benzofuran with 5-Aminoindole-2-Carboxylic Acid Ethyl Ester.

A mixture of the acid (Formula FF, General Formulae Chart) (0.10 mM), the (Formula GG) amine (0.13 mM), and EDC (0.15 mM) in N,N-dimethylacetamide (0.2 ml) is stirred at room temperature (~25° C.) in subdued light for 4 days. The reaction is partitioned between ethyl acetate and water. The ethyl acetate layer is washed with brine, dried and evaporated. The crude product is purified chromatographically on HPLC grade silica gel in ethyl acetate-toluene mixtures. A 72% yield of white solid product (Formula HH, General Formulae Chart) is obtained. Mp 132°–135° C.

NMR (CDCl$_3$, MeOH-d$_4$, TMS): δ 1.44 (t, 3H); 1.48 (s, 9H); 2.59 (t, 2H); 3.09 (t, 2H); 4.41 (q, 2H); 7.18–7.45 (m, 7H); 8.17 (s, 1H). C-13 NMR (CDCl$_3$, MeOH-d$_4$, TMS): δ 15.35, 29.16, 32.39, 37.16, 62.29, 82.51, 109.87, 112.14, 113.01, 113.84, 115.86, 121.62, 123.17, 128.56, 129.19, 129.79, 131.56, 136.65, 137.77, 150.31, 155.31, 157.63, 159.26, 163.73, 174.59. MS(FAB): {m+H}+at m/z 535; other ions at m/z 479,435, 361. TLC(Silica gel GF): Rf=0.20 in (30-70) ethyl acetate-toluene.

Part F: Ester Hydrolysis.

A solution of the ester (Formula HH, General Formulae Chart), (0.07 mM) in pyridine (1 ml) and 1N NaOH (0.3 ml) is stirred at room temperature (~25° C.) for 18 hours. The reaction is acidified with 1N HCl and extracted with ethyl acetate. Drying and concentration of the ethyl acetate solution gives 38 mg of white solid product. It is used in the next step without further purification.

NMR (DMF-d$_7$ TMS): δ 1.43 (s, 9H); 2.58 (t, 2H); 3.05 (t, 2H); 7.19 (s, 1H); 7.43 (d, 1H); 7.56 (m, 2H); 7.71 (m, 2H); 7.79 (dd, 1H); 8.37 (s, 1H); 8.72 (bs, 1H); 9.64 (bs, 1H); 10.55 (bs, 1H); 11.78 (bs, 1H).

Part G: Preparation of (S)-[[[2-[[1-(chloromethyl)-1,6-dihydro-5-hydroxy-8-methylbenzo[1,2-b:4,3-b']dipyrrol-3 (2H)-yl]carbonyl]-1H-indol-5-yl]-amino]carbonyl]-5-[2-[ [2-[[(1,1-dimethylethyl)oxy]carbonyl]hydrazino]carbonyl] ethyl]2-benzofuran (Cpd #15).

Hydrogen chloride is bubbled into an ethyl acetate for approximately 20 minutes. (S)-1-(chloromethyl)-1,6-dihydro-5-hydroxy-8-methyl-benzo[1,2b:4,3-b']dipyrrole-3 (2H)-carboxylic acid 1,1-dimethyl ester BOC(CPI) chlorophenol (0.105 mM) in ethyl acetate (0.5 ml) is treated with 1 ml of the above HCl solution. The reaction is stirred at room temperature (~25° C.) under an inert atmosphere for 45 minutes. The reaction is evaporated under reduced pressure to dryness. Contact of the product with air is avoided. The residue is treated with methylene chloride and re-evaporated twice. A solution of the acid of Part F, (0.075 mM) in N,N-dimethylacetamide (1 ml) is added to the residue followed by approximately one-half of a weighed quantity of EDC (0.19 mM).

After the reaction has been stirred for one hr at room temperature (~25° C.), the remainder of the EDC is added. One hour later, the reaction is diluted with ethyl acetate and washed with water. The organic layer is dried over anhydrous sodium sulfate and evaporated. The residue is adsorbed onto silica gel (1 g) and flash chromatographed on HPLC grade silica gel (7 g) in (20-80) and (30-70) dimethylformamidetoluene to give 72% of a yellow solid product.

NMR (DMSO-$d_6$) $\delta$ 1.41 (s, 9H); 2.36 (s, 3H); 2.45 (t, 2H); 2.96 (t, 2H); 3.61 (t, 1H); 3.91 (m, 1H); 4.04 (m, 1H); 4.53 (m, 1H); 4.67 (m, 1H); 7.05 (s, 1H); 7.14 (s, 1H); 7.37 (d, 1H); 7.47 (d, 1H); 7.62 (m, 5H); 8.20 (s, 1H); 8.73 (bs, 1H); 9.58 (bs, 1H); 9.79 (s, 1H); 10.45 (s, 1H); 10.73 (bs, 1H); 11.69 (bs, 1H). MS(FAB): Calc'd for C38H37ClN6O7: 724.2412; measured: 724.2393. Major ions at m/z 625, 389, 357, 347, 236, 199. UV(DMA, MeOH): emax 294 (36000), shoulder at 335 (22000). TLC(Silica gel GF): Rf=0.45 in (30-70) DMF-toluene.

EXAMPLE 16

Preparation of (S)-2-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-(hydrazinocarbonyl)ethyl]-2-benzofuran monohydrochloride (Cpd #16).

Removal of t-BOC Protecting Group (S)-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]-amino]carbonyl]-5-[2-[[2-[(1,1-dimethylethyl)oxy]-carbonyl]hydrazino]carbonyl]ethyl]-2-benzofuran (Cpd #15), (3 mg, 4.1×10$^{-6}$ mmole) is dissolved in a minimal amount of dimethylformamide. The solution is treated with 1 ml of HCl-saturated ethyl acetate and stirred in subdued light at room temperature (~25° C.) for 20 minutes. The solvent is then removed under vacuum to give (S)-[[[2-[[1-(chloromethyl)-1,6dihydro-5-hydroxy-8-methylbenzo[1,2-b:4,3-b']dipyrrol-3(2H)-yl]carbonyl]-1H-indol-5-yl]amino]carbonyl-5-[2-(hydrazinocarbonyl)ethyl]-2-benzofuran monohydrochloride (Cpd #16), as a solid.

NMR (DMSO-$d_6$, TMS): $\delta$ 2.36 (s, 3H); 2.60 (t, 2H); 3.00 (t, 2H); 3.60 (t, 1H); 3.92 (d, 1H); 4.03 (dd, 1H); 4.53 (d, 1H); 4.68 (t, 1H); 7.05 (s, 1H); 7.13 (s, 1H); 7.39 (d, 1H); 7.48 (d, 1H); 7.64 (m, 5H); 7.73 (s, 1H); 8.20 (s, 1H); 9.79 (s, 1H); 10.46 (s, 1H); 10.62 (bs, 1H); 10.74 (s, 1H); 11.69 (s, 1H). HPLC (Altex Ultrashere ODS, 51μ C18 column, 4.6×150 mm; 295mn detection; Solvents: 40% CH$_3$CN+ 0.2% TFA: 60% H$_2$O+0.2% TFA; pump rate 1.5 ml/min): Retention time=8.19 min.

EXAMPLE 17

Preparation of (7bR)-N-[2-[[4,5,8,8a-tetrahydro-7-methyl-4-oxocyclopropa[c]pyrrolo[3,2-e]indol-2(1H)-yl]carbonyl]-1H-indol-5-yl]aminocarbonyl]-5-[2-[[2-[(1,1-dimethylethyl)oxy]carbonyl]hydrazino]carbonyl]ethyl]-2-benzofuran (Cpd #17).

A 50 mg (0.069 mmole) quantity of (S)-[[[-2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-[[(1,1-dimethylethyl)oxy]carbonyl]hydrazino]carbonyl]ethyl]-2-benzofuran (Cpd #15) is treated with 10 ml of (25-25-50) triethyl amine-acetonitrile-water and the resultant solution stirred at 25° C. for 25 min. The reaction mixture is then partitioned between THF, ethyl acetate and water. The water layer is separated and reextracted with THF-ethyl acetate. The combined organic extracts are dried over sodium sulfate. To this solution is added 500 mg of silica gel and then the mixture concentrated under vacuum. The residue is added to the top of a 5 g silica gel column and the column eluted with (20-80) DMF-toluene, collecting 2 ml fractions. The fractions containing product as determined by TLC (19-28) are combined and evaporated under vacuum leaving 37 mg of (7bR)-N-[2-[[4,5,8,8a-tetrahydro-7-methyl-4-oxocyclopropa[c]pyrrolo[3,2-e]indol-2(1H)-yl-carbonyl]-1H-indol-5-yl]aminocarbonyl]-5-[2-[[2-[(1,1-dimethylethyl)oxy]carbonyl]hydra-zino]carbonyl]ethyl-2-benzofuran.

NMR (DMSO-$d_6$): $\delta$ 1.32 (s, 1H); 1.41 (s, 9H); 1.90–2.04 (m, 1H); 2.01 (s, 3H); 2.38–2.52 (t, 2H); 2.90–3.02 (t, 2H); 3.12–3.23 (m, 1H); 4.41–4.51 (d, 1H); 4.52–6.90 (s, 1H); 7.22 (s, 1H); 7.33–7.41 (dd, 1H); 7.44–7.51 (d, 1H); 7.62 (s, 1H); 7.65 (s, 1H); 7.70 (s, 1H); 8.22 (s, 1H); 8.75 (s, 1H); 9.59 (s, 1H); 10.48 (s, 1H); 11.56 (s, 1H); 11.56 (s, 1H); 11.83 (s, 1H). TLC: R$_f$=0.36 in (20-80) DMF-toluene.

EXAMPLE 18

Preparation of (S)-[[[2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-[[2-[[(1,1-dimethylethyl)oxy]carbonyl]hydrazino]carbonyl]ethyl]-2-benzofuran 3,6,9-trioxadecanoic acid ester (Cpd #18).

Part A: Preparation of 3,6,9-trioxadecanoic acid (23899IG-154)

A 0.5 g quantity of platinum oxide is hydrogenated in 60 ml of water at 25° C. and atmospheric pressure until the uptake of hydrogen ceases. To the resultant mixture is added a mixture of 0.6 g (7.14 mmoles) of sodium bicarbonate and 1.0 g (6.1 mmoles) of triethylene glycol monomethyl ether dissolved in 20 mL of water. Air is bubbled through the above mixture for 4 hr following the consumption of staging material by TLC. The reaction is then filtered though Celite and the Celite washed with water. The combined washes are treated with 7.2 mL (7.2 mmoles) of 1N hydrochloric acid and the resultant solution freeze-dried. The residue is washed with acetone and filtered. The filtrate is evaporated to dryness under vacuum. The residual oil is chromatographed over 100 g of CC-4 silica gel eluted with (50-50) acetone-methylene chloride, collecting 20 mL fractions. Concentration of fractions 11–16 gives 0.92 g of the desired 3,6,9-trioxadecanoic acid.

NMR (acetone-$d_6$): $\delta$ 3.30 (s, 3H); 3.40–3.75 (m, 8H); 4.12 (s, 2H). TLC: R$_f$=0.13 in (40-60-2) acetone-hexane-acetic acid.

Part B:

A 40 mg (0.22 mmole) quantity of 3,6,9-trioxadecanoic acid (Part A) is treated with 0.5 mL of thionyl chloride and the mixture heated to reflux under a nitrogen atmosphere for 1 hr. The reaction is then cooled and concentrated under vacuum at 25° C. The residue is redissolved in carbon tetrachloride and again evaporated under vacuum. The residual acid chloride is treated with 1.0 mL of dry pyridine and this solution added to a solution of 30 mg (0.043 mmole) quantity of (7bR)-N-[2-[[4,5,8,8a-tetrahydro-7-methyl-4-oxocyclopropa[c]pyrrolo[3,2-e]indol-2(1H)-yl-carbonyl]-1H-indol-5-yl]aminocarbonyl]-5-[2-[[2-[(1,1-dimethylethyl)oxy]carbonyl]hydra-zino]carbonyl]ethyl-2-benzofuran (Cpd #17). After stirring 16 hr at 25° C., the reaction is treated with 0.3 mL of 5% aqueous sodium bicarbonate and the total mixture evaporated under vacuum onto 0.5 g of silica gel. The residual silica gel and compound are added to the top of a 7 g silica gel column which is then eluted with (15-85) DMF-toluene, collecting fractions of 2 mL. Evaporation of fractions 13–20 leaves 9 mg of (S)-[[[-2[[1-(chloromethyl)-1,6-dihydro-5-hydroxy-8-methylbenzo[1,2-b:4,3-b']dipyrrol-3(1H)-yl]carbonyl]-1H-indol-5-yl]amino]carbonyl]-5-[2-[[2-[[(1,1-dimethylethyl)oxy]carbonyl]hydrazino]carbonyl]ethyl]-2-benzofuran 3,6,9-trioxadecanoic acid ester (Cpd #18).

NMR (DMSO-$d_6$): δ 1.41 (s, 9H); 2.41 (s, 3H); 2.40–2.50 (t, 2H); 2.90–3.00 (t, 2H); 3.25 (s, 3H); 3.42–3.50 (m, 2H); 3.53–3.65 (m, 4H); 3.70–3.80 (m, 3H); 3.94–4.03 (d, 1H); 4.13–4.24 (t, 1H); 4.57 (s, 2H); 4.56–4.66 (d, 1H); 4.68–4.81 (t, 1H); 7.18 (s, 1H); 7.26 (s, 1H); 7.32–7.40 (dd, 1H); 7.45–7.53 (d, 1H); 7.56–7.67 (m, 3H); 7.86 (s, 1H); 8.22 (s, 1H); 8.72 (s, 1H); 9.59 (s, 1H); 10.47 (s, 1H); 11.15 (s, 1H); 11.69 (s, 1H). TLC: $R_f$=0.44 in (20-80) DMF-toluene.

EXAMPLE 19

Preparation of (S)-[[[-2[[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-(hydrazino)carbonyl]ethyl-2-benzofuran 3,6,9-trioxadecanoic acid ester (Cpd #19).

A 4 mg (0.0045 mmole) quantity of (S)-[[[-2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-[[2-[[(1,1-dimethylethyl)oxy]carbonyl]hydrazino]carbonyl]ethyl-2-benzofuran 3,6,9-trioxadecanoic acid ester (Cpd #18) is treated with 0.2 mL of trifluoroacetic acid at 25° C. After 2 min the reaction is evaporated under vacuum (<0.2 mm Hg) and the residue immediately dissolved in 0.25 mL of DMF and the solution added to the top of a 1.25 g Dowex 2-X8 (50–100 mesh) ion exchange column in the chloride form. The column is eluted with DMF, collecting fractions of 0.25 mL. The fractions are analyzed by HPLC on a Altex Ultrasphere 5μ ODS 4.6×150 mm column eluted at 1.5 mL/min with (45-55-0.1) acetonitrile-water-TFA, following peak elution by UV at 295 nm. Under these conditions the starting material elutes in 7.7 min and (S)-[[[2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-(hydrazino)carbonyl]ethyl-2-benzofuran 3,6,9-trioxadecanoic acid ester in 5.2 min. The fractions containing product are combined and concentrated under high vacuum (<0.2 mm Hg).

TLC: $R_f$=0.40 in (50-50) acetonitrile-water on C-18 reversed phase silica gel plates.

EXAMPLE 20

Preparation of (S)-[[[-2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-[[2-[[(1,1-dimethylethyl)oxy]carbonyl]hydrazino]carbonyl]ethyl]-2-benzofuran glutaric acid monoester (Cpd #20).

A 30 mg (0.041 mmole) quantity of (S)-[[[-2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl-5-[2-[[2-[[(1,1-dimethylethyl)oxy]carbonyl]hydrazino]carbonyl]ethyl]-2-benzofuran (Cpd #15), 7 mg of glutaric anhydride and 3 mg of 4-N,N-dimethylaminopyridine are dissolved in 0.20 mL of pyridine and the solution heated to 65° C. under a nitrogen atmosphere for 3 hr followed by stirring for 64 hr at 25° C. The reaction is then added to 0.5 g of silica gel and evaporated under vacuum. The residue is added to the top of a 5 g silica gel column and the column eluted with (20-80) DMF-toluene until the TLC shows the starting (Cpd #15) is eluted. The solvent is then switched to (20-80-2) DMF-toluene-acetic acid and 2 mL fractions are collected. Evaporation, under vacuum (<0.2 mm Hg), leaves 27 mg of (S)-[[[-2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-[[2-[[(1,1-dimethylethyl)oxy]carbonyl]hydrazino]carbonyl]ethyl]-2-benzofuran glutaric acid monoester.

NMR (DMSO-$d_6$): δ 1.41 (s, 9H); 1.85–1.98 (q, 2H); 2.33–2.44 (t, 2H); 2.41 (s, 3H); 2.45–2.53 (t, 2H); 2.73–2.83 (t, 2H); 2.92–3.04 (t, 2H); 3.67–3.80 (t, 1H); 3.93–4.05 (d, 1H); 4.14–4.24 (t, 1H); 4.56–4.66 (d, 1H); 4.70–4.81 (t, 1H); 7.20 (s, 1H); 7.25 (s, 1H); 7.34–7.41 (dd, 1H); 7.45–7.53 (d, 1H); 7.55–7.70 (m, 3H); 7.71 (s, 1H); 7.85 (s, 1H); 8.23 (s, 1H); 8.75 (s, 1H); 9.60 (s, 1H); 11.13 (s, 1H); 11.13 (s, 1H); 11.71 (s, 1H). TLC: $R_f$=0.14 in (20-80) DMF-toluene. TLC: $R_f$=0.57 in (20-80-2) DMF-toluene-acetic acid.

EXAMPLE 21

Preparation of (S)-[[[-2[[1-(chloromethyl)-1,6-dihydro-5-hydroxy-8-methylbenzo[1,2-b: 4,3-b']dipyrrol-3(2H)-yl]carbonyl]-1H-indol-5-yl]amino]carbonyl]-5-[2-[[2-[[(1,1-dimethylethyl) oxy]carbonyl]hydrazino]carbonyl]ethyl]-2-benzofuran ester of N-[2-hydroxy-1,1-bis(hydroxymethyl)ethyl]glutaramic acid (Cpd #21).

A 25 mg (0.03 mmole) quantity of (S)-[[[-2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-[[2-[[(1,1-dimethylethyl)oxy]carbonyl]hydrazino]carbonyl]ethyl]-2-benzofuran glutaric acid monoester (Cpd #20), 7 mg of hydroxybenzotriazole, 7 μL of triethylamine, and 9 mg of ethyl dimethylaminopropyl-carbodiimide are dissolved in 0.20 mL of DMA and the reaction allowed to stand in the dark for 1.5 hr. The reaction is then treated with 7 mg of trihydroxymethylaminomethane and the reaction stirred in the dark at 25° C. for 21 hr. The reaction is then evaporated onto 0.5 g of silica gel under high vacuum (<0.2 mm Hg). The residue is added to the top of a 5 g silica gel column and eluted with (20-80) DMF-toluene, collecting 2 mL fractions. Evaporation of fractions 22–44 under high vacuum (<0.2 mm Hg) leaves 18 mg of ((S)-[[ [-2[[1-(chloromethyl)-1,6-dihydro-5-hydroxy-8-methylbenzo[1,2-b:4,3-b']dipyrrol-3(2H)-yl]carbonyl]-1H-indol-5-yl[amino]carbonyl]-5-[2-[[2-[[(1,1-dimethylethyl)oxy]carbonyl]hydrazino]carbonyl]ethyl]-2-benzofuran ester of N-[2-hydroxy-1,1-bis (hydroxymethyl)ethyl]glutaramic acid (Cpd #21).

NMR (DMSO-$d_6$): δ 1.41 (s, 9H); 1.84–1.99 (q, 2H); 2.24–2.36 (t, 2H); 2.41 (s, 3H); 2.41–2.50 (t, 2H); 2.70–2.80 (t, 2H); 2.90–3.02 (t, 2H); 3.56 & 3.58 (d, 6H); 3.66–4.03 (d, 1H); 4.13–4.24 (t, 1H); 4.54–4.65 (d, 1H); 4.67–4.80 (2t, 4H); 7.18 (s, 2H); 7.33–7.40 (dd, 1H); 7.44–7.53 (d, 1H); 7.56–7.69 (m, 3H); 7.71 (s, 1H); 7.84 (s, 1H); 8.22 (s, 1H); 8.73 (s, 1H); 9.58 (s, 1H); 10.46 (s, 1H); 11.09 (s, 1H); 11.69 (s, 1H). TLC: $R_f$=0.60 in (30-70) DMF-toluene. HPLC: RT=4.06 min on 4.6×150 mm Altex Ultrasphere 5μ ODS column eluted at 1.5 mL/min with (45-55-0.1) acetonitrile-water-TFA; RT=6.51 min on 4.6×150 mm Altex Ultrasphere 5μ ODS column eluted at 1.5 mL/min with (43-57-0.1) acetonitrile-water-TFA.

EXAMPLE 22

Preparation of (S)-[[[-2[[1-(chloromethyl)-1,6-dihydro-5-hydroxy-8-methylbenzo[1,2-b: 4,3-b']dipyrrol-3(2H)-yl]

carbonyl]-1H-indol-5-yl]amino]carbonyl]-5-[2-(hydrazino) carbonyl]ethyl-2-benzofuran ester of N-[2-hydroxy-1,1-bis (hydroxymethyl)ethyl]glutaramic acid (Cpd #22).

A 16 mg (0.017 mmole) quantity of (Cpd #22) is treated with 0.90 mL of trifluoroacetic acid in 25° C. After 2 min the mixture is evaporated under high vacuum (<02. mm Hg). The residue is immediately dissolved in 1 mL of DMF and added to the top of a 5 Dowex 2-X8 (50–100 mesh) ion exchange column in the chloride form. The column is eluted with DMF, collecting fractions of 1 mL. Evaporation of fractions 3–7 under high vacuum (<0.2 mm Hg) leaves 15 mg of slightly impure ((S)-[[[-2[[1-(chloromethyl)-1,6-dihydro-5-hydroxy-8-methylbenzo[1,2-b:4,3-b']dipyrrol-3 (2H)-yl]carbonyl-1H-ind-5-yl]amino]carbonyl]-5-[2-(hydrazino)carbonyl]ethyl-2-benzofuran ester of N-[2-hydroxy-1,1-bis(hydroxymethyl)ethyl]glutaramic acid, Cpd #22). This material is dissolved in 0.6 mL of DMF and the solution diluted with 0.4 mL of water. This mixture is chromatographed over 2 g of C-18 reversed phase silica gel, eluting with 3 mL of (60-40) DMF-water followed by 30 mL of (70-30) DMF-water. Fractions of 1 mL are collected. Evaporation of fractions 9–13 leaves 3 mg of ((S)-[[[-2[[1-(chloromethyl)-1,6-dihydro-5-hydroxy-8-methylbenzo[1,2-b:4,3-b']dipyrrol- 3(2H)-yl]carbonyl]-1H-indol-5-yl]amino] carbonyl]-5-[2-(hydrazino)carbonyl]ethyl-2-benzofuran ester of N-[2-hydroxy-1,1-bis(hydroxymethyl)ethyl] glutaramic acid (Cpd #22).

NMR (DMSO-$d_6$): δ 1.84–1.98 (q, 2H); 2.25–2.35 (t, 2H); 2.36–2.44 (t, 2H); 2.41 (s, 3H); 2.67–2.77 (t, 2H); 2.90–3.00 (t, 2H); 3.55 & 3.57 (d, 6H); 3.67–3.77 (t, 1H); 3.94–4.04 (d, 1H); 4.13–4.25 (t, 1H); 4.57–4.65 (d, 1H); 4.70–4.82 (2t, 4H); 7.18 (s, 1H); 7.23 (s, 2H); 7.30–7.37 (d, 1H); 7.44–7.51 (d, 1H); 7.56–7.66 (m, 4H); 7.71 (s, 1H); 7.84 (s, 1H); 8.22 (s, 1H); 8.99 (s, 1H); 10.45 (s, 1H); 11.09 (s, 1H); 11.69 (s, 1H). TLC: $R_f$=0.60 in (70-30) DMF-water on C-18 silica gel reversed phase TLC plates.

EXAMPLE 23

Preparation of (S)-[[[-2[[1-(chloromethyl)-1,6-dihydro-5-hydroxy-8-methylbenzo[1,2-b: 4,3-b']dipyrrol-3(2H)-yl] carbonyl]1H-1H-indol-5-yl]amino]carbonyl]-5-[2-[[(1,1-dimethylethyl)oxy]carbonyl]hydrazino]carbonyl]ethyl]-2-benzofuran glutaric acid monoester mono amide of 7-amino-naphthalene-1,3-disulfonic acid disodium salt (Cpd #23).

A 25 mg (0.03 mmole) quantity of (S)-[[[-2 [[1-(chloromethyl)-1,6-dihydro-5-hydroxy-8-methylbenzo[1,2-b:4,3-b']dipyrrol-3(2H)-yl]carbonyl]-1H-indol-5-yl]amino] carbonyl]-5-[2-[[2-[[(1,1-dimethylethyl)oxy]carbonyl] hydrazino]carbonyl]ethyl]-2-benzofuran glutaric acid monoester (Cpd #20), 7 mg of hydroxybenzotriazole, 7 μL of triethylamine, and 9 mg of ethyl dimethylaminopropyl-carbodiimide are dissolved in 0.20 mL of DMA and the solution stirred at 25° C. for 1.5 hr. To the reaction is then added 10 mg (0.033 mmole) of 7-amino-1,3-naphthalenedisulfonic acid dissolved in 10 μL of triethyl amine and 20 μL of water, the residual solution being washed in with 100 μL of DMF. The reaction is stirred in the dark at 25° C. for 21 hr. The reaction is then evaporated onto 0.5 g of Celite under high vacuum (<0.2 mm Hg). The residue is added to the top of a 5 g C-18 reverse phase silica gel column and eluted with 10 mL of (10-90) DMF-1% sodium chloride in water, and subsequently with 10 mLs each of solvent changing from 10%–80% DMF in water in increments of 10%. Fractions of 2 mL are collected. The desired (S)-[[[-2[[1-(chloromethyl)-1,6-dihydro-5-hydroxy-8-methylbenzo[1,2-b:4,3-b']dipyrrol-3(2H)-yl]carbonyl] 1H-indol-5-yl]amino]carbonyl]-5-[2-[[2-[[(1,1-dimethylethyl)oxy]carbonyl]hydrazino]carbonyl]ethyl-2-benzofuran glutaric acid monoester mono amide of 7-amino-naphthalene-1,3-disulfonic acid disodium salt is obtained as a solid residue by evaporation under high vacuum (<0.2 mm Hg) of those fractions found by TLC and HPLC to contain this material.

NMR (DMSO-$d_6$, TMS): δ 1.41 (s, 9H); 1.99–2.10 (q, 2H); 2.40 (s, 3H); 2.40–2.48 (t, 2H); 2.50–2.59 (t, 2H); 2.77–2.87 (t, 2H); 2.90–3.01 (t, 2H); 3.68–3.79 (t, 1H); 3.94–4.03 (d, 1H); 4.13–4.24 (t, 1H); 4.56–4.66 (d, 1H); 4.70–4.80 (t, 1H); 7.18 (s, 1H); 7.24 (s, 1H); 7.34–7.40 (d, 1H); 7.46–7.53 (d, 1H); 7.56–7.67 (m, 3H); 7.70 (s, 1H); 7.85–7.92 (m, 2H); 8.00 (s, 1H); 8.13–8.20 (d, 1H); 8.20–8.24 (m, 2H); 8.67 (s, 1H); 8.73 (s, 1H); 9.59 (s, 1H); 10.39 (s, 1H); 10.46 (s, 1H); 11.13 (s, 1H); 11.72 (s, 1H).

HPLC: Vydac Protein-Peptide $C_{18}$; 1.5 ml/minute; 295 nm; eluted for 2 minutes with 20% $CH_3CN$—80% 50 mM NEt3/HOAc (pH≈5.5), followed by a 5 minute gradient to 80% $CH_3CN$—20% 50 mM NEt3/HOAc, followed by 80% $CH_3CN$—20% 50 mM NEt3/HOAc. Retention time: 7.6 minutes.

EXAMPLE 24

Preparation of (S)-[[[-2[[1-(chloromethyl)-1,6-dihydro-5-hydroxy-8-methylbenzo[1,2-b: 4,3-b']dipyrrol-3(2H)-yl] carbonyl]-1H-indol-5-yl]amino]carbonyl]-5-[2-(hydrazino) carbonyl]ethyl-2-benzofuran glutaric acid monoester mono amide of 7-amino-naphthalene-1,3-disulfonic acid disodium salt (Cpd #24).

A 20 mg (0.016 mmole) quantity of (S)-[[[-2[[1-(chloromethyl)-1,6-dihydro-5-hydroxy-8-methylbenzo[1,2-b:4,3-b']dipyrrol-3(2H)-yl]carbonyl]-1H-indol-5-yl]amino] carbonyl]-5-[2-[[2-[[(1,1-dimethylethyl)oxy]carbonyl] hydrazino]carbonyl]ethyl]-2-benzofuran glutaric acid monoester mono amide of 7-amino-naphthalene-1,3-disulfonic acid disodium salt (Cpd #23) is treated with 0.90 mL of trifluoroacetic acid at 25° C. After 2 min the mixture is evaporated under high vacuum (<02. mm Hg). The residue is immediately dissolved in 1 mL of DMF evaporated under high vacuum (<0.2 mm Hg) unto 0.5 g of Celite. The residue is added to the top of a 5 g C-18 reverse phase silica gel column and eluted with 10 mL of (10-90) DMF-1% sodium chloride in water, and subsequently with 10 mLs each of solvent changing from 10%–80% DMF in water in increments of 10%. Fractions of 2 mL are collected. The desired (S)-[[[-2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-(hydrazino)carbonyl] ethyl-2-benzofuran glutaric acid monoester mono amide of 7-amino-naphthalene-1,3-disulfonic acid disodium salt is obtained as a solid residue by evaporation under high vacuum (<0.2 mm Hg) of those fractions found by TLC and HPLC to contain this material.

NMR (DMSO-$d_6$, TMS): δ 1.98–2.12 (q, 2H); 2.40 (s, 3H); 2.34–2.46 (t, 2H); 2.52–2.60 (t, 2H); 2.78–2.88 (t, 2H); 2.93–3.01 (t, 2H); 3.68–3.79 (t, 1H); 3.93–4.03 (d, 1H); 4.10–4.23 (t, 1H); 4.55–4.65 (d, 1H); 4.68–4.81 (t, 1H); 7.18 (s, 1H); 7.23 (s, 1H); 7.30–7.39 (d, 1H); 7.45–7.53 (d, 1H); 7.57–7.67 (m, 3H); 7.70 (s, 1H); 7.83–7.93 (m, 2H); 8.01 (s, 1H); 8.10–8.19 (d, 1H); 8.19–8.24 (m, 2H); 8.67 (s, 1H); 8.98 (s, 1H); 10.39 (s, 1H); 10.45 (s, 1H); 11.13 (s, 1H); 11.72 (s, 1H).

HPLC: Vydac Protein-Peptide $C_{18}$; 1.5 ml/minute; 295 nm; linear gradient over 3 minutes of 40% $CH_3CN$—60% 50 mM NEt3/HOAc at pH≈5.5 to 45% $CH_3CN$—55% 50 mM NEt3/HOAc. Retention time: 3.13 minutes.

The starting compounds are known or can be readily prepared by known methods. See M. A. Warpehoski, Tet. Lett., 27, 4103 (1986); W. W. Wierenga, J. Am. Chem. Soc., 103, No. 18, 1981; D. G. Martin, J. Antibiotics 1985, 38, 746; and M. A. Warpehoski, I. Gebhard, R. C. Kelly, W. C. Krueger, L. H. Li, J. P. McGovren, M. D. Prairie, N. Wicnienski and W. Wierenga, J. Med. Chem., 1988, 31, pp. 590–603.

The preparation of (S)-1-(chloromethyl)-1,6-dihydro-5-hydroxy-8-methyl-benzo[1,2b:4,3-b']dipyrrole-3(2H)-carboxylic acid 1,1-dimethyl ester BOC(CPI) chlorophenyl HCl is described in R. C. Kelly, I. Gebhard, N. Wicnienski, P. A. Aristoff, P. D. Johnson, D. G. Martin, J. Am. Chem. Soc. 987, 109 6837.

The spirocyclopropylcyclohexadienyl compounds of Formula A and 1-(halomethyl)-1,6-hydro-5-hydroxy-8-methyl-benzo[1,2-b:4,3b']dipyrrole-3(2H)-yl 5-ester or urethanes (Formula B) can also be prepared by the procedures and methods disclosed in U.S. patent application Ser. No. 894,314, filed Aug. 7, 1986 (now abandoned), and PCT/87/03227 patent application filed Dec. 11, 1987. Both are incorporated herein by reference. See also EP Application 0 154 445 (published 9 Nov. 1985).

The compounds of Formula I and II are particularly useful as antitumor agents. Examples of compounds of Formula I and II demonstrate antitumor activity in P388 leukemic mice, and also show significant activity in the L1210 leukemia and B16 melanoma murine test systems. These murine test systems are predictive for clinically useful human antitumor agents (see, for example, A. Geldin et al, European J. Cancer, Vol. 17, pp 129–142, 1981; J. M Vendetti, Cancer Treatment Reports, Vol. 67, pp. 767–772, 1983; and J. M. Vendetti et al, Advances in Pharmacology and Chemotherapy, Vol. 20, pp. 1–20, 1984), and, therefore, the compounds of the subject invention (Formula I and II) will be useful in the control and treatment of susceptible neoplastic (cancer) diseases, including susceptible leukemics, in humans when given, for example, intravenously in doses of 0.001 µg/kg to about 10 mg/kg of body weight per day, the exact dose depending on the age, weight, and condition of the patient, and on the frequency of administration.

The compounds of Formula I and II are effective when administered intravenously (IV) in fluid solutions by bolus injection or by infusion. The preferred doses are 0.01 microgram/kg to 1000 microgram/kg by bolus injection and 0.0002 to 20 microgram/kg/min by infusion. The exact dose will vary depending on the particular compound as well as the age, weight, route of administration, and physical condition of the patient, and on the frequency of administration.

Illustrative L1210 testing data on the compounds of Formula I are presented in Table I.

In addition to the administration of the compounds of the subject invention directly, the compounds (Formula I and II) are preferably coupled to antibodies, either monoclonal (Mab) or polyclonal, directed at specific cancer cell antigens and thus selectively eliminate those disease cells from the patient. The coupling of the compounds of this invention to antibodies can be done by methods well known in the art including those of European Patent Application 85401776.1 (Publication No. 0175617) and 83400461.6 (Publication No. 00088695), herein incorporated by reference, as well as A. H. Blair, T. I. Ghose, J. Immunol. Methods, 59, 129 (1983), N. Endo, Y. Kato, Y. Takeda, M. Saito, N. Umemoto, K. Kishida, T. Hara, Cancer Res. 47, 1076 (1987), E. Hurwitz, R. Levy, R. Maron, M. Wilchek, R. Amon, M. Sela, Cancer Res. 35, 1175 (1975), K. Ohkawa, Y. Tsukada, N. Hibi, N. Umemoto, T. Hara, Cancer Immunol. Immunother. 23, 81 (1986), B. Packard, M. Edidin, A. Komoriya, Biochemistry, 25, 3538 (1986). J. D. Rodwell, V. L. Alvarez, C. Lee, A. D. Lopes, J. W. F. Goers, H. D. King, H. J. Powsner, T. J. McKeam, Proc. Natl. Acad. Sci. USA, 83, 2632 (1986), Y. Tsukada, Y. Kato, N. Umemoto, Y. Takeda, T. Hara, H. Hirai, J. Nat. Cancer Inst. 73, 721 (1984), and N. Umemoto, Y. Kato, Y. Takeda, M. Saito, T. Hara, M. Seto, T. Takahashi, J. Appl. Biochem6, 297 (1984).

Further, the compounds (Formula I and II) can be utilized to treat AIDS by preparing conjugates between the compounds and soluble human CD4 or a soluble human CD4 protein fragment capable of binding to the gp120 envelope protein of the human immunodeficiency virus.

The amino acid sequence of soluble human CD4 (or soluble human CD4 protein fragment capable of binding to the gp120 envelope protein of the human immunodeficiency virus, i.e. biologically active CD4 fragments) can be the same as mature human CD4 protein or modified in such a manner that the sequences are different from that of mature CD4 protein in that there can be 1) deletion(s) from, substitution(s) in and/or additions to the amino acid sequence of human CD4 (see Madden, P. J. et al., "The Isolation and Nucleotide Sequence of a cDNA Encoding the T Cell Surface Protein T4: A New Member of the Immunoglobulin Gene Family", Cell, Vol. 24, pp. 93–104, August 1985, and Garlick, R. L., et al., "*Eschericia coli* expression, purification, and biological activity of a truncated soluble CD4", AIDS Research and Human Retroviruses, Vol. 6, No. 4, pp. 465–479, 1990; 2) it is truncated (i.e., includes the same amino acid sequence); 3) it is truncated and the truncated form or portion includes deletion(s) from, substitution(s) in and/or additions to the amino acid sequence which occurs in the corresponding portion or segment (see references cited above).

Preferably biologically active, and/or modified soluble CD4 fragments include none (or at least less than six amino acids) of the hydrophobic transmembrane portion. Such biologically active (modified or unmodified) soluble CD4 fragments are long enough (ten amino acids or longer) to enable them to bind effectively to the gp120 envelop protein of the HIV virus. Although such fragments need not exhibit complete hemology with human CD4 protein, they will have about 75% homology in those regions to bind to gp120.

Illustrative CD4 fragments include those disclosed in the patent and/or scientific literature, e.g. Nature, vol 337, p. 525–31 (1989) or U.S. patent application Ser. No. 333,516; filed 5 Mar. 1989 (TUC's 183 fragment).

The novel conjugates of the subject invention (compounds of Formula I or II and antibody/CD4) are effective when administered intravenously (IV) in fluid solutions by bolus injection or by infusion. The preferred doses are 0.01 microgram/kg to 1000 microgram/kg (in terms of compound I or II) by bolus injection and 0.0002 to 20 microgram/kg/min by infusion. The exact dose will vary depending on the particular compound as well as the age, weight, route of administration, and physical condition of the patient, and on the frequency of administration.

Generic Example 1

Coupling of carboxy terminated Compounds I or II (eg. formulas A', B', C' and the like) with active amine, guanidine, or hydrazide moiety of linker. See CHART 1.

A 0.1 mMole quantity of the carboxy terminated CPI compound is dissolved in an aprotic solvent or mixture of aprotic solvents such as DMF, DMA, THF, dioxane, etc. (preferably DMA or DMF) to give a concentration of 0.01 to 1.0M. The resultant solution is stirred at −10° to 100° C. (preferably at 20°–25° C.) and treated with a peptide coupling agent such as ethyl dimethylaminopropyl carbodiimide hydrochloride (EDC), dicyclohexylcarbodiimide (DCC) isobutyl chloroformate, or pivaloyl chloride, etc. (preferably EDC) either in the presence or absence of a coupling mediator such as N-hydroxy-benzotriazole or N-hyroxysuccinimide, etc. The resultant solution may be premixed with a suitable linker (eg. a protected hydrazine such as $H_2NNHBoc$) so that both the CPI and the linker start at the same molar concentration or the linker may be dissolved in the same or other aprotic solvent, as listed above, and the linker solution added to the CPI compound-peptide coupling agent mixture (with or without coupling mediator) until the same molar concentration of CPI carboxylate and linker are reached. The reaction is stirred at −10° to 100° C. (preferably at 20°–25° C.) 1 min to 48 hr (preferably 2–4 hr). The reaction is then diluted with water and the product either collected by filtration or extracted with a water immiscible solvent such as methylene chloride or ethyl acetate. If extracted the extract is dried and evaporated. This product or that collected by filtration is purified by crystallization or by chromatography using either silica gel or other normal phase support or by reverse phase chromatography on C-2, C-8, or C-18 silica gel.

Generic Example 2

Coupling of amino terminated Compounds I or II (eg. formulas D', E', F and the like) with active carboxyl moiety of linker. See CHART 2.

A 0.1 mMole quantity of the carboxyl terminated linker is dissolved in an aprotic solvent or mixture of aprotic solvents such as DMF, DMA, THF, dioxane, etc. (preferably DMA or DMF) to give a concentration of 0.01 to 1.0M. The resultant solution is stirred at −10° to 100° C. (preferably at 20°–25° C.) and treated with a peptide coupling agent such as ethyl dimethylaminopropyl carbodiimide hydrochloride (EDC), dicyclohexylcarbodiimide (DCC) isobutyl chloroformate, or pivaloyl chloride, etc. (preferably EDC) either in the presence or absence of a coupling mediator such as N-hydroxy-benzotriazole or N-hyroxysuccinimide, etc.

The resultant solution may be premixed with the amino or hydrazido terminated CPI compound so that both the CPI and the linker start at the same molar concentration or the CPI compound may be dissolved in the same or other aprotic solvent, as listed above, and the CPI compound solution added to the linker-peptide coupling agent mixture (with or without coupling mediator) until the same molar concentration of CPI carboxylate and linker are reached. The reaction is stirred at −10° to 100° C. (preferably at 20°–25° C.) 1 min to 48 hr (preferably 2–4 hr). The reaction is then diluted with water and the product either collected by filtration or extracted with a water immiscible solvent such as methylene chloride or ethyl acetate. If extracted the extracted is dried and evaporated. This product or that collected by filtration is purified by crystallization or by chromatography using either silica gel or other normal phase support or by reverse phase chrochromatography on C-2, C-8, o C-18 silica gel.

Generic Example 3

Coupling of linker as ester prodrug to Compound I or II, (formulas G', H' or the like). See CHART 3.

The CPI compound is dissolved at 0.01 to 3M in an aprotic solvent such a pyridine, methylene chloride, THF,
etc (preferably pyridine where no additional tertiary amino need be added) and the solution treated with a tertiary amino such as triethylamine, pyridine, or ethyldisopropylamino and the solution stirred at −10° to 100° C. To this solution is added the linker acyl halide (preferably the acylchloride) and the resultant solution stirred at −10° to 100° C. (preferably at 20°–25° C.) 1 min to 48 hr (preferably 2–4 hr). The reaction is then diluted with water. If a product precipitates as a solid it may be collected by filtration. Alternatively, the aqueous mixture may be extracted with a water immiscible solvent such as methylene chloride or ethyl acetate. The organic layer is washed with 5% aqueous sodium bicarbonate, dried over magnesium sulfate or sodium sulfate, and concentrated in vacuo. The product obtained thus from the extraction or as above by filtration may be further purified by normal phase chromatography on silica gel, alumina or other solid support or may be purified by reversed phase chromatography over C-2, C-8, or C-18 silica gel.

Generic Example 4

Removal of N-Boc or t-butyl ester protecting group from linker attached to CPI compound. Deprotection of compounds of formulas such I', J' and the like. See CHART 4.

The N-Boc or t-butyl ester protected linker attached to the CPI compound is dissolved at 0.01 to 2M in a solvent such as ethyl acetate, dioxane, or methylene chloride and the solution stirred at −50° to 100° C. (preferably at 20°–25° C.). This solution is treated with an acid known in the art for removal of N-Boc or t-Butyl ester groups such as HCl gas (1–3M in ethyl acetate) or trifluoroacetic acid for 1 min to 48 hr (preferably 2–4 hr). After the designated time the reaction is concentrated in vacuo. The product thus obtained may be further purified by normal phase chromatography on silica gel, alumina or other solid support or may be purified by reversed phase chromatography over C-2, C-8, or C-18 silica gel.

Genetic Example 5

Removal of N-Cbz or benzyl ester protecting group from linker attached to CPI compound. Deprotection of compounds of formulae such K', L' and the like. See CHART 5.

The N-Cbz (N-carbobenzyloxy or N-benzyloxycarbonyl) or benzyl ester protected linker attached to the CPI compound is dissolved at 0.01 to 2M in a solvent or combination of solvents such as MeOH, MeOH-THF, MeOH-dioxane, etc. and the solution stirred at −50° to 100° C. (preferably at 20°–25° C.). This solution is treated from 0.01 to 3M equivalent of a hydrogenolysis catalyst such as palladium metal, 5% palladium on carbon, Raney nickel, etc. (preferably 5–10% palladium on carbon at 0.01–0.2 molar equivalents). The solution may be hydrogenated directly with hydrogen at 1–5 times atmospheric pressure for 10 min to 48 hr (preferably 2–4 hr) or alternatively the solution of compound and catalyst may be treated with ammonium formate, formic acid, cyclohexadiene or other phase transfer catalytic hydrogenation hydrogen donors (preferably ammonium formate) and the resultant mixture stirred for 1 min to 48 hr (preferably 5 min to 3 hr). At the end of the designated time the reaction is filtered and the filtrate concentrated in vacuo. The product thus obtained may be further purified by normal phase chromatography on silica gel, alumina or other solid support or may be purified by reversed phase chromatography over C-2, C-8, or C-18 silica gel.

Genetic Example 6

Coupling of linker as urethane prodrug to compounds II, eg. formulas M'. See CHART 6.

The phenolic CPI compound is dissolved at 0.01 to 3M in an aprotic solvent such a pyridine, methylene chloride, THF, etc (preferably pyridine where no additional tertiary amine need be added) and the solution treated with a catalyst such as dibutyltinacetate or a tertiary amino such as triethylamine, pyridine, or ethyldisopropylamine and the solution stirred at −10° to 100° C. To this solution is added the linker isocyanate, chlorocarbamate or other activated aminocarbonyl derivative and the resultant solution stirred at −10° to 100° C. (preferably at 20 °–25° C.) 1 min to 48 hr (preferably 2–4 hr). The reaction is then diluted with water. If a product precipitates as a solid it may be collected by filtration. Alternatively, the aqueous mixture may be extracted with a water immiscible solvent such as methylene chloride or ethyl acetate. The organic layer is washed with 5% aqueous sodium bicarbonate, dried over magnesium sulfate or sodium sulfate, and concentrated in vacuo. The product obtained thus from the extraction or as above by filtration may be further purified by normal phase chromatography on silica gel, alumina or other solid support or may be purified by reversed phase chromatography over C-2, C-8, or C-18 silica gel.

Generic Example 7

Coupling of carboxy terminated CPI-linker structures, eg. formulas P', Q', R' and the like with active amine, guanidine, or hydrazide moiety of monoclonal antibody (Mab) or CD4. See CHART 7.

A 0.1 mMole quantity of the carboxy terminated CPI-linker compound is dissolved in an aprotic solvent or mixture of aprotic solvents such as DMF, DMA, THF, dioxane, etc. (preferably DMA or DMF) to give a concentration of 0.01 to 1.0M. The resultant solution is stirred at −10° to 100° C. (preferably at 20°–25° C.) and treated with a peptide coupling agent such as ethyl dimethylaminopropyl carbodiimide hydrochloride (EDC), dicyclohexylcarbodiimide (DCC) isobutyl chloroformate, or pivaloyl chloride, etc. (preferably EDC) either in the presence or absence of a coupling mediator such as N-hydroxy-benzotriazole or N-hyroxysuccinimide, etc. The resultant solution is added to HN terminated Mab or CD4 protein dissolved in a polar solvent such as DMF, DMA, formamide, or water, buffered water at or near isotonic sail concentrations at pH 6.5–8.0 (preferably about 7.04.5), or a mixture of any of such solvents until the same molar concentration of CPI-linker carboxylate and protein are reached. The reaction is stirred at −10° to 100° C. (preferably at 20°–25° C.) 1 min to 48 hr (preferably 2–4 hr). The reaction is then diluted with water, a water salt mixture such as aqueous ammonium sulfate, an alcohol such as methanol or ethanol and the product either collected by filtration or the product may dialyzed and the aqueous residue freeze dried. This product or that collected by filtration is purified by salt precipitation procedures or by chromatographics such as size exclusion chromatography, affinity chromatography or reverse phase chromatography on C-18 silica gel.

Generic Example 8

Coupling of amino, guanidino, or hydrazido terminated CPI-linker structures, eg. formulas T', U', V' or the like with activated carboxyl of monoclonal antibody (Mab) or CD4 (see Chart 8).

A 0.1 mMole quantity of the carboxy Mab or CD4 is dissolved in water, buffered water at or near isotonic salt concentrations at pH 6.5–8.0 (preferably about 7.0–7.5), or a polar solvent such as DMF, DMA, or formamide or a mixture of such polar solvents and water at 10°–30° C. The solution of the —NH terminated CPI-linker compound is dissolved in an aprotic solvent or mixture of aprotic solvents such as DMF, DMA, THF, dioxane, etc. (preferably DMA or DMF) to give a concentration of 0.01 to 1.0M which is added to the carboxyl terminated protein solution. The resultant solution is stirred at 0° to 100° C. (preferably at 20°–25° C.) and treated with 0.8 to 5.0 molar equivalents (preferably one equivalent) of a peptide coupling agent such as ethyl dimethylaminopropyl carbodiimide hydrochloride (EDC), dicyclohexylcarbodiimide (DCC) isobutyl chloroformate, or pivaloyl chloride, etc. (preferably EDC) either in the presence or absence of a coupling mediator such as N-hydroxy-benzotriazole or N-hyroxysuccinimide, etc. The reaction is stirred at 0° to 100° C. (preferably at 20°–25° C.) 1 min to 48 hr (preferably 2–4 hr.). The reaction is then diluted with water, a water salt mixture such as aqueous ammonium sulfate, an alcohol such as methanol or ethanol and the product either collected by filtration or the product may dialyzed and the aqueous residue freeze dried. This product or that collected by filtration is purified by salt precipitation procedures or by chromatographics such as size exclusion chromatography, affinity chromatography or reverse phase chromatography on C-18 silica gel.

Generic Example 9

Reduction of thiopyridyl terminated thiol (i.e. pyridyl disulfide) CPI-linker structures, eg. formulas X' and Y' and the like to thiol. See CHART 9.

A 0.1 mMole quantity of the thiopyridyl terminated thiol CPI-linker is dissolved in water or a polar solvent such as DMF, DMA, or formamide or a mixture of such polar solvents and water at 10°–50° C. To this is added an excess (2 to 50 fold excess, preferably 5 to 10 fold) of a reducing agent such as dithiothreitol and the mixture stirred for 5 min to 48 hr (preferably 30 min to 2 hr). The product thiol may then be isolated by precipitation with water or a non polar solvent or by extraction in an oxygen free environment. The material from precipitation or extraction may be used directly in the next step or be further purified by crystallization, selective precipitation, or chromatography in an oxygen free environment. Suitable chromatographic procedures include size exclusion chromatography, affinity chromatography or reverse phase chromatography on C-18 silica gel.

Generic Example 10

Coupling of thiol linker terminated CPI eg. structures AA' and AB', to thiol terminated Mab via disulfide linkage. See CHART 10.

A 0.1 mMole quantity of the thiol terminated Mab is dissolved in water, aqueous buffer at pH 3 to 10 (preferably at pH 7 to 8) and at a salt concentration near isotonic, or in aqueous mixtures with a polar solvent such as DMF, DMA, or formamide or a mixture of such polar solvents at 10°–50° C. To this is added an excess (2 to 50 fold excess, preferably 5 to 10 fold) of a of the thiol linker terminated CPI compound and the mixture stirred while bubbling oxygen through for 5 min to 48 hr (preferably 30 min to 2 hr). The product Mab disulfide linked CPI compound may then be isolated by precipitation with water, aqueous salt solutions such as 20% ammonium sulfate or saturated sodium sulfate, or a non polar solvent. Alternatively the product may be freed from low molecular weight impurities by dialysis. The material from precipitation or dialysis may be further purified by crystallization, selective precipitation, or chroma-

Genetic Example 11

Coupling of thiopyridyl terminated thiol (i.e. pyridyl disulfide) CPI-linker structures, eg. formulas X', Y' and the like to thiol terminated Mab. See CHART 11.

A 0.1 mMole quantity of the thiopyridyl terminated thiol CPI-linker is dissolved in water or a polar solvent such as DMF, DMA, or formamide or a mixture of such polar solvents and water at 10°–50° C. To this is added 0.5 to 3 equivalent (preferably 1 equivalent of thiol terminated antibody and the mixture adjusted to pH 0 to 5 (preferably pH 3 to 4) with an organic or inorganic acid or preferably with a buffer of those acids. The mixture is stirred for 5 10 min to 48 hr (preferably 30 min to 2 hr). The product disulfide may then be isolated and purified as in example 11 above.

Genetic Example 12

Coupling of N-maleimide terminated CPI-linker structures, eg. formulas AD', AE' and the like to thiol terminated Mab. See CHART 12.

A 0.1 mMole quantity of the N-maleimide CPI-linker is dissolved in water or a polar solvent such as DMF, DMA, or formamide or a mixture of such polar solvents and water at 10°–50° C. To this is added 0.5 to 3 equivalents (preferably 0.8 to 1.2 equivalents) of a thiol terminated Mab dissolved in water, an aqueous buffer of pH 3 to 10 (preferably pH 6 to 8) or a mixture of the previous solvents with polar solvents such as DMF, DMF or formamide and the mixture allowed to stand at 0°–50° C. (preferably 5°–20° C.) for 5 min to 48 hr (preferably 30 min to 2 hr). The product may then be isolated by precipitation with water, aqueous salt solutions such as 20% ammonium sulfate or saturated sodium sulfate, or a non polar solvent. Alternatively the product may be freed from low molecular weight impurities by dialysis. The material from precipitation or dialysis may be further purified by crystallization, selective precipitation, or chromatography. Suitable chromatographic procedures include size exclusion chromatography, affinity chromatography or reverse phase chromatography on C-18 silica gel.

Generic Example 13

Coupling of hydrazido terminated CPI-linker structures, eg. formulas AG', AH' and the like to formyl terminated Mab. See CHART 13.

A 0.1 mMole quantity of the hydrazido terminated CPI-linker is dissolved in water or a polar solvent such as DMF, DMA, or formamide or a mixture of such polar solvents and water at 0°–50° C. To this is added 0.5 to 3 equivalents (preferably 0.8 to 1.2 equivalents) of a formyl terminated Mab (prepared by cleavage of Mab glycosyl residue as in is known in the art) dissolved in water, an aqueous buffer of pH 3 to 10 (preferably pH 4 to 6) or a mixture of the previous solvents with polar solvents such as DMF, DMF or formamide and the mixture allowed to stand at 0°–50° C. (preferably 5°–20° C.) for 5 min to 48 hr (preferably 30 min to 2 hr). The product hydrazone may then be isolated by precipitation with water, aqueous salt solutions such as 20% ammonium sulfate or saturated sodium sulfate, or a non polar solvent. Alternatively the product may be freed from low molecular weight impurities by dialysis. The material from precipitation or dialysis may be further purified by crystallization, selective precipitation, or chromatography. Suitable chromatographic procedures include size exclusion chromatography, affinity chromatography or reverse phase chromatography on C-18 silica gel.

Generic Example 14

Coupling of amino terminated CPI-linker structures, eg. formulas AJ', AK', and the like to formyl terminated Mab. See CHART 14.

A 0.1 mMole quantity of the amino terminated CPI-linker is dissolved in water or a polar solvent such as DMF, DMA, or formamide or a mixture of such polar solvents and water at 0°–50° C. To this is added 0.5 to 3 equivalents (preferably 0.8 to 1.2 equivalents) of a formyl terminated Mab (prepared by cleavage of Mab glycosyl residue as in known in the art) dissolved in water, an aqueous buffer of pH 2 to 6 (preferably pH 3 to 5) or a mixture of the previous solvents with polar solvents such as DMF, DMF or formamide and the mixture treated with 1 to 100 equivalents of sodium cyanoborohydride (preferably 5 to 10 equivalents) and the mixture stirred at 0°–50° C. (preferably 5°–20° C.) for 5 min to 48 hr (preferably 30 min to 2 hr). The product amine may then be isolated by precipitation with water, aqueous salt solutions such as 20% ammonium sulfate or saturated sodium sulfate, or a non polar solvent. Alternatively the product may be freed from low molecular weight impurities by dialysis. The material from precipitation or dialysis may be further purified by crystallization, selective precipitation, or chromatography. Suitable chromatographic procedures include size exclusion chromatography, affinity chromatography or reverse phase chromatography on C-18 silica gel.

Generic Example 15

Maleimide based coupling of monoclonal antibodies (Mab) or CD4 fragments with compounds of Formula I or II, eg. Compounds of Formula AA', AC', AF' and the like. See CHART 15.

Maleimide terminated proteins can be prepared as described for the preparation of peptide labeled carrier proteins suitable for elicitation of peptide specific antibody responses.

References: J. A. Nicholas et al, J. Virology 62, 4465–4473 (1988); F. -T. Liu et al, Biochemistry 18, 690–697 (1979).

Succinimidyl 4-(N-maleimidomethyl)cyclohexane-1-carboxylate (0.5–40 equivalents, preferably 0.8–10 equivalents) or some other heterofunctional crosslinking reagent which contains an N-hydroxysuccinimidyl ester on one end and a maleimido group on the opposite end is dissolved in water or a polar solvent such as DMF, DMA or formamide and the solution is added to a stirred solution of protein (0. 1 mMol) dissolved in 0.01N sodium phosphate, pH 7.0, (0.75 ml). This mixture is stirred for 5 min to 4 hrs (preferably 20 min to 1 hr) at 0°–50° C. (preferably 5°–25° C.) and loaded directly onto a Sephadex 0–25 column previously equilibrated at 4° C. with 0.1N sodium phosphate, pH 6.0. The column is run in the same buffer at 4° C. The first peak eluted contains the maleimide terminated protein which is suitable for direct coupling with a thiol terminated CPI-linker.

Coupling of thiol terminated CPI-linker structures ($R_{50}$=SH) (cpds such as T', U', V') to maleimide terminated proteins such as Mab, biologically active soluble human CD4 fragments or truncated forms of soluble human CD4.

A 0.1 mMole quantity of the maleimide terminated CD4 is prepared in water, aqueous buffer of pH 3–10 (preferably pH 6–8) or a mixture of the previous solvents with polar solvents such as DMF, DMA, or formamide. To this is added 0.5–40 equivalents (preferably 0.8–10 equivalents) of a thiol terminated CPI-linker compound dissolved in water or a polar solvent such as DMF, DMA or formamide or a mixture of such polar solvents and water at 0°–50° C. and the mixture allowed to stand at 0°–50° C. (preferably 5°–25° C.) for 5 min to 48 hr (preferably 30 min to 2 hr). The product nay then be isolated by precipitation with water, aqueous salt solutions such as 20% ammonium sulfate or saturated sodium sulfate, or a nonpolar solvent. Alternatively, the product may be freed from low molecular weight impurities by dialysis. The material from precipitation or dialysis may be further purified by crystallization, selective precipitation, or chromatography. Suitable chromatographic procedures include size exclusion chromatography, affinity chromatography or reverse phase chromatography on C-18 silica gel.

The compounds of formula I and II are also useful as antibacterial agents. These compounds are useful to control the proliferation of susceptible microbes in various environments using standard microbiological techniques. Such environments include dental utensils contaminated with *S. aureus*, and the like, and laboratory benches in a microbiological laboratory which can be cleansed with a formulation containing about 1–10% (w/v) of a compound of formula I or II.

CHART 1

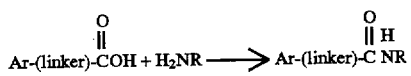

where Ar(linker)-CO$_2$H ≡ A', B', C' shown below and R = linker moiety.

For example:

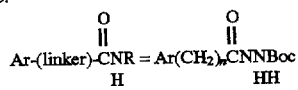

n = 0–5

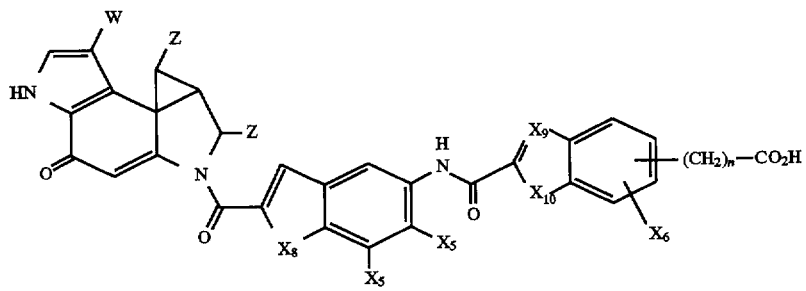

A'

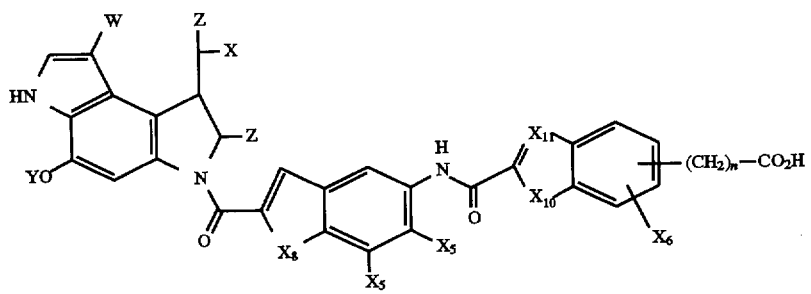

B'

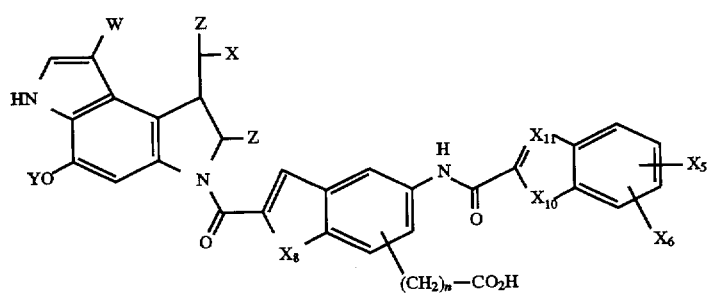

C'

CHART 2
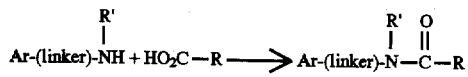
where Ar-(linker)-NH$\overset{R'}{|}$ ≡ D', E' and F' shown below
and R is a linker moiety.
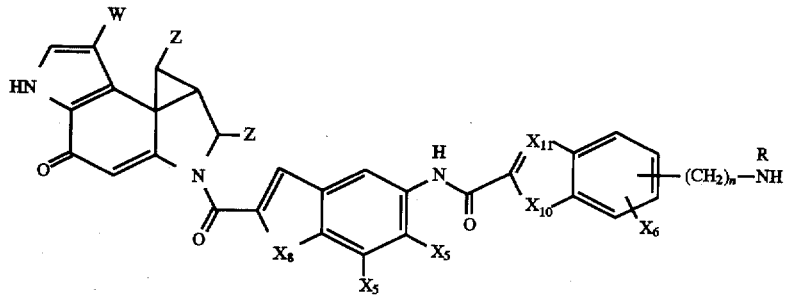
D'
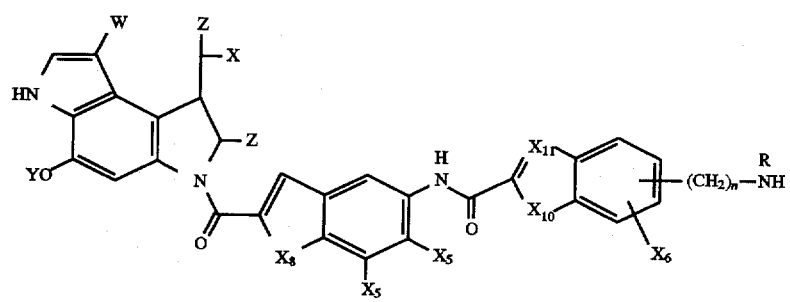
E'
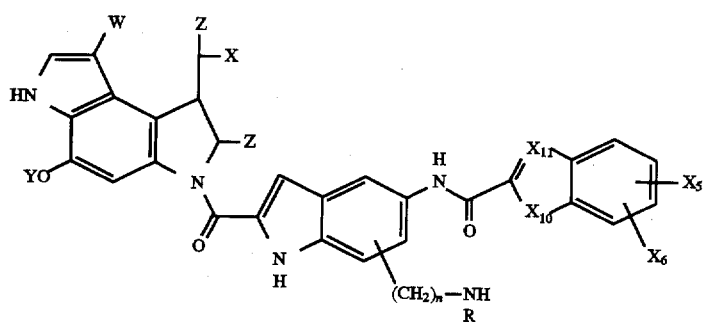
F'

CHART 3
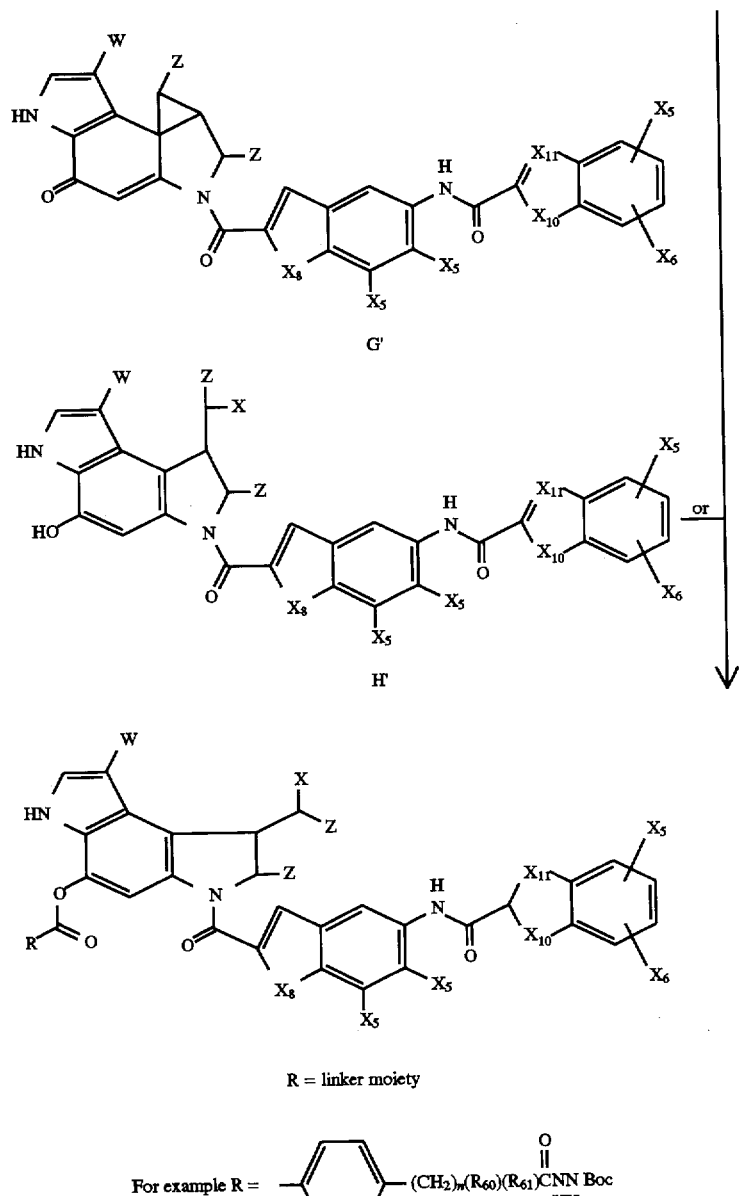
R = linker moiety
For example R = 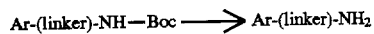
(n = 0–2)
CHART 4
Ar-(linker)-NH—Boc ⟶ Ar-(linker)-NH₂
where Ar-(linker)-NHBoc ≡ I', J' shown below.

-continued
CHART 4
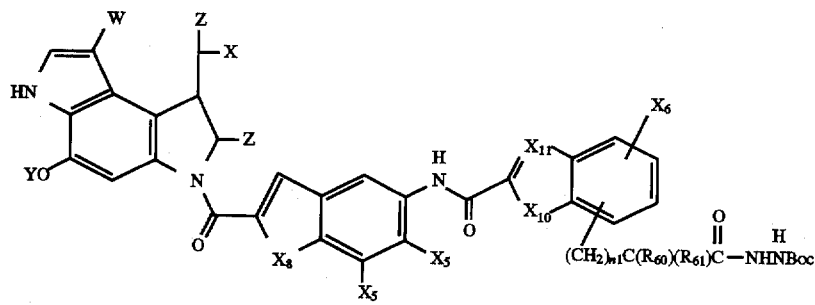
I'
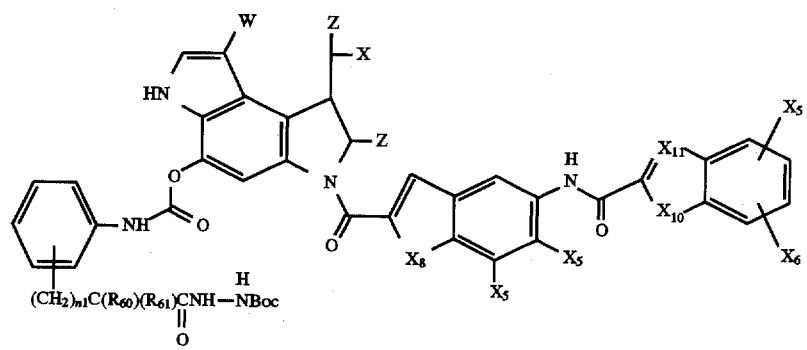
J'
CHART 5
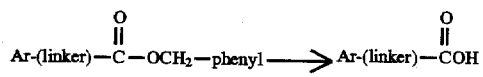
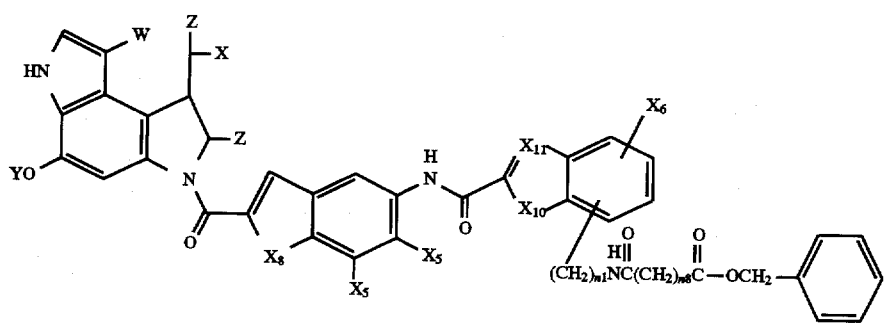
K'
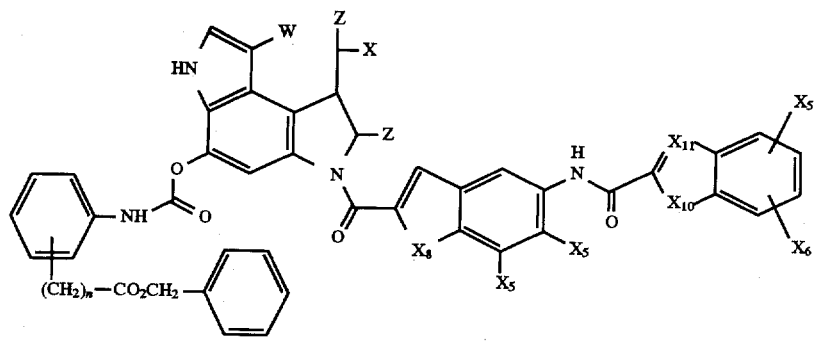
L'

CHART 6
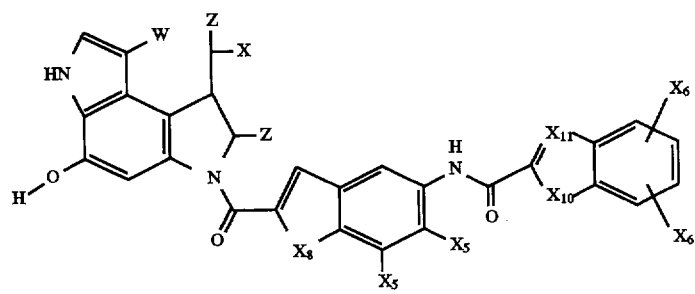
M'
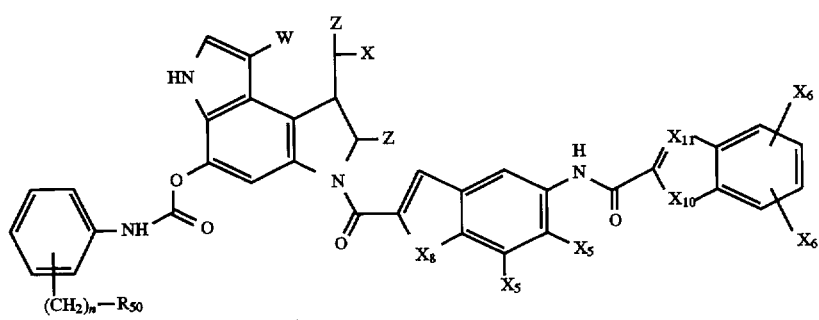
N'
CHART 7
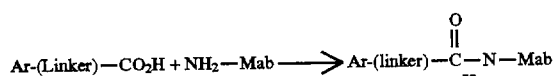
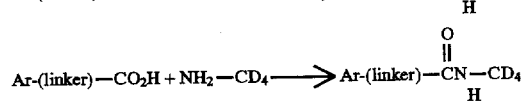
where Ar-(linker)—CO$_2$H ≡ P', Q', R' shown below
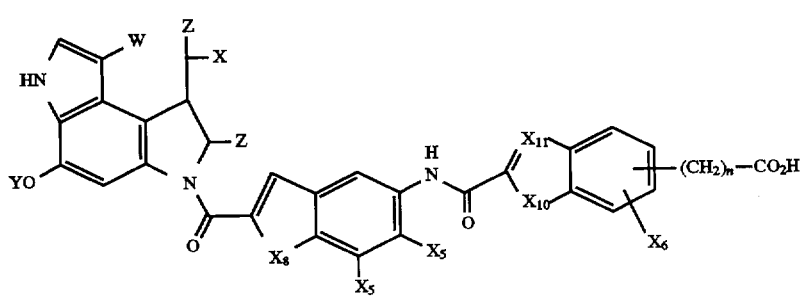
P'
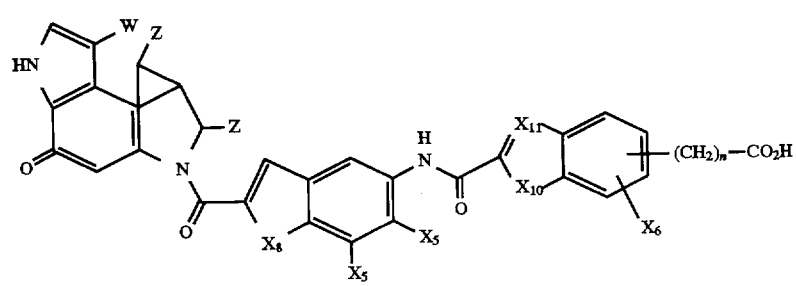
Q'

-continued
CHART 7
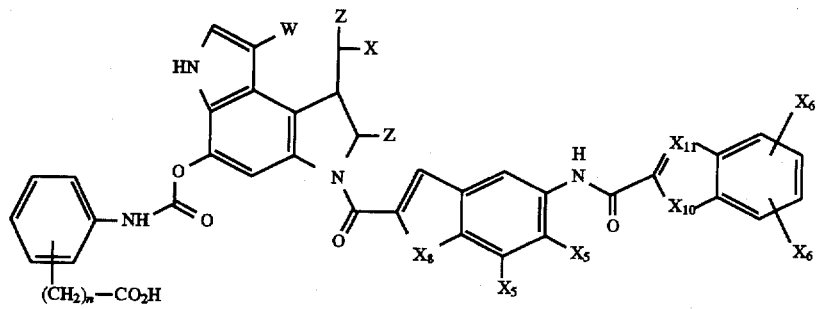
CHART 8
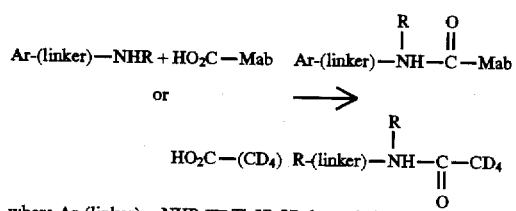
where Ar-(linker)—NHR ≡ T', U', V' shown below.
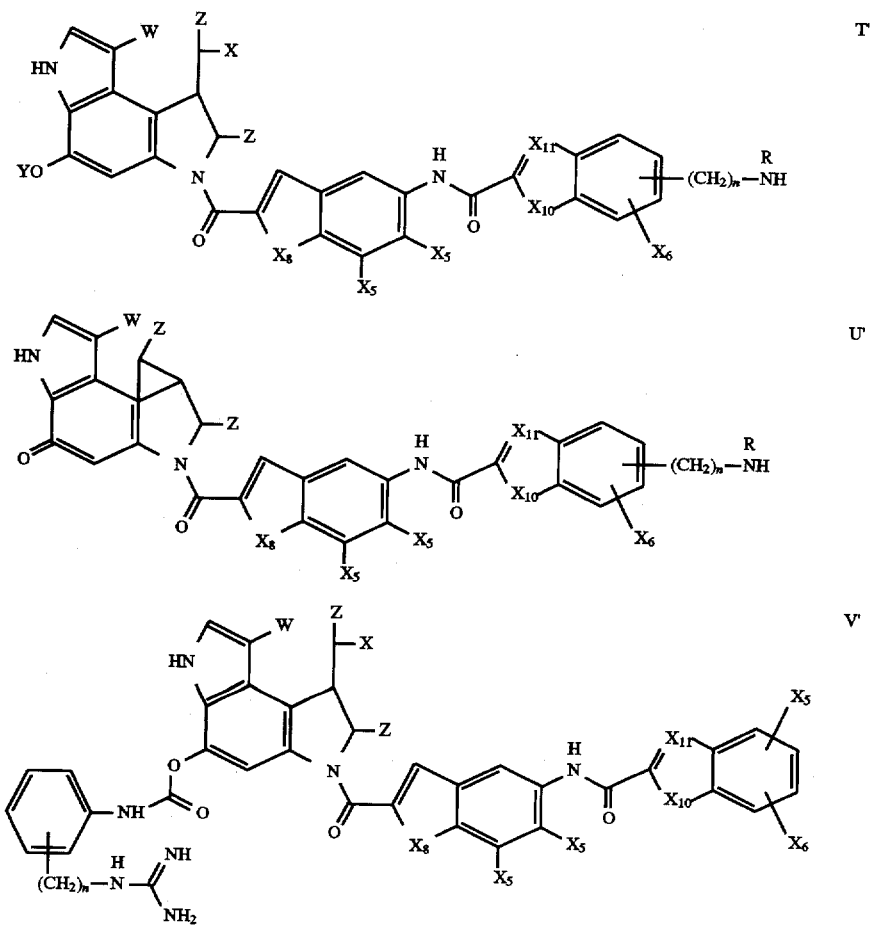

CHART 9
where Ar-(linker)-SS-pyridine ≡ X', Y' shown below.
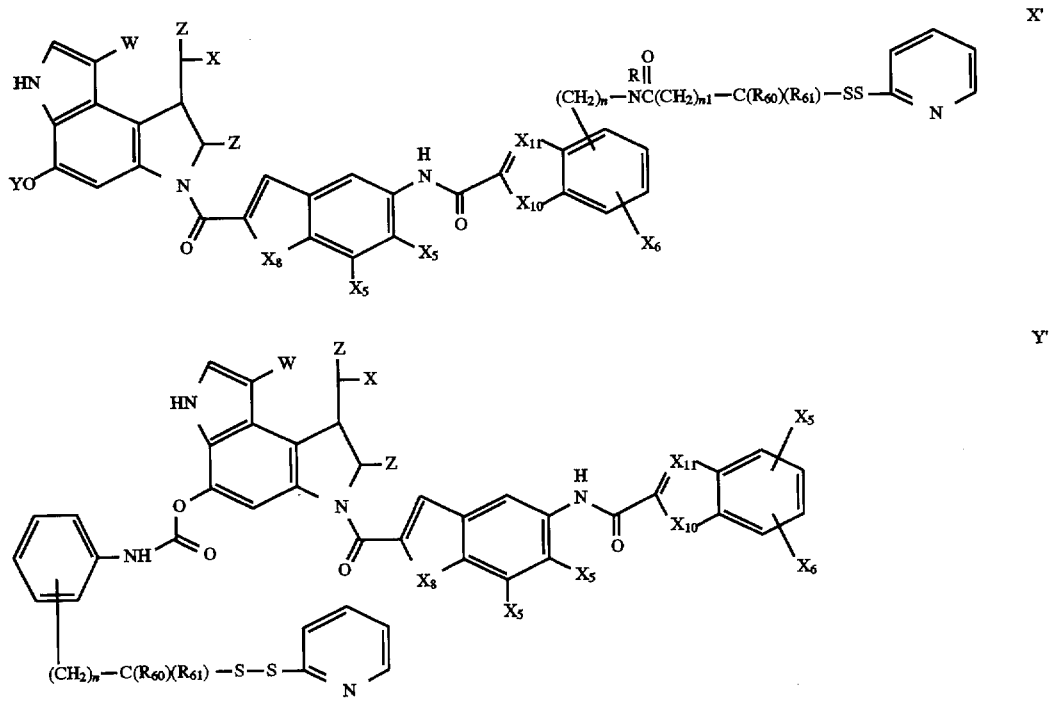
CHART 10
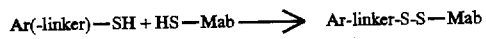
where Ar-(linker)-SH ≡ AA', AB' shown below.
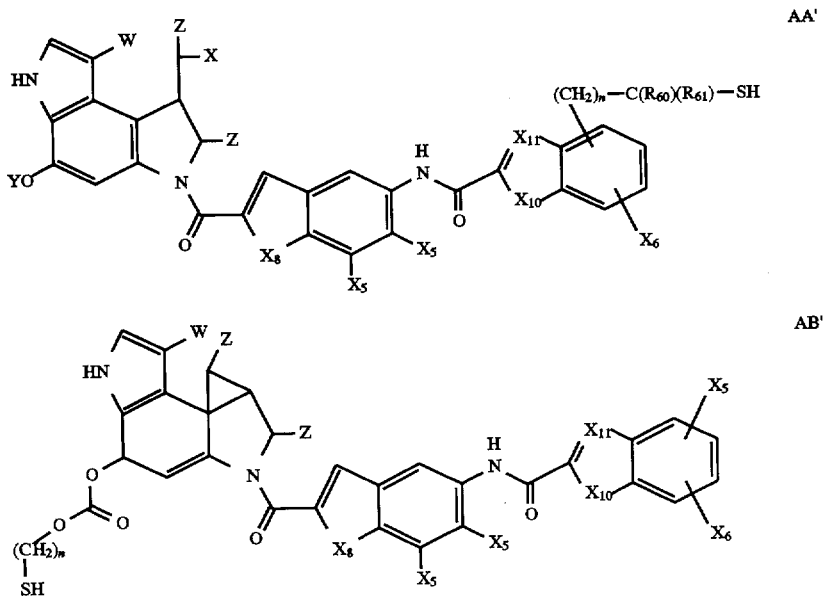

CHART 11
Ar-(linker)-S-S-pyridine + HS—Mab ⟶ Ar-(linker)-S-S—Mab
where Ar-(linker)-s-S-pyridine ≡ X', Y' shown below.
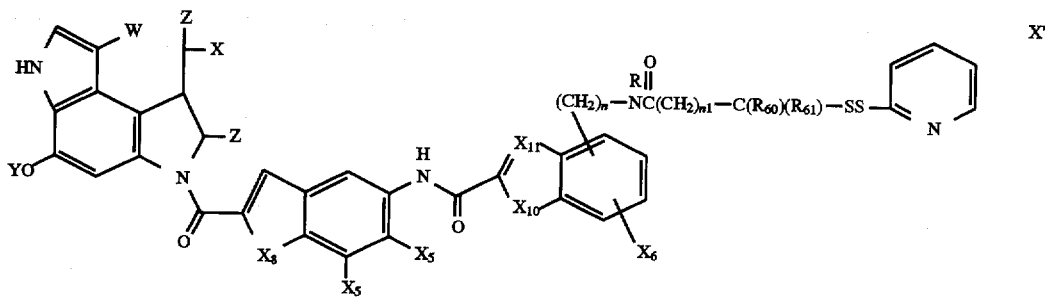
X'
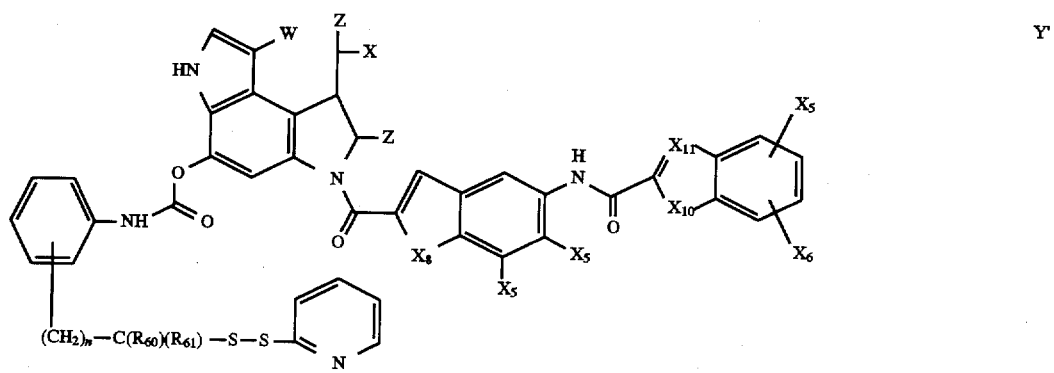
Y'
CHART 12
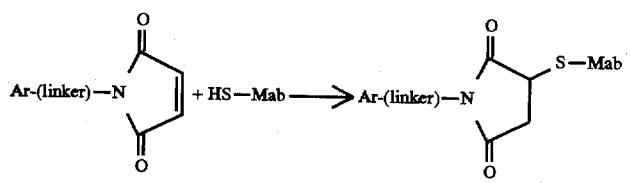
where Ar-(linker)-N ≡ AD', AE' shown below.
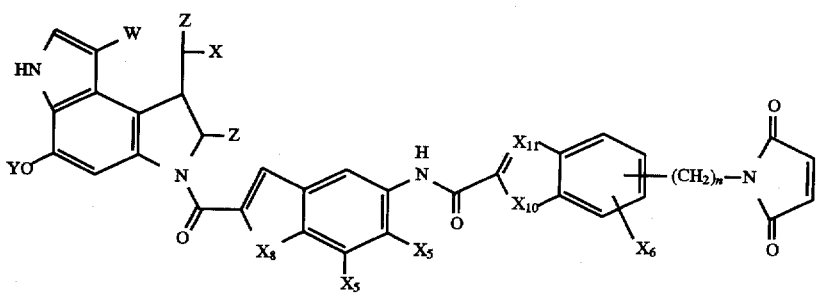
AD'

CHART 12
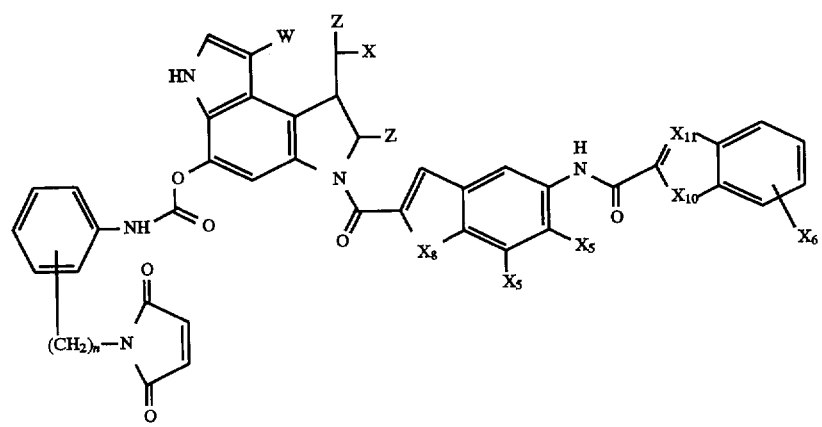
AE'
CHART 13
where Ar-(linker)-C(O)NHNH$_2$ ≡ AG', AH' shown below.
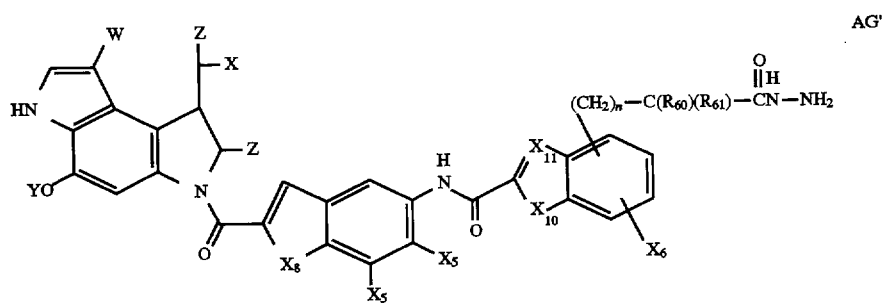
AG'
AH'
CHART 14
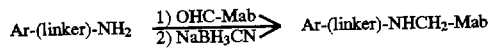
where Ar-(linker)-NH$_2$ ≡ AJ', AK' shown below.

-continued
CHART 14
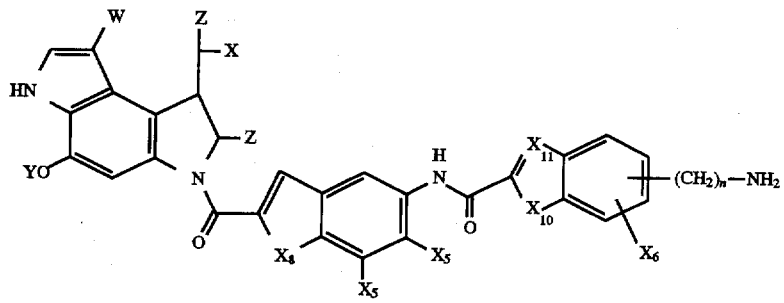
AJ'
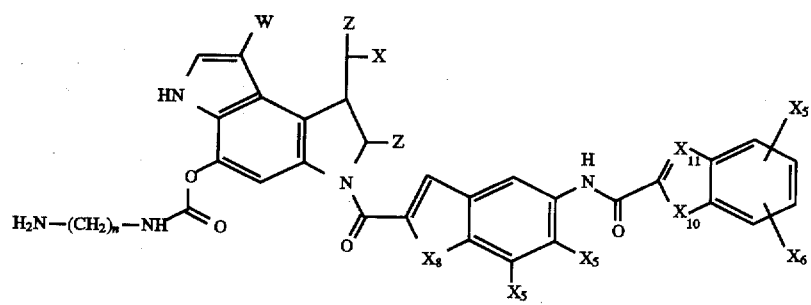
AK'
CHART 15
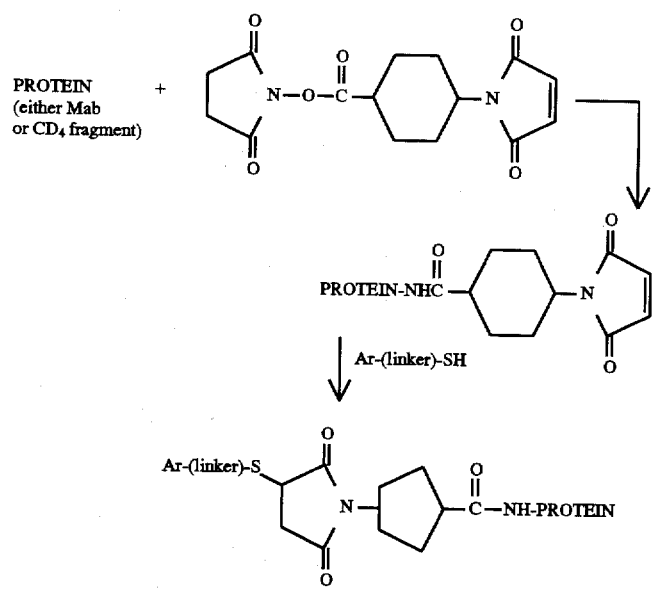
where Ar-(linker)-SH ≡ AA', AC', AF' shown below.
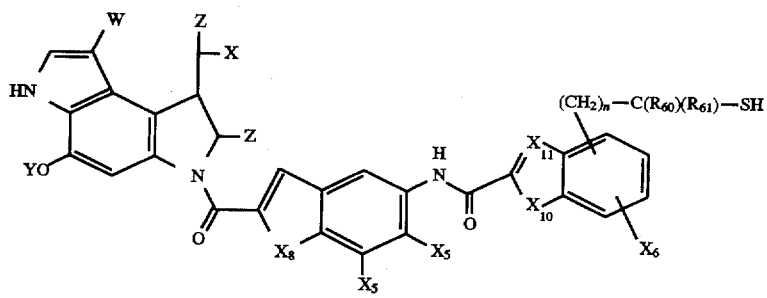
AA'

-continued
CHART 15
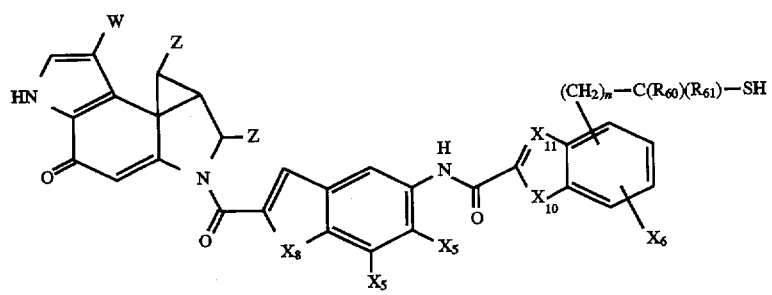
AC'
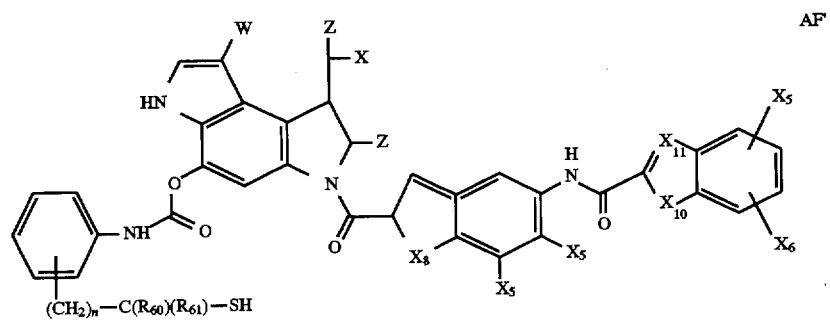
AF'
FORMULA CHART
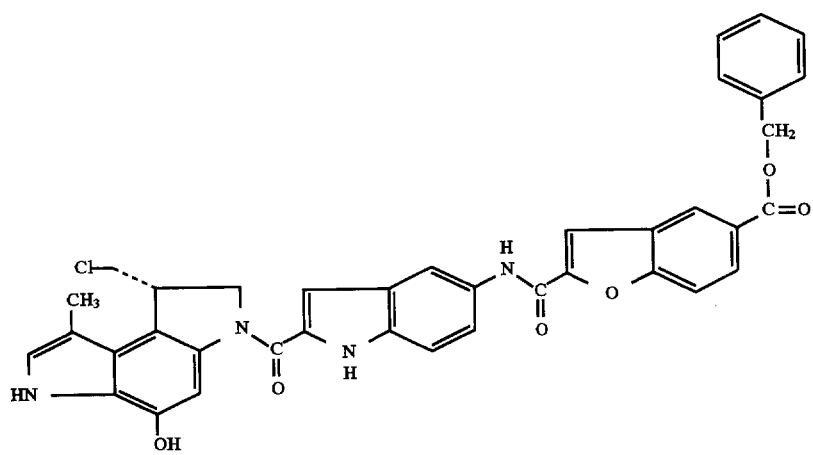
Compound 1
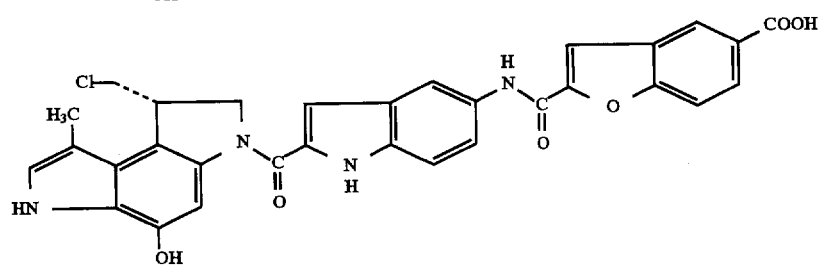
Compound 2
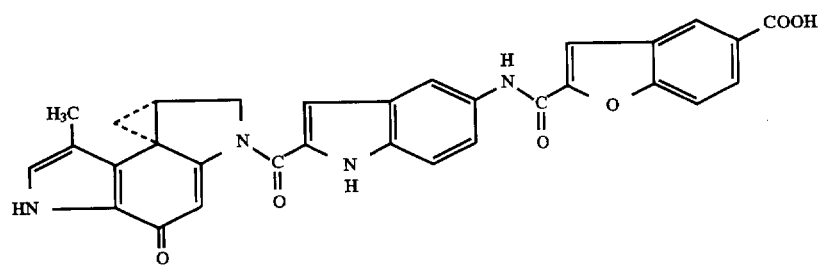
Compound 3

-continued
FORMULA CHART
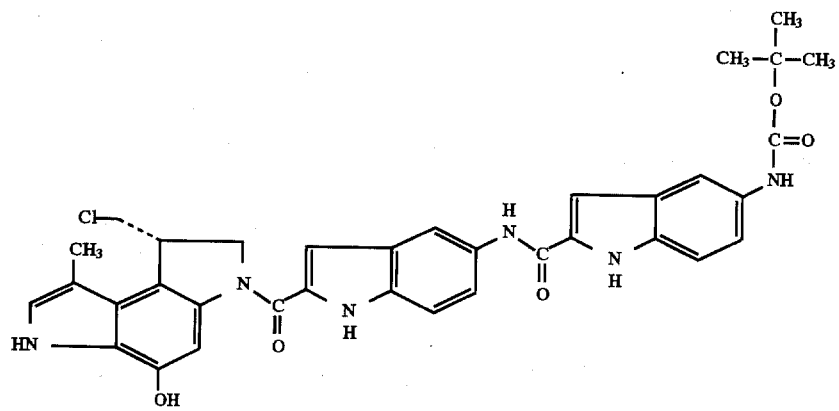
Compound 4
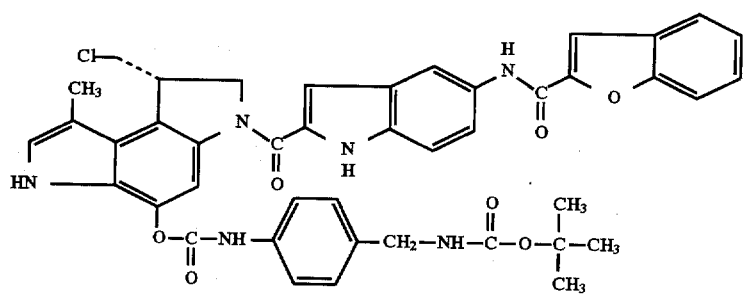
Compound 5
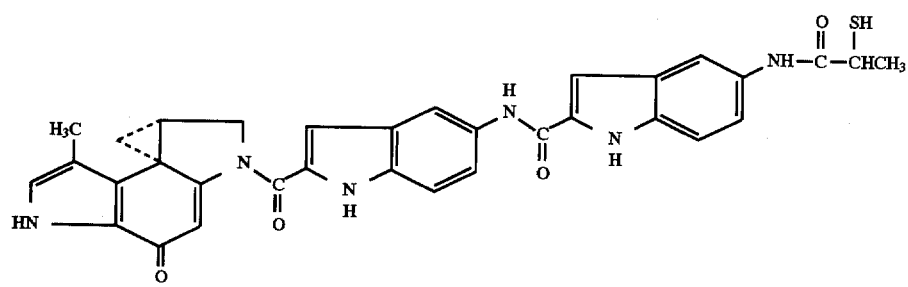
Compound 8
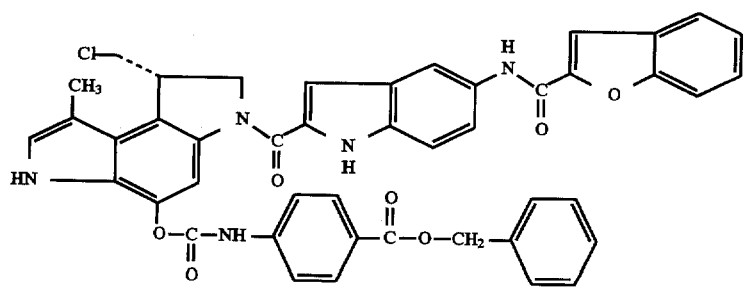
Compound 10
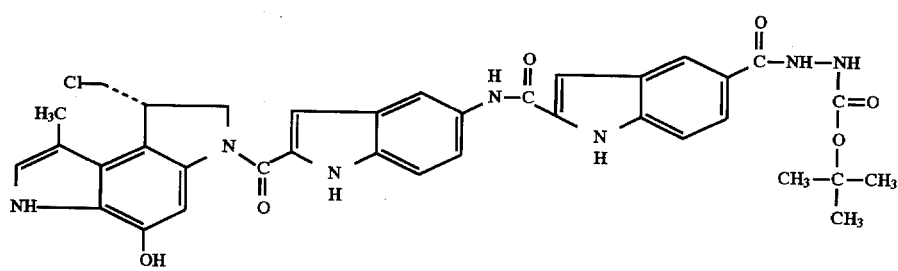
Compound 11A -continued
FORMULA CHART
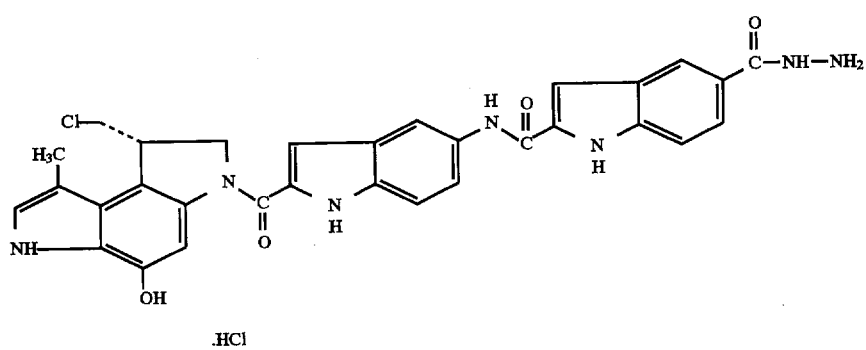
Compound 11B
.HCl
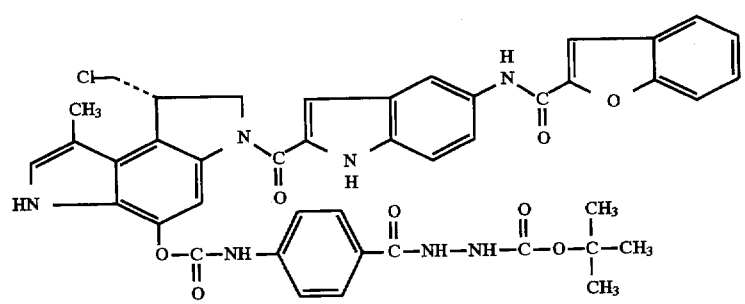
Compound 12
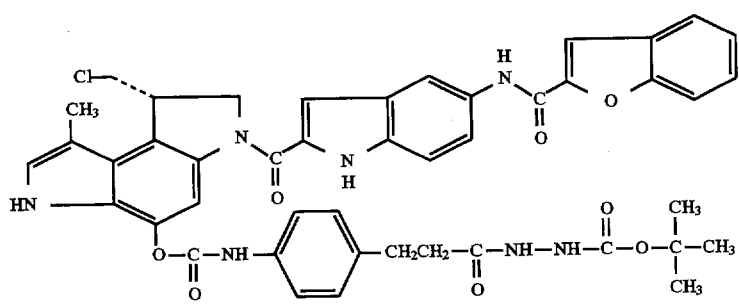
Compound 13
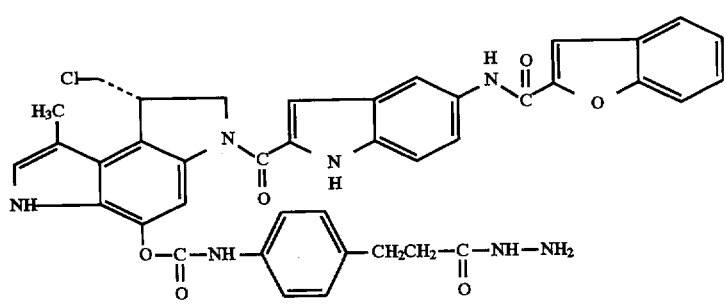
Compound 14
.HCl
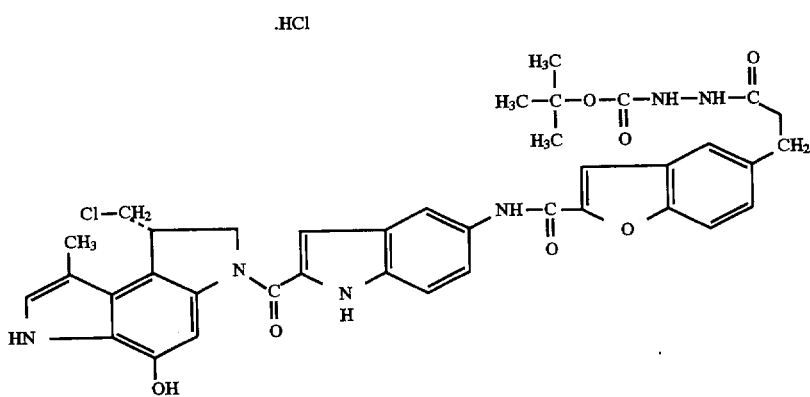
Compound 15

-continued
FORMULA CHART
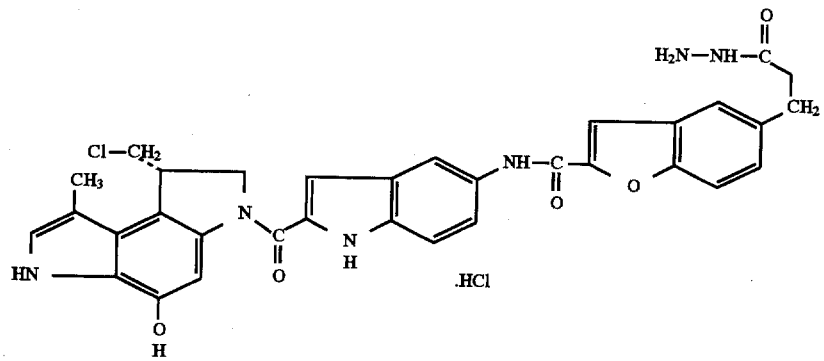
Compound 16
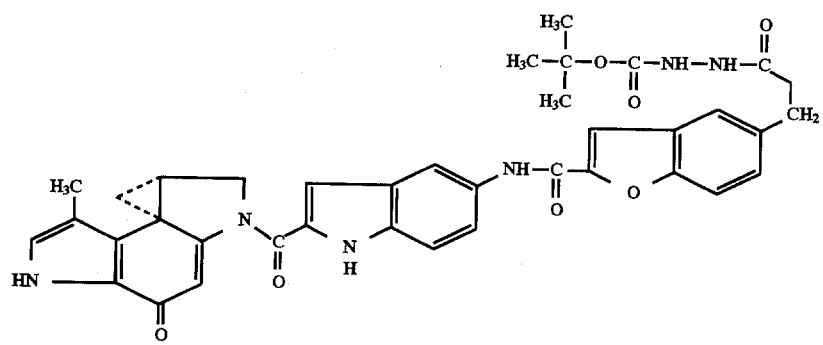
Compound 17
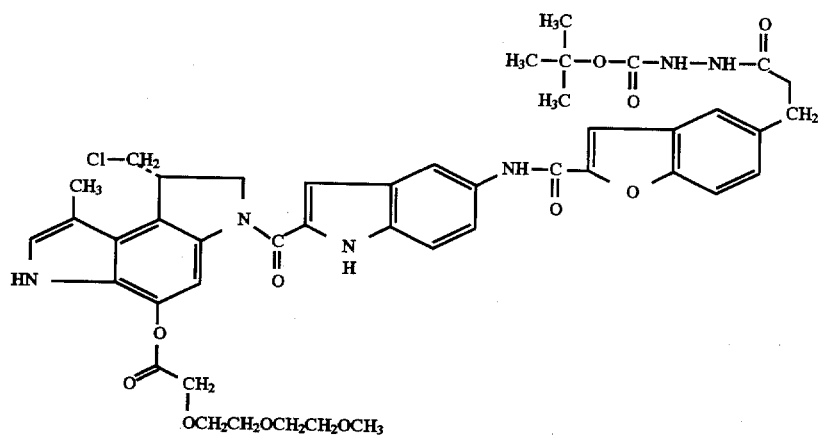
Compound 18
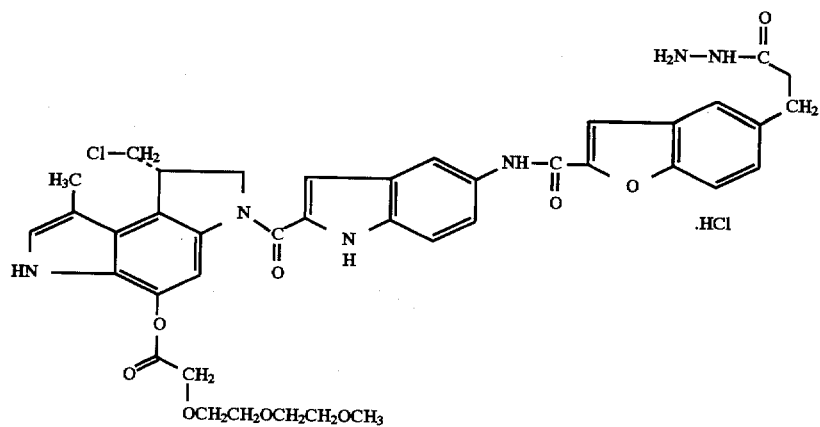
Compound 19

-continued
FORMULA CHART
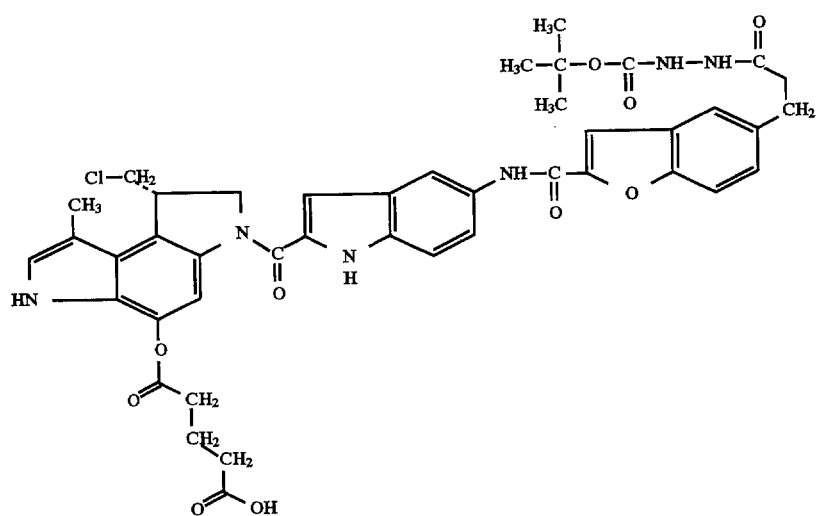
Compound 20
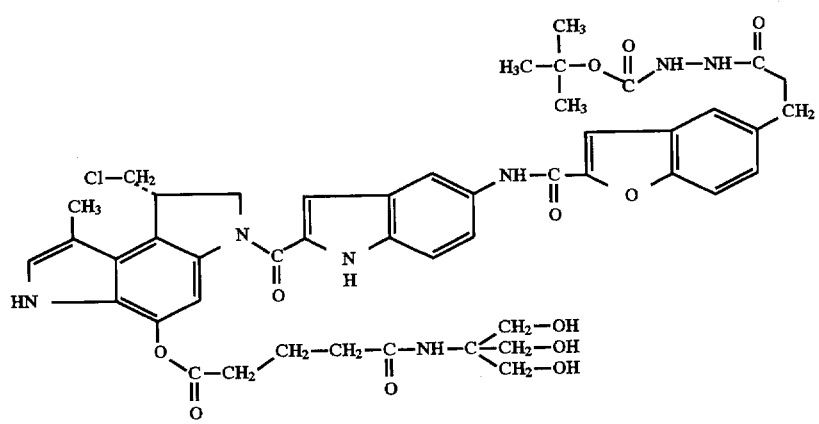
Compound 21
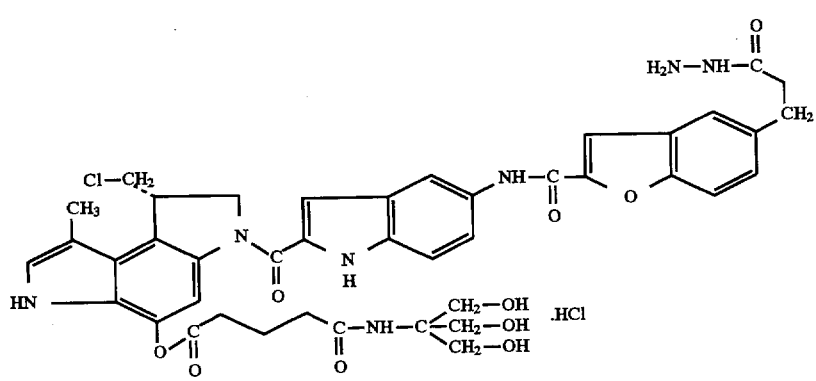
Compound 22

-continued
FORMULA CHART
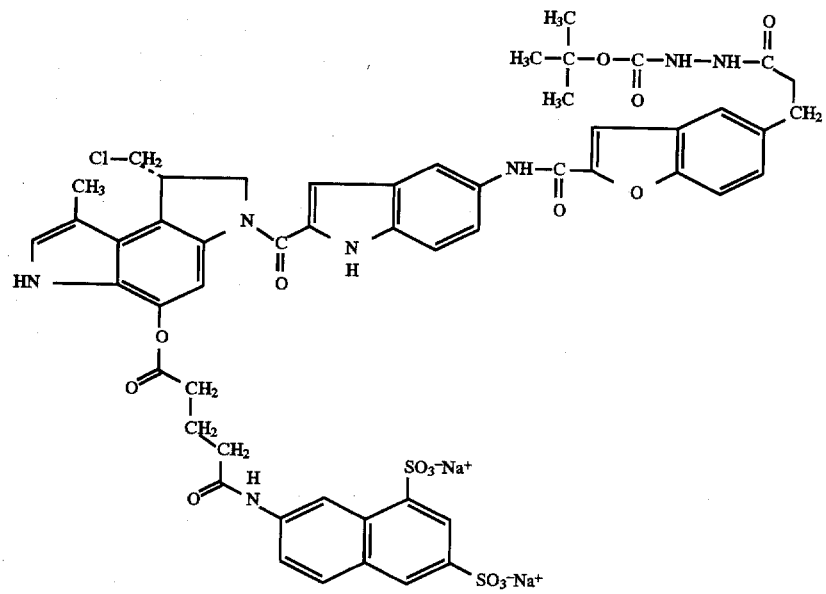
Compound 23
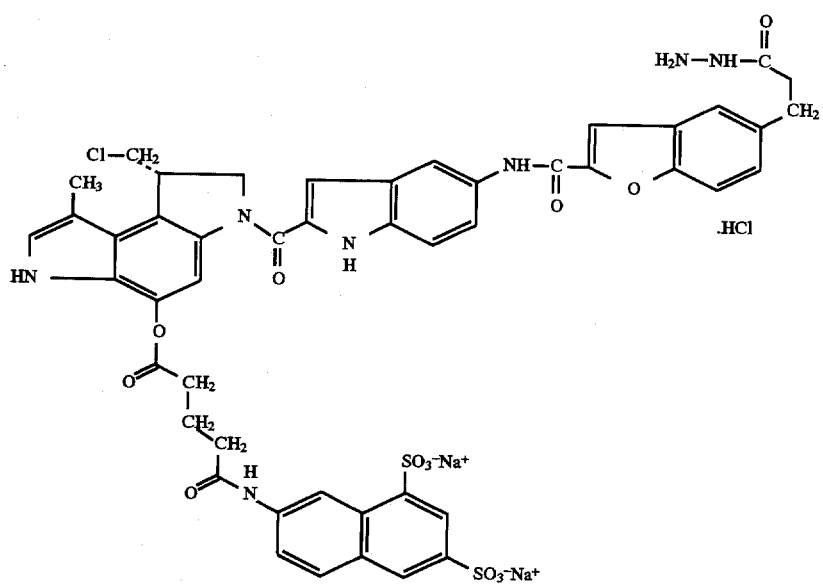
Compound 24
GENERAL FORMULAE CHART
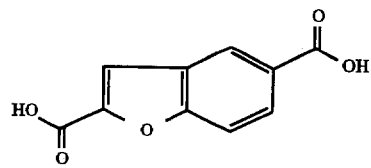
A
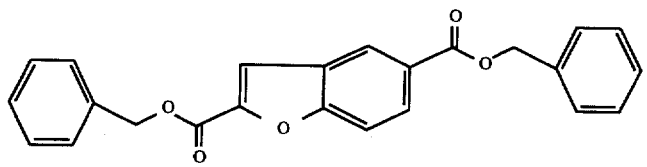
B -continued
GENERAL FORMULAE CHART
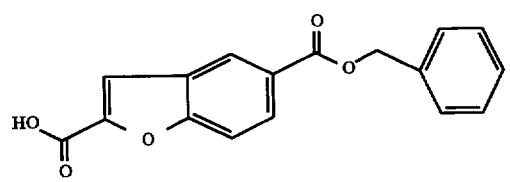 C
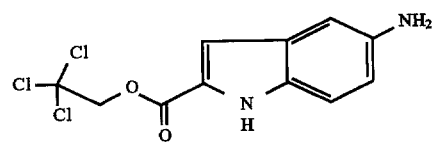 D
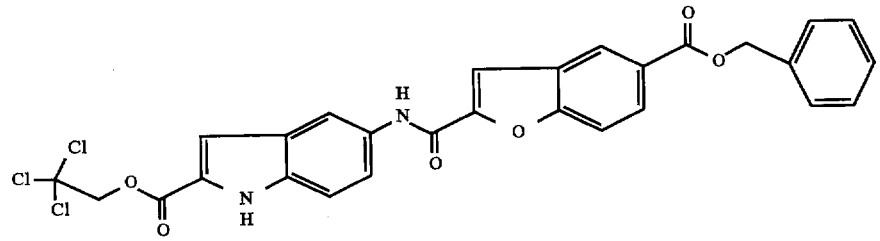 E
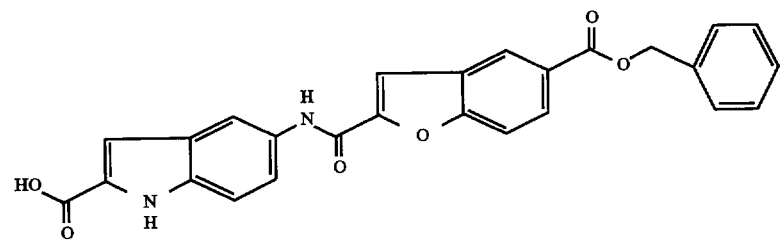 F
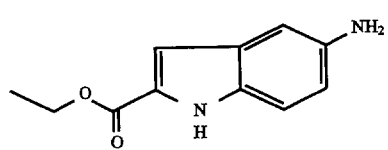 G
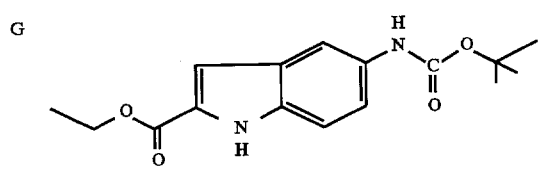 H
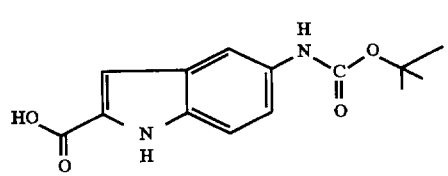 J
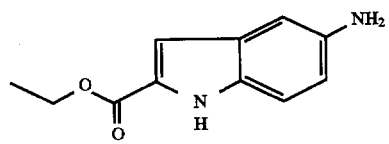 K
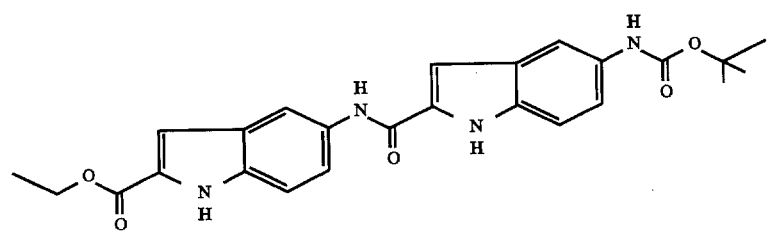 L
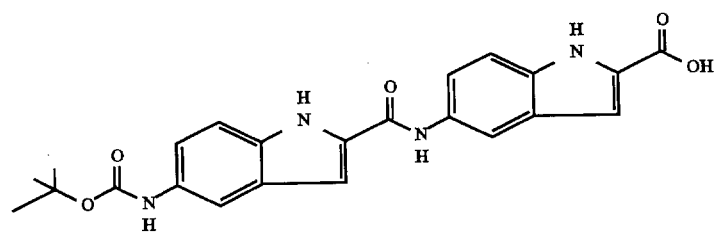 M
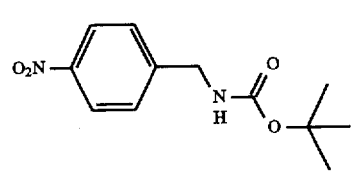 N
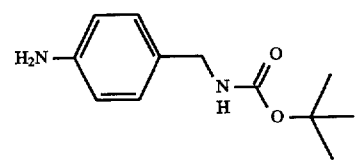 O

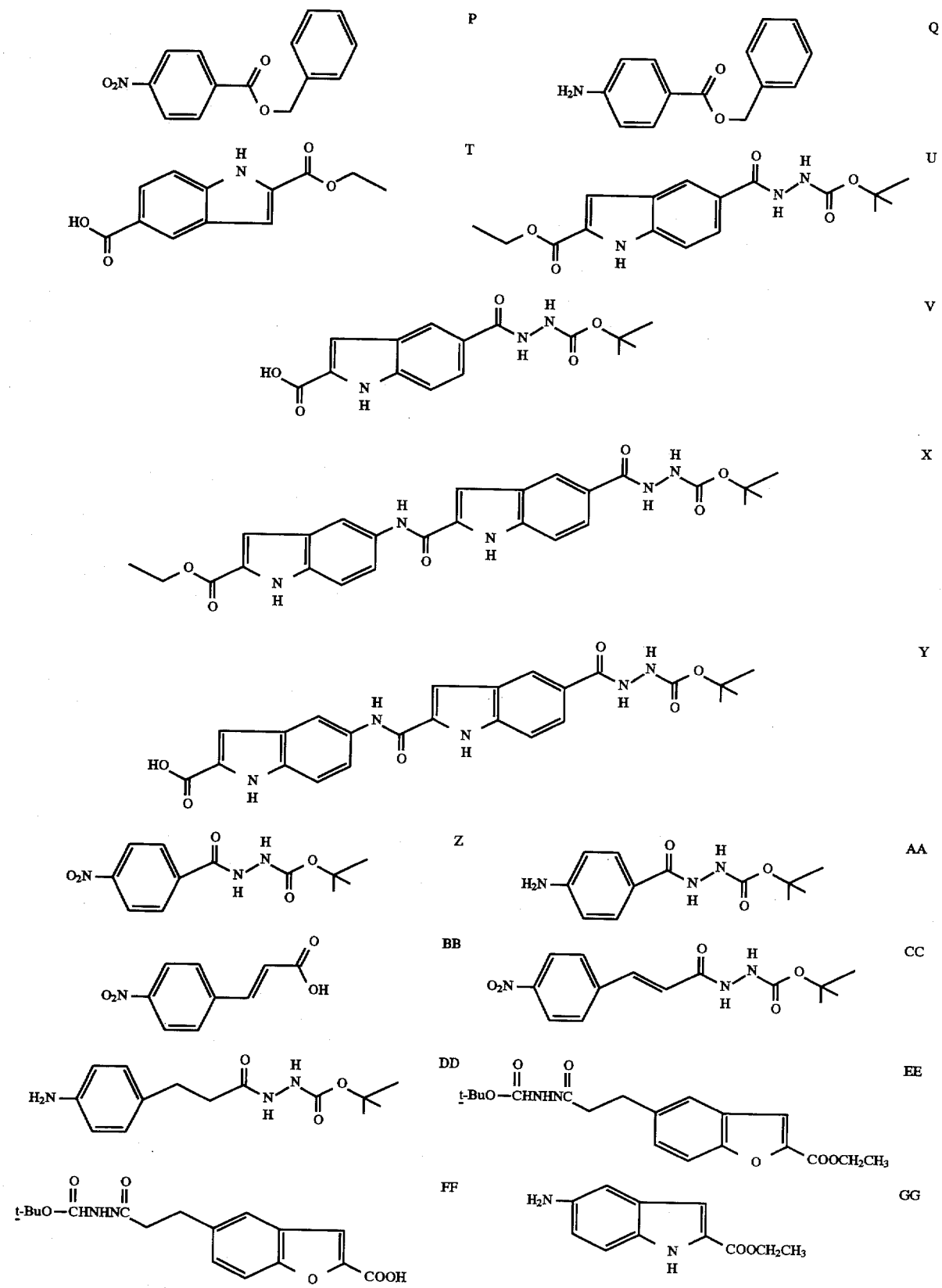

-continued
GENERAL FORMULAE CHART
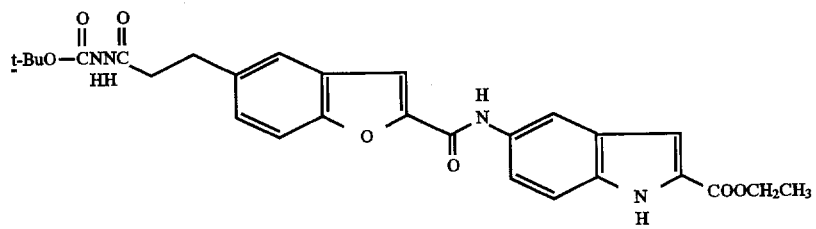
HH
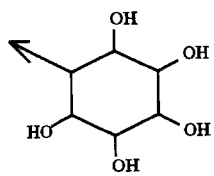
$R_{70}$
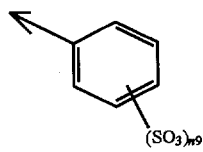
$R_{71}$
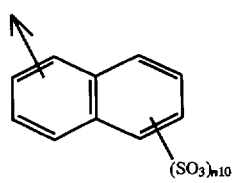
$R_{72}$
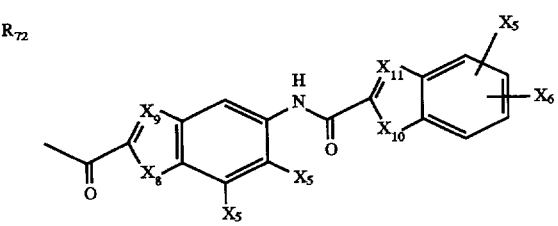
(a)
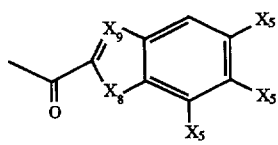
(b)
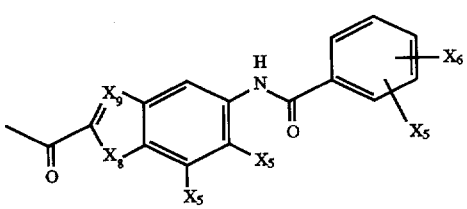
(c)
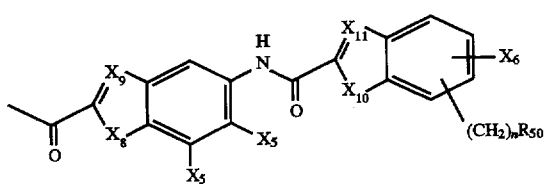
(d)
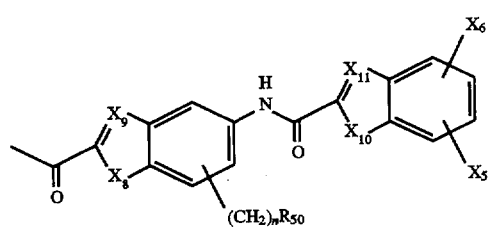
(e)
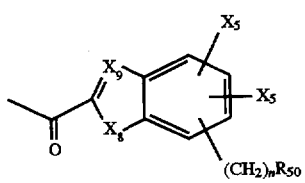
(f)
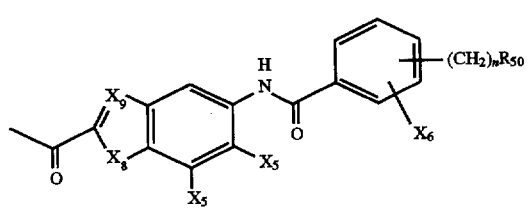
(g)
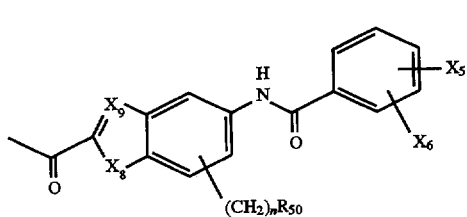
(h)

-continued
GENERAL FORMULAE CHART
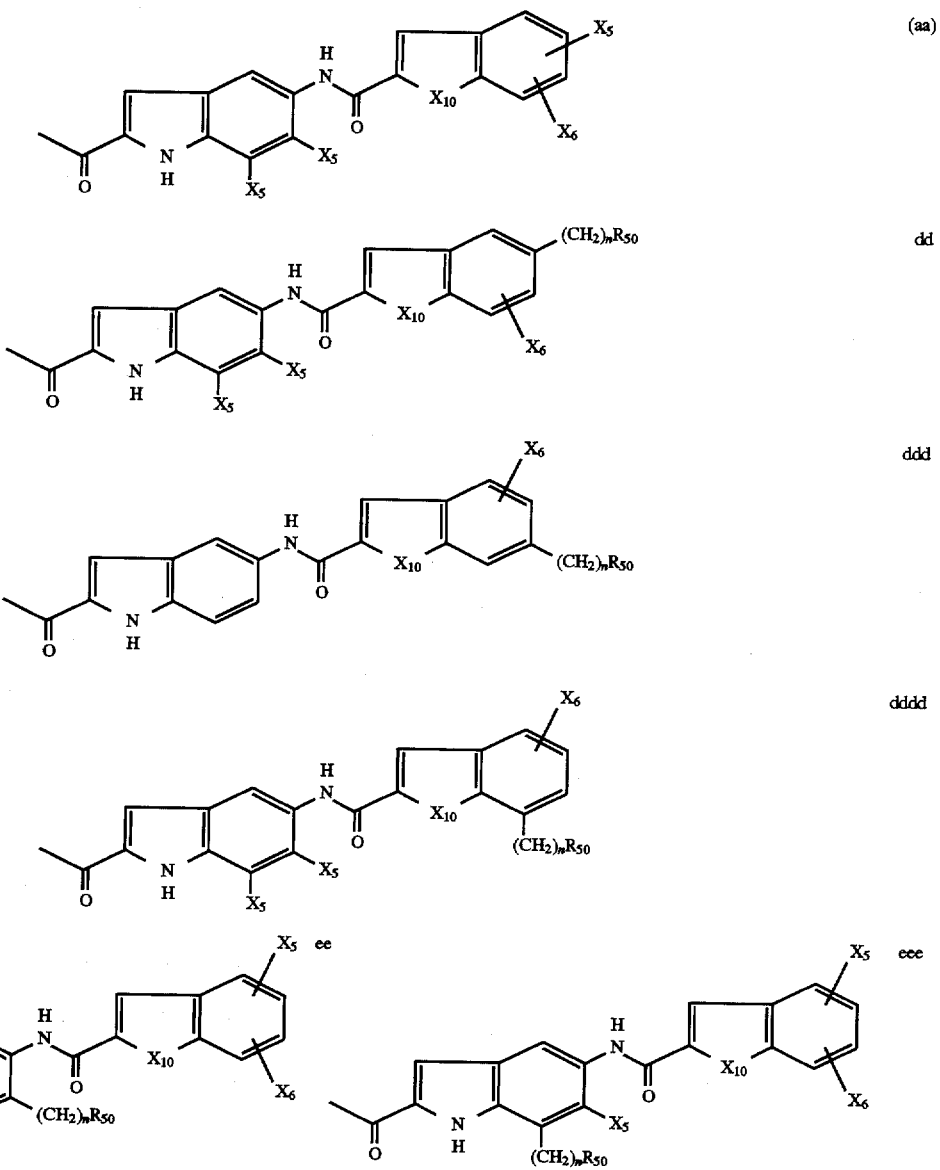
FORMULAE
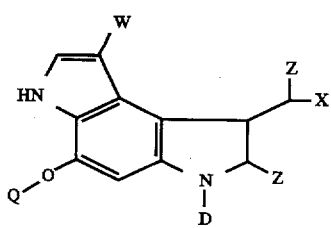
-continued
FORMULAE
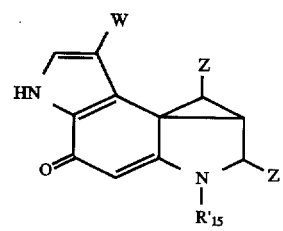

-continued
FORMULAE

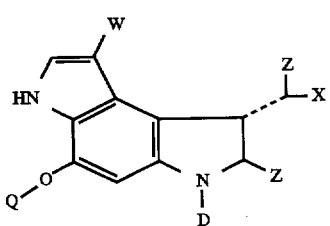

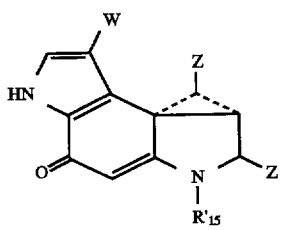

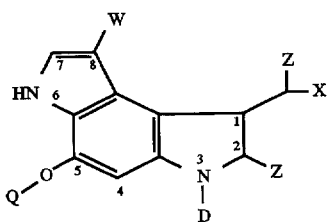

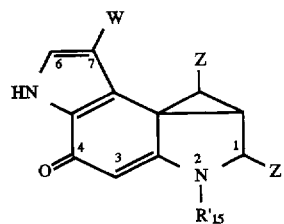

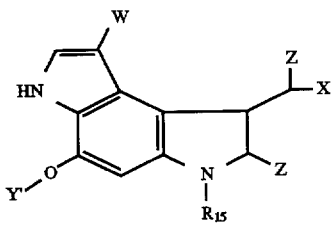

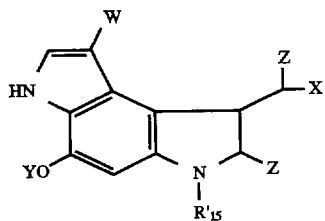

TABLE I

| Compound # | Test | RT Admin. Tumor/Drug | Day of Dosing | Dose ME/KG | T/C |
|---|---|---|---|---|---|
| 11A | L1210 | IP/IV | 1 | 0.20 | 173 |
| 12 | L1210 | IP/IV | 1 | 0.20 | 200 |
| 13 | L1210 | IP/IV | 1 | 0.20 | 213 |
| 15 | L1210 | IP/IV | 1 | 0.20 | 180 |
| 14 | L1210 | IP/IV | 1 | 0.20 | 188 |

TABLE I-continued

| Compound # | Test | RT Admin. Tumor/Drug | Day of Dosing | Dose ME/KG | T/C |
|---|---|---|---|---|---|
| 16 | L1210 | IP/IV | 1 | 0.10 | 181 |
| 18 | L1210 | IP/IV | 1 | 0.20 | 133 |
| 21 | L1210 | IP/IV | 1 | 0.20 | 156 |
| 22 | L1210 | IP/IV | 1 | 0.40 | 172 |

TABLE III

Linker Groups for Attachment of Therapeutic Agents (TA) to Antibody Molecules

A. Linkers for Cleavage by C1

(a.a)$_{n4}$-  —lys—
 —tyr—
 —phe—
 —arg—

B. Tripeptide Sequences for Cleavage by C4,2

(a.a)$_{n4}$-  —leu—ala—arg—
 —leu—ala—lys—
 —leu—ala—tyr—
 —leu—leu—arg—
 —leu—leu—lys—
 —leu—leu—tyr—
 —leu—gly—arg—
 —leu—gly—lys—
 —leu—gly—tyr—
 —leu—val—arg—
 —leu—cal—lys—
 —leu—val—tyr—
 —leu—ile—arg—
 —leu—ile—lys—
 —leu—ile—tyr—

(a.a.)$_{n4}$-  —ala—ala—arg—
 —ala—ala—lys—
 —ala—ala—tyr—
 —ala—leu—arg—
 —ala—leu—lys—
 —ala—leu—tyr—
 —ala—gly—arg—
 —ala—gly—lys—
 —ala—gly—tyr—
 —ala—val—arg—
 —ala—val—lys—

III. B. Tripeptide Sequences for Cleavage by C4,2

—ala—val—tyr—
 —ala—ile—arg—
 —ala—ile—lys—
 —ala—ile—tyr—
 —gly—ala—arg—
 —gly—ala—lys—
 —gly—ala—tyr—
 —gly—leu—arg—
 —gly—leu—lys—
 —gly—gly—arg—
 —gly—gly—lys—
 —gly—gly—tyr—
 —gly—val—arg—
 —gly—val—lys—
 —gly—val—tyr—
 —gly—ile—arg—
 —gly—ile—lys—
 —gly—ile—tyr—

(a.a)$_{n4}$-  —val—ala—arg—
 —val—ala—lys—
 —val—ala—tyr—
 —val—leu—arg—

TABLE III-continued

Linker Groups for Attachment of Therapeutic Agents (TA) to Antibody Molecules —val—leu—lys—
—val—leu—tyr—
—val—gly—arg—
—val—gly—lys—
—val—gly—tyr—
—val—val—arg—
—val—val—lys—
—val—val—tyr—
—val—ile—arg—
—val—ile—lys—
—val—ile—tyr—
—ile—ala—arg—

III. B. Tripeptide Sequences for Cleavage by C4,2

(a.a)$_{n4}$—

—ile—ala—lys—
—ile—ala—tyr—
—ile—leu—arg—
—ile—leu—lys—
—ile—leu—tyr—
—ile—gly—arg—
—ile—gly—lys—
—ile—gly—tyr—
—ile—val—arg—
—ile—val—lys—
—ile—val—tyr—
—ile—ile—arg—
—ile—ile—lys—
—ile—ile—tyr—

III. C. Peptide Sequences for Cleavage by C4, 2

—leu—gly—
—leu—leu—
—leu—ala—
—leu—val—
—leu—ile—
—gly—gly—
—gly—leu—
—gly—ala—
—gly—val—
—ala—gly—           —Tripeptide²
—ala—leu—
—ala—ala—
—ala—val—
—ala—ile—
—val—gly—
—val—leu—
—val—ala—
—val—val—
—val—ile—
—ile—gly—

III. C. Peptide Sequences for Cleavage by C4, 2

—ile—leu—
—ile—ala—
—ile—val—
—ile—ile— wherein (a.a) represents any naturally occurring amino acid (and can be the same or different) and $_{n4}$ = 0–5.

We claim:
1. A compound of Formula I or II:

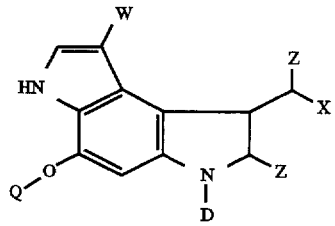

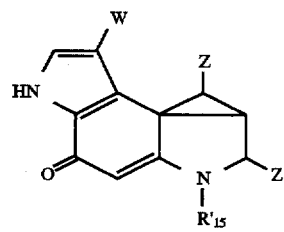

wherein W is selected from $C_1$–$C_5$ alkyl, phenyl or hydrogen;

wherein X is selected from azido, a halogen atom, cyanate, thiocyanate, isocyanate, thioisocyanate, phosphate diester (—PO(OR)$_2$), phosphonyl (—O—PO$_2$R), thiophosphonyl (—O—PSOR), sulfinyl (—O—SOR) or sulfonyl (—O—SO$_2$R);

wherein D is $R_{15}$ or $R'_{15}$;

wherein Q is Y when D is $R'_{15}$;

wherein Q is Y' when D is $R_{15}$;

wherein Y is selected from hydrogen, —C(O)R, —C(S)R, —C(O)OR$_1$, —S(O)$_2$R$_1$, —C(O)NR$_2$R$_3$, —C(S) NR$_2$R$_3$, —C(O)NHSO$_2$R$_4$, —C(O)CH$_2$(OCH$_2$CH$_2$)$_{n7}$ O($C_1$-$C_3$ alkyl) and $_{n7}$ is 0–5, or —C(O)(CH$_2$)$_{n8}$C(O) R$_b$ where $_{n8}$ is 0–10 and R$_b$ is selected from —OH (or a metal or amine salt thereof), —OR$_c$ where R$_c$ is —CH$_2$C(CH$_2$OH)$_3$ or R$_{70}$, and —N(R$_d$) R$_e$ where R$_d$ is hydrogen or $C_1$-$C_4$ alkyl, and R$_e$ is selected from —C(CH$_2$OH)$_3$, —CH$_2$C(CH$_2$OH)$_3$, —CH$_2$C (CH$_2$NH$_2$)$_3$, R$_{70}$, R$_{71}$ or R$_{72}$ where R$_{70}$ is

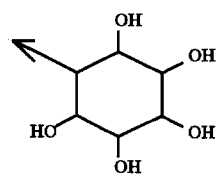

R$_{70}$ where R$_{71}$ is

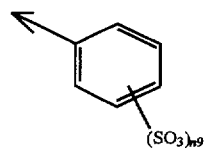

R$_{71}$ where $R_{72}$ is

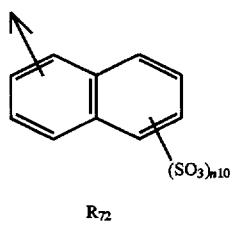

$R_{72}$ where n9 is 1 or 2 and n10 is 1–3;

wherein Y' is selected from —$C(O)R_{10}$, —$C(S)R_{10}$, —$C(O)OR_{10}$, —$S(O)_2R_{10}$, —$C(O)NR_{12}R_{13}$, —$C(S)NR_{12}R_{13}$, or —$C(O)NHSO_2R_{14}$;

wherein Z is selected from the group consisting of $C_1$–$C_5$ alkyl, phenyl or hydrogen;

wherein R is selected from the group consisting of $C_1$–$C_{20}$ alkyl; $C_2$–$C_6$ alkenyl; $C_2$–$C_6$ alkynyl; phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro; naphthyl optionally substituted with one or 2 $C_1$–$C_4$ alkyl, $C_1$–$C_3$ alkoxy, halo, trifluoromethyl, $C_2$–$C_6$ dialkylamino, $C_1$–$C_3$ alkylthio or nitro;

wherein $R_1$ is selected from $C_1$–$C_{20}$ alkyl or phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro;

wherein $R_2$ and $R_3$, being the same or different, are selected from hydrogen, $C_1$–$C_{20}$ alkyl, or phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro; with the proviso that both $R_2$ and $R_3$ cannot be phenyl or substituted phenyl;

wherein $R_4$ is selected from $C_1$–$C_{10}$ alkyl; phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro; naphthyl optionally substituted with one or 2 $C_1$–$C_4$ alkyl, $C_1$–$C_3$ alkoxy, halo, trifluoromethyl, $C_2$–$C_6$ dialkylamino, $C_1$–$C_3$ alkylthio or nitro;

wherein $R_{10}$, $R_{13}$ and $R_{14}$, being the same or different, are selected from —($C_1$–$C_{20}$ alkyl)$(CH_2)_nR_{50}$ or -(phenyl optionally substituted with one or two $C_1$–$C_4$ alkyl, $C_1$–$C_3$ alkoxy, halo, $C_1$–$C_3$ alkylthio, trifluoromethyl, $C_2$–$C_6$ dialkylamino, or nitro)$(CH_2)_nR_{50}$;

wherein n is 0–10;

wherein $R_{50}$ is selected from the group consisting of (i) —$CO_2H$;
(ii) —$CH_2NH_2$;
(iii) —SH;
(iv) —$C(R_{60})(R_{61})$—SH wherein $R_{60}$ and $R_{61}$, being the same or different, are $C_1$–$C_4$ alkyl or H;
(v) —$NHC(O)$—$(CH_2)_{n1}$—$C(R_{60})(R_{61})$—SH wherein $R_{60}$ and $R_{61}$ are defined above and $n_1$ is 0–5;
(vi) —$C(O)NHNH_2$ (hydrazido);
(vii) —$NHNH_2$ (hydrazino);
(viii) —$CH_2OH$ (hydroxymethyl);
(ix) —$NHC(S)NH_2$ (thioureido);
(x) —$CH_2NHC(O)NH_2$;
(xi) —$NHC(S)NHNH_2$;
(xii) —$C(O)CH_2X_1$ ($X_1$ is a halogen);
(xiii) —$CH_2X_1$ (halomethyl) wherein $X_1$ is a halogen;
(xiv) —CHO (aldehyde);
(xvii) —$C(R_{60})(R_{61})C(O)NHNH_2$ wherein $R_{60}$ and $R_{61}$, being the same or different, are $C_1$–$C_4$ alkyl or H;
(xviii) —$O(CH_2)_{n1}C(R_{60})(R_{61})C(O)NHNH_2$ wherein $R_{60}$, $R_{61}$, and $n_1$ are defined above;
(xix) —$N(R_{62})(CH_2)_{n1}C(R_{60})(R_{61})C(O)NHNH_2$ wherein $R_{60}$, $R_{61}$ and $R_{62}$ are independently selected from $C_1$–$C_4$ alkyl or H and $n_1$=–5;
(xx) —$O(CH_2)_{n2}C(R_{60})(R_{61})C(O)NHNH_2$ ($n_2$=1–5);
(xxi) —$NHR_{51}$;
(xxii) —$C(O)NHNHR_{51}$;
(xxiii) —$NHNHR_{51}$;

wherein $R_{51}$ is an amine protecting group such as BOC (t-butoxycarbonyl), FMOC (9-fluorenylmethyloxycarbonyl), TFA (trifluoroacetate)amide), ALLOC (alloxycarbonyl), CBZ (benzoxycarbonyl), or TROC (trichloroethoxycarbonyl);

(xxiv) —$NHC(=NH)NH_2$ (guanadinyl); or
(xxv) —B—M—$(CH_2)_{n3}R_{52}$ wherein $n_3$=0–5; $R_{52}$ is the same as $R_{50}$ above (groups (i)–(xxiv) only);

wherein B is an ester; [—OC(O)— or —C(O)O—] or amide [—NHC(O)— or —C(O)NH—] bond;

wherein M is selected from:

| Linker Groups for Attachment of Therapeutic Agents | |
|---|---|
| | (TA) to Antibody Molecules |
| A. Linkers for Cleavage by C1 | |
| $(a.a)_{n4}$- | —lys— |
| | —tyr— |
| | —phe— |
| | —arg— |
| B. Tripeptide Sequences for Cleavage by C4,2 | |
| | —leu—ala—arg— |
| | —leu—ala—lys— |
| | —leu—ala—tyr— |
| | —leu—leu—arg— |
| | leu—leu—lys— |
| | leu—leu—tyr— |
| | leu—gly—arg— |
| III. B. Tripeptide Sequences for Cleavage by C4,2 | |
| $(a.a)_{n4}$- | —leu—gly—lys— |
| | —leu—gly—tyr— |
| | —leu—val—arg— |
| | —leu—cal—lys— |
| | —leu—val—tyr— |
| | —leu—ile—arg— |
| | —leu—ile—lys— |
| | —leu—ile—tyr— |
| $(a.a.)_{n4}$- | —ala—ala—arg— |
| | —ala—ala—lys— |
| | —ala—ala—tyr— |
| | —ala—leu—arg— |
| | —ala—leu—lys— |
| | —ala—leu—tyr— |
| | —ala—gly—arg— |
| | —ala—gly—lys— |
| | —ala—gly—tyr— |
| | —ala—val—arg— |
| | —ala—val—lys— |
| | —ala—val—tyr— |
| | —ala—ile—arg— |
| | —ala—ile—lys— |
| | —ala—ile—tyr— |
| | —gly—ala—arg— |

| Linker Groups for Attachment of Therapeutic Agents (TA) to Antibody Molecules | |
|---|---|
| | —gly—ala—lys— |
| | —gly—ala—tyr— |
| | —gly—leu—arg— |
| | —gly—leu—lys— |
| | —gly—gly—arg— |
| | —gly—gly—lys— |
| | —gly—gly—tyr— |
| | —gly—val—arg— |
| | —gly—val—lys— |
| | —gly—val—tyr— |
| III. B. Tripeptide Sequences for Cleavage by C4,2 | |
| (a.a)$_{n4}$- | —gly—ile—arg— |
| | —gly—ile—lys— |
| | —gly—ile—tyr— |
| | —val—ala—arg— |
| | —val—ala—lys— |
| | —val—ala—tyr— |
| | —val—leu—arg— |
| | —val—leu—lys— |
| | —val—leu—tyr— |
| | —val—gly—arg— |
| | —val—gly—lys— |
| | —val—gly—tyr— |
| | —val—val—arg— |
| | —val—val—lys— |
| | —val—val—tyr— |
| | —val—ile—arg— |
| | —val—ile—lys— |
| | —val—ile—tyr— |
| (a.a)$_{n4}$- | —ile—ala—arg— |
| | —ile—ala—lys— |
| | —ile—ala—tyr— |
| | —ile—leu—arg— |
| | —ile—leu—lys— |
| | —ile—leu—tyr— |
| | —ile—gly—arg— |
| | —ile—gly—lys— |
| | —ile—gly—tyr— |
| | —ile—val—arg— |
| | —ile—val—lys— |
| | —ile—val—tyr— |
| | —ile—ile—arg— |
| | —ile—ile—lys— |
| | —ile—ile—tyr— |
| III. C. Peptide Sequences for Cleavage by C4,2 | |
| | —leu—gly— |
| | —leu—leu— |
| | —leu—ala— |
| | —leu—val— |
| | —leu—ile— |
| | —gly—gly— |
| | —gly—leu— |
| | —gly—ala— |
| | —gly—val— |
| | —ala—gly— —Tripeptide² |
| | —ala—leu— |
| | —ala—ala— |
| | —ala—val— |
| | —ala—ile— |
| | —val—gly— |
| | —val—leu— |
| | —val—ala— |
| | —val—val— |
| | —val—ile— |
| | —ile—gly— |
| | —ile—leu— |
| | —ile—ala— |
| | —ile—val— |
| | —ile—ile— | wherein (a.a) represents any naturally occurring amino acid (and can be the same or different), tripeptide is any peptide of Section III.B and $n_4=0-5$;

wherein $R_{12}$ is selected from hydrogen, $C_1$–$C_{20}$ alkyl, or phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro;

wherein $R_{15}$ is a carbonylaryl group selected from the group consisting of

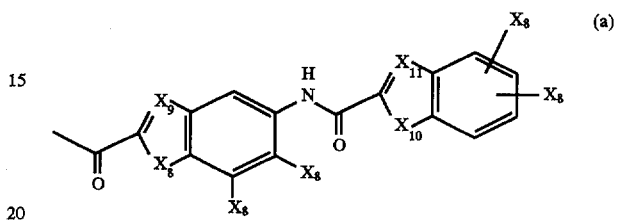

(a)

wherein $X_8$ is —O—, —S—, —NH—; $X_9$ is —CH— or N; $X_{10}$ is —O—, —S—, —NH—; $X_{11}$ is —CH— or —N—; $X_5$ may be the same or different and is H, $OCH_3$, $NO_2$, $NHC(O)CH_3$, OH, halo, $C_1$–$C_4$ alkyl, $C_1$–$C_3$ alkoxy, $C_2$–$C_6$ dialkylamino, or $NHC(O)C_6H_5$; and $X_6$ is H, $OCH_3$, $NO_2$, $NHC(O)CH_3$, OH, halo, $C_1$–$C_4$ alkyl, $C_1$–$C_3$ alkoxy, $C_2$–$C_6$ dialkylamino, or $NHC(O)C_6H_5$;

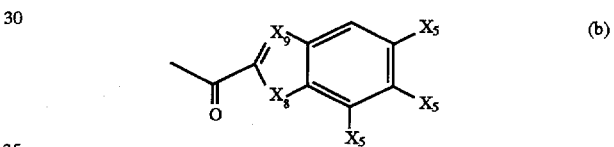

(b)

wherein $X_5$, $X_8$, $X_9$ have the meanings defined above;

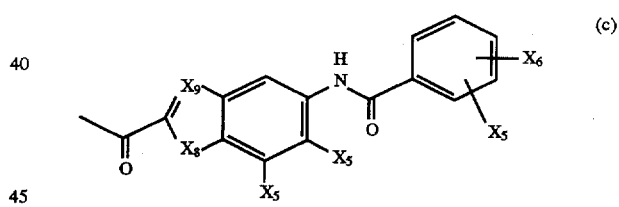

(c)

wherein $X_5$, $X_6$, $X_8$, $X_9$ have the meanings defined above;

wherein $R'_{15}$ is a carbonylaryl group selected from the group consisting of

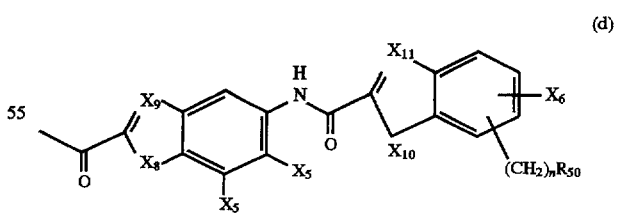

(d)

wherein 8 is —O—, —S—, —NH—; $X_9$ is —CH— or N; $X_{10}$ is —O—, —S—, —NH—; $X_{11}$ is —C— or —N—; $X_5$ is the same or different and is H, $OCH_3$, $NO_2$, $NHC(O)CH_3$, OH, halo, $C_1$–$C_4$ alkyl, $C_1$–$C_3$ alkoxy, $C_2$–$C_6$ dialkylamino, or $NHC(O)C_6H_5$; $X_6$ is H, $OCH_3$, $NO_2$, $NHC(O)CH_3$, OH, halo, $C_1$–$C_4$ alkyl, $C_1$–$C_3$ alkoxy, $C_2$–$C_6$ dialkylamino, or $NHC(O)C_6H_5$; n and $R_{50}$ have the meanings defined above;

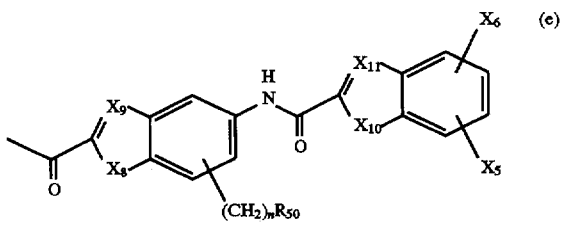
(e)

wherein $X_8$ is —O—, —S—, —NH—; $X_9$ is —CH— or N; $X_{10}$ is —O—, —S—, —NH—; $X_{11}$ is —CH— or —N—; $X_5$ is H, OCH$_3$, NO$_2$, NHC(O)CH$_3$, OH, halo, C$_1$–C$_4$ alkyl, C$_1$–C$_3$ alkoxy, C$_2$–C$_6$ dialkylamino, or NHC(O)C$_6$H$_5$; $X_6$ is H, OCH$_3$, NO$_2$, NHC(O)CH$_3$, OH, halo, C$_1$–C$_4$ alkyl, C$_1$–C$_3$ alkoxy, C$_2$–C$_6$ dialkylamino, or NHC(O)C$_6$H$_5$; n and R$_{50}$ have the meanings defined above;

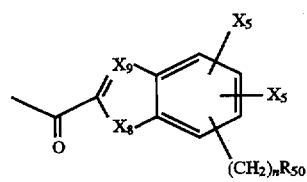
(f)

wherein $X_5$, $X_8$, $X_9$, n and R$_{50}$ have the meanings defined above;

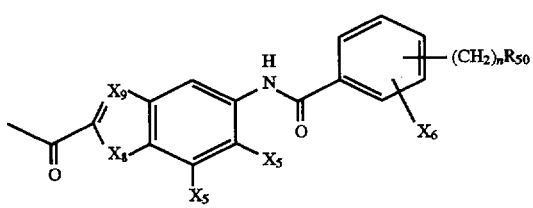
(g)

wherein $X_5$, $X_6$, $X_8$, $X_9$, n and R$_{50}$ have the meanings defined above;

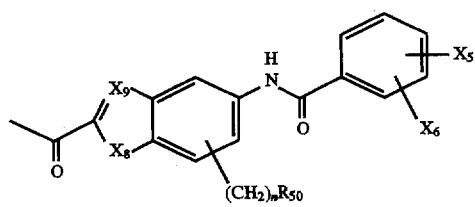
(h)

wherein $X_5$, $X_6$, $X_8$, $X_9$ n and R$_{50}$ have the meanings defined above.

2. A compound of Formula I according to claim 1 wherein W is methyl; Z is hydrogen; X is halogen; and Q is Y' and Y' is selected from —C(O)R$_{10}$, —SO$_2$R$_{10}$, —C(O)NR$_{12}$R$_{13}$; R$_{10}$ and R$_{13}$ are selected from —(phenyl optionally substituted one or two C$_1$–C$_4$ alkyl, C$_1$–C$_3$ alkoxy, halo, C$_1$–C$_3$ alkylthio, trifluoromethyl, C$_2$–C$_6$ dialkylamino, or nitro) (CH$_2$)$_n$R$_{50}$ wherein n is zero, one or two, and R$_{50}$ is —CO$_2$H, —CH$_2$NH$_2$, —SH, —C(R$_{60}$)(R$_{61}$)SH, —NHC(O) —(CH$_2$)$_{n1}$—C(R$_{60}$)(R$_{61}$)—SH, —C(O)NHNH$_2$, —CH$_2$OH, —C(R$_{60}$)(R$_{61}$)C(O)NHNH$_2$, —N(R$_{62}$)(CH$_2$)$_{n1}$ C(R$_{60}$)(R$_{61}$)C(O)—NHNH$_2$, —O(CH$_2$)n$_2$C(R$_{60}$)(R$_{61}$)C(O) NHNH$_2$; wherein n$_1$ is 1–3; n$_2$ is 0–2; R$_{60}$, R$_{61}$ and R$_{62}$, being the same or different, are H, methyl or ethyl; R$_{12}$ is hydrogen; and R$_{15}$ is (aa)

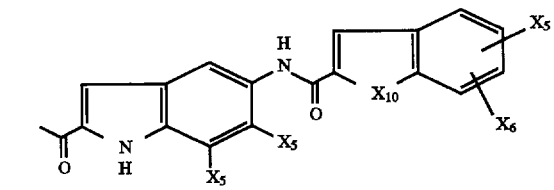

wherein $X_{10}$ is —NH— or —O—; $X_5$ and $X_6$, being the same or different, are hydrogen, OH, NO$_2$NHC(O)CH$_3$, halo, C$_1$–C$_4$ alkyl, C$_1$–C$_3$ alkoxy or C$_2$–C$_6$ dialkylamino.

3. A compound of Formula I according to claim 1 wherein W is methyl; Z is hydrogen; X is halogen; and Q is Y' and Y' is selected from —C(O)R$_{10}$, —SO$_2$R$_{10}$, —C(O)NR$_{12}$R$_{13}$; R$_{10}$ and R$_{13}$ are selected from -(phenyl optionally substituted one or two C$_1$–C$_4$ alkyl, C$_1$–C$_3$ alkoxy, halo, C$_1$–C$_3$ alkylthio, trifluoromethyl, C$_2$–C$_6$ dialkylamino, or nitro) (CH$_2$)$_n$R$_{50}$ wherein n is zero, one or two, and R$_{50}$ is N-hydroxysuccimidyl or maleimide; R$_{12}$ is hydrogen; and R$_{15}$ is (aa)

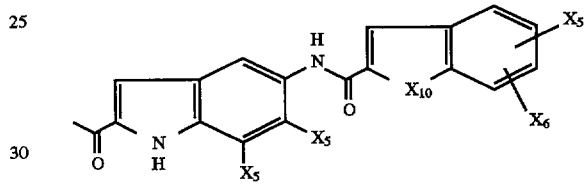

wherein $X_{10}$ is —NH— or —O—; $X_5$ and $X_6$, being the same or different, are hydrogen, OH, NO$_2$, NHC(O)CH$_3$, halo, C$_1$–C$_4$ alkyl, C$_1$–C$_3$ alkoxy or C$_2$–C$_6$ dialkylamino.

4. A compound of Formula I according to claim 1 wherein W is methyl; Z is hydrogen; X is halogen; and Q is Y' and Y' is selected from —C(O)NR$_{12}$R$_{13}$, —C(O)R$_{10}$, —SO$_2$R$_{10}$, —C(O)NR$_{12}$R$_{13}$; R$_{12}$ is hydrogen, R$_{10}$ and R$_{13}$ are selected from -(phenyl optionally substituted with one or two C$_1$–C$_4$ alkyl, C$_1$–C$_3$ alkoxy, halo, C$_1$–C$_3$ alkylthio, trifluoromethyl, C$_2$–C$_6$ dialkylamino, or nitro)(CH$_2$)$_n$R$_{50}$; n is zero or one; R$_{50}$ is —B—M—(CH$_2$)n$_3$R$_{52}$ wherein R$_{52}$ is —NH$_2$, —C(O)NHNH$_2$, —CO$_2$H, or —SH and R$_{15}$ is (aa)

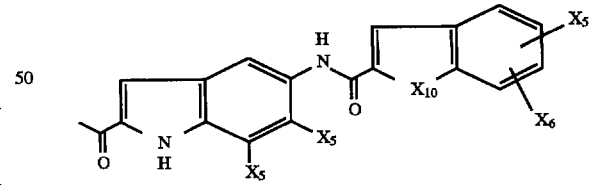

wherein $X_{10}$ is —NH— or —O—; $X_5$ and $X_6$ are independently H, NO$_2$, NHC(O)CH$_3$, halogen, C$_1$–C$_4$ alkyl, C$_1$–C$_3$ alkoxy, or C$_2$–C$_6$ dialkylamino.

5. A compound of Formula I according to claim 1 wherein W is methyl; Z is hydrogen; X is halogen; and Q is Y and Y is selected from hydrogen, —C(O)R, —SO$_2$R$_1$, —C(O) NR$_2$R$_3$; R$_3$ is hydrogen, R and R$_1$ and R$_2$ (being the same or different) are selected from phenyl optionally substituted with one to three C$_1$–C$_4$, alkyl, C$_1$–C$_3$ alkoxy, halo, C$_1$–C$_3$, alkylthio, trifluoromethyl, C$_2$–C$_6$ dialkylamino, or nitro; and R'$_{15}$ is selected from

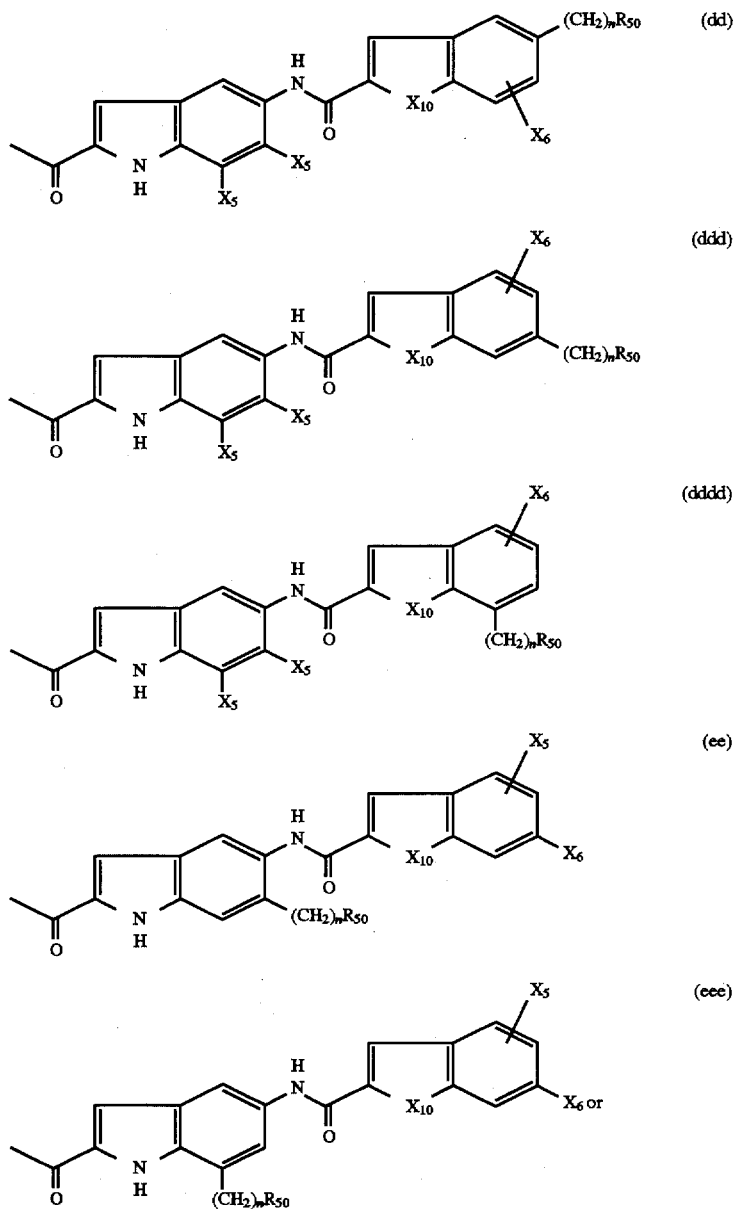

and n is 0–6; $X_{10}$ is —NH— or —O—; $X_5$ and $X_6$ are independently H, OH, $NO_2$, $NHC(O)CH_3$, halo, $C_1$–$C_4$ alkyl, $C_1$–$C_3$ alkoxy or $C_2$–$C_6$ dialkylamino.

6. A compound according to claim 5 wherein $R_{50}$ is N-hydroxysuccimidyl or maleimidyl.

7. A compound according to claim 5 wherein $R_{50}$ is —B—M—$(CH_2)_{n3}R_{52}$ wherein $R_{52}$ is —$NH_2$, —$C(O)NHNH_2$, —$CO_2H$, or —SH.

8. A compound according to claim 5 wherein $R_{50}$ is —$CO_2H$, —$CH_2NH_2$, —SH, —$C(R_{60})(R_{61})SH$, —$NHC(O)(CH_2)_{n1}$—$C(R_{60})(R_{61})$—SH, —$C(O)NHNH_2$, —$CH_2OH$, —$C(R_{60})(R_{61})C(O)NHNH_2$, —$N(R_{62})(CH_2)_{n1}C(R_{60})(R_{61})C(O)$—$NHNH_2$, —$O(CH_2)n_2C(R_{60})(R_{61})C(O)NHNH_2$; wherein n is 1–3; $n_2$ is 0–2; and $R_{60}$, $R_{61}$ and $R_{62}$, being the same or different, are H, methyl or ethyl.

9. A compound according to claim 8 wherein $X_5$ and $X_6$ are both hydrogen.

10. A compound according to claim 2 wherein $X_5$ and $X_6$ are both hydrogen.

11. A compound according to claim 5 wherein $X_5$ and $X_6$ are both hydrogen and $R_{50}$ is —$CO_2H$, —$CH_2NH_2$, —SH, —$C(R_{60})(R_{61})SH$, —$NHC(O)$—$(CH_2)_{n1}$—$C(R_{60})(R_{61})$—SH, —$C(O)NHNH_2$, —$CH_2OH$, —$C(R_{60})(R_{61})C(O)NHNH_2$, —$N(R_{62})(CH_2)_{n1}C(R_{60})(R_{61})C(O)$—$NHNH_2$, —$O(CH_2)n_2C(R_{60})(R_{61})C(O)NHNH_2$; wherein $n_1$ is 1–3; $n_2$ is 0–2; and $R_{60}$, $R_{61}$ and $R_{62}$, being the same or different, are H, methyl or ethyl.

12. A compound according to claim 5 wherein $X_5$ and $X_6$ are both hydrogen, and $R'_{15}$ is

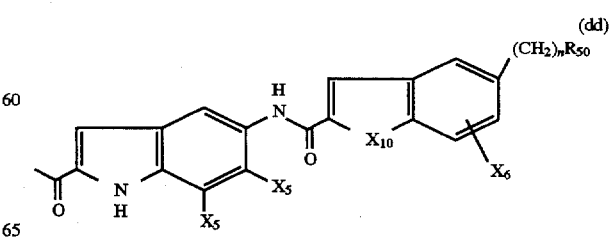

13. A compound according to claim 12 wherein $R_{50}$ is defined as in claim 2.

14. A compound of Formula II according to claim 1 wherein W is methyl; Z is hydrogen; and $R'_{15}$ is selected from

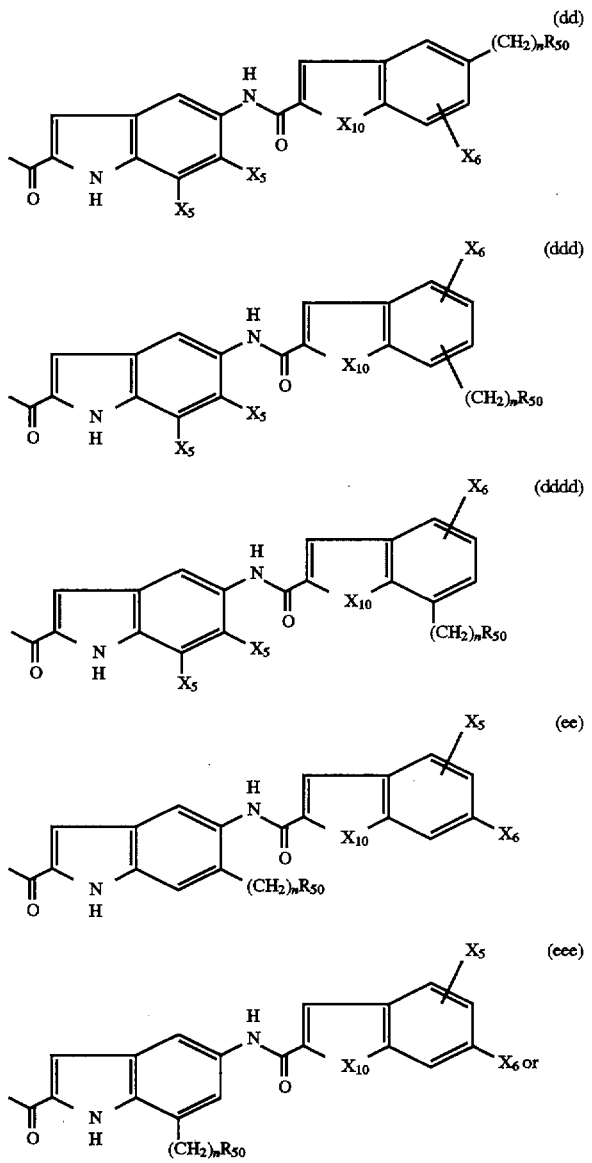

and n is 0–6; $X_{10}$ is —NH— or —O—; and $X_5$ and $X_6$ are independently H, $NO_2$, $NHC(O)CH_3$, halogen, $C_1$–$C_4$ alkyl, $C_1$–$C_3$ alkoxy, or $C_2$–$C_6$ dialkylamino.

15. A compound of Formula II according to claim 14 wherein $R_{50}$ is —$CO_2H$, —$CH_2NH_2$, —SH, —$C(R_{60})(R_{61})$SH, —NHC(O)—$(CH_2)_{n1}$—$C(R_{60})(R_{61})$—SH, —C(O)NHNH$_2$, —$CH_2OH$, —$C(R_{60})(R_{61})C(O)NHNH_2$, —$N(R_{62})(CH_2)_{n1}C(R_{60})(R_{61})C(O)$ —NHNH$_2$, —$O(CH_2)_{n2}C(R_{60})(R_{61})C(O)NHNH_2$; wherein $n_1$ is 1–3; $n_2$ is 0–2; $R_{60}$, $R_{61}$ and $R_{62}$, being the same or different, are H, methyl or ethyl.

16. A compound of Formula II according to claim 14 wherein $X_5$ and $X_6$ are both hydrogen.

17. A compound of Formula II according to claim 14 wherein $X_5$ and $X_6$ are both hydrogen and $R_{50}$ is —$CO_2H$, —$CH_2NH_2$, —SH, —$C(R_{60})(R_{61})$—SH, —NHC(O)—$(CH_2)_{n1}$—$C(R_{60})(R_{61})$—SH, —C(O)NHNH$_2$, —$CH_2OH$, —$C(R_{60})(R_{61})C(O)NHNH_2$, —$N(R_{62})(CH_2)_{n1}C(R_{60})(R_{61})C(O)$—NHNH$_2$, —$O(CH_2)_{n2}C(R_{60})(R_{61})C(O)NHNH_2$; wherein $n_1$ is 1–3; $n_2$ is 0–2; and $R_{60}$, $R_{61}$ and $R_{62}$, being the same or different, are H, methyl or ethyl.

18. A compound of Formula II according to claim 14 wherein $X_5$ and $X_6$ are both hydrogen, and $R'_{15}$ is

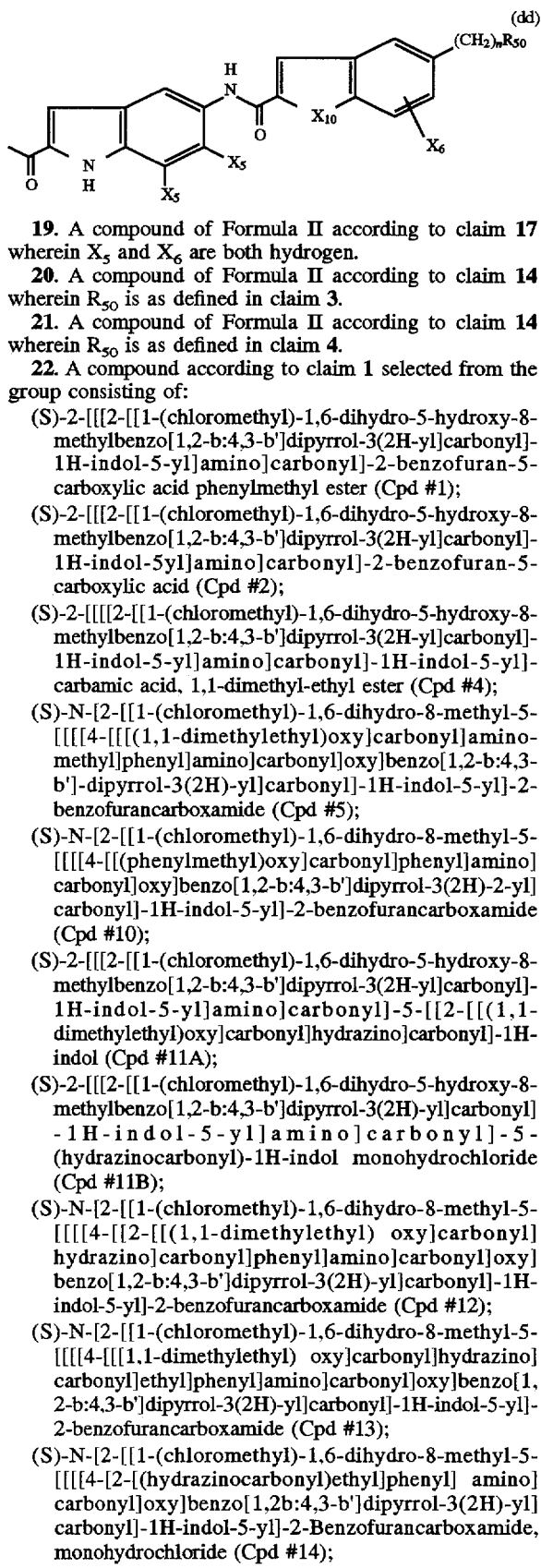

19. A compound of Formula II according to claim 17 wherein $X_5$ and $X_6$ are both hydrogen.

20. A compound of Formula II according to claim 14 wherein $R_{50}$ is as defined in claim 3.

21. A compound of Formula II according to claim 14 wherein $R_{50}$ is as defined in claim 4.

22. A compound according to claim 1 selected from the group consisting of:

(S)-2-[[[2-[[1-(chloromethyl)-1,6-dihydro-5-hydroxy-8-methylbenzo[1,2-b:4,3-b']dipyrrol-3(2H-yl]carbonyl]-1H-indol-5-yl]amino]carbonyl]-2-benzofuran-5-carboxylic acid phenylmethyl ester (Cpd #1);

(S)-2-[[[2-[[1-(chloromethyl)-1,6-dihydro-5-hydroxy-8-methylbenzo[1,2-b:4,3-b']dipyrrol-3(2H-yl]carbonyl]-1H-indol-5yl]amino]carbonyl]-2-benzofuran-5-carboxylic acid (Cpd #2);

(S)-2-[[[[2-[[1-(chloromethyl)-1,6-dihydro-5-hydroxy-8-methylbenzo[1,2-b:4,3-b']dipyrrol-3(2H-yl]carbonyl]-1H-indol-5-yl]amino]carbonyl]-1H-indol-5-yl]-carbamic acid, 1,1-dimethyl-ethyl ester (Cpd #4);

(S)-N-[2-[[1-(chloromethyl)-1,6-dihydro-8-methyl-5-[[[[4-[[[(1,1-dimethylethyl)oxy]carbonyl]amino-methyl]phenyl]amino]carbonyl]oxy]benzo[1,2-b:4,3-b']-dipyrrol-3(2H)-yl]carbonyl]-1H-indol-5-yl]-2-benzofurancarboxamide (Cpd #5);

(S)-N-[2-[[1-(chloromethyl)-1,6-dihydro-8-methyl-5-[[[[4-[[(phenylmethyl)oxy]carbonyl]phenyl]amino] carbonyl]oxy]benzo[1,2-b:4,3-b']dipyrrol-3(2H)-2-yl] carbonyl]-1H-indol-5-yl]-2-benzofurancarboxamide (Cpd #10);

(S)-2-[[[2-[[1-(chloromethyl)-1,6-dihydro-5-hydroxy-8-methylbenzo[1,2-b:4,3-b']dipyrrol-3(2H-yl]carbonyl]-1H-indol-5-yl]amino]carbonyl]-5-[[2-[[(1,1-dimethylethyl)oxy]carbonyl]hydrazino]carbonyl]-1H-indol (Cpd #11A);

(S)-2-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-(hydrazinocarbonyl)-1H-indol monohydrochloride (Cpd #11B);

(S)-N-[2-[[1-(chloromethyl)-1,6-dihydro-8-methyl-5-[[[[4-[[2-[[(1,1-dimethylethyl) oxy]carbonyl] hydrazino]carbonyl]phenyl]amino]carbonyl]oxy] benzo[1,2-b:4,3-b']dipyrrol-3(2H)-yl]carbonyl]-1H-indol-5-yl]-2-benzofurancarboxamide (Cpd #12);

(S)-N-[2-[[1-(chloromethyl)-1,6-dihydro-8-methyl-5-[[[[4-[[[1,1-dimethylethyl) oxy]carbonyl]hydrazino] carbonyl]ethyl]phenyl]amino]carbonyl]oxy]benzo[1,2-b:4,3-b']dipyrrol-3(2H)-yl]carbonyl]-1H-indol-5-yl]-2-benzofurancarboxamide (Cpd #13);

(S)-N-[2-[[1-(chloromethyl)-1,6-dihydro-8-methyl-5-[[[[4-[2-[(hydrazinocarbonyl)ethyl]phenyl] amino] carbonyl]oxy]benzo[1,2b:4,3-b']dipyrrol-3(2H)-yl] carbonyl]-1H-indol-5-yl]-2-Benzofurancarboxamide, monohydrochloride (Cpd #14);

(S)-[[[2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-[[2-[[(1,1-dimethylethyl)oxy]carbonyl]hydrazino]carbonyl]ethyl]-2-Benzofuran (Cpd #15);

(S)-[[[2[[1-(chloromethyl)-1,6-dihydro-5-hydroxy-g-methylbenzo[1,2-b:4,3-b']dipyrrol]-3(2H)-yl]carbonyl]-1H-indol-5-yl]amino]carbonyl-5-2-(hydrazinocarbonyl)ethyl]-2-benzofuran monohydrochloride (Cpd #16);

(S)-[[[-2[[1-(chloromethyl)-1,6-dihydro-5-hydroxy-8-methylbenzo[1,2-b:4,3-b']dipyrrol-3(2H)-yl ]carbonyl]-1H-indol-5-yl]amino]carbonyl]-5-[2-[[2-[[(1,1-dimethylethyl)oxy]hydrazino]ino]carbonyl]ethyl]-2-benzofuran 3,6,9-trioxadecanoic acid ester (Cpd #18);

(S)-[[[-2[[1-(chloromethyl)-1,6-dihydro-5-hydroxy-8-methylbenzo[1,2-b:4,3-b']dipyrrol-3(2H)-yl]carbonyl]1H-indol-5-yl]amino]carbonyl]-5-[2-(hydrazino)carbonyl]ethyl-2-benzfuran 3,6,9-trioxadecanoic acid ester (Cpd #19);

(S)-[[[-2[[1-(chloromethyl)-1,6-dihydro-5-hydroxy-g-methylbenzo[1,2-b:4,3-b']dipyrrol-3(2H)-yl]carbonyl]-1H-indol-5-yl]amino]carbonyl]-5-[2-[[2-[[(1,1-dimethylethyl)oxy]carbonyl]hydrazino]carbonyl]ethyl]-2-benzofuran glutaric acid monoester (Cpd #20);

(S)-[[[-2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-[[2-[[(1,1-dimethylethyl)oxy]carbonyl]hydrazino]carbonyl]ethyl]-2-benzofuran ester of N-[2-hydroxy-1,1-bis(hydroxymethyl)ethyl]glutaramic acid (Cpd #21);

(S)-[[[-2[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2(hydrazino)carbonyl]ethyl-2-benzofuran ester of N-[2hydroxy-1,1-bis(hydroxymethyl)ethyl]glutaramic acid (Cpd #22);

(S)-[[[-2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl]-5-[2-[[2-[[(1,1-dimethylethyl)oxy]carbonyl]hydrazino]carbonyl]ethyl]-2-benzofuran glutaric acid monoester mono amide of 7-amino-naphthalene-1,3-disulfonic acid disodium salt (Cpd #23); or (S)-[[[-2-[[1-(chloromethyl)-1,6-dihydro-5-hydroxy-8-methylbenzo[1,2-b:4,3-b']dipyrrol-3(2H)-yl]carbonyl]-1H-indol-5-yl]amino]carbonyl-5-[2-(hydrazino)carbonylethyl-2-benzofuran glutaric acid monoester mono amide of 7-amino-naphthalene-1,3-disulfonic acid disodium salt (Cpd #24).

23. A compound according to claim 1 selected from the group consisting of:

(S)$_2$-[[[2-[(4,5,8,8a-tetrahydro-7-methyl-4-oxocyclopropa-[c]pyrrol[3,2-e]indol-2(1H)-yl)-carbonyl]-1H-indol-5-yl]amino]carbonyl]-2-benzofuran-5-carboxylic acid (Cpd #3);

5-[(2-mercaptopropionyl)amino]-N-[2-(4,5,8,8a-tetrahydro-7-methyl-4-oxocyclopropa-[c-]pyrrolo[3,2-e]indol-2(1H)-yl)-1H-indol-5-yl]-1H-indole-2-carboxamide (Cpd #8); or (7bR)-N-[2-[[4,5,8,8a-tetrahydro-7-methyl-4-oxocyclopropa[c]pyrrol[3,2-e]indol-2-(1H)-yl-carbonyl]-1H-indol-5-yl]aminocarbonyl]-5-[2-[[2-[(1,1-dimethylethyl)-oxy]carbonyl]hydrazino]carbonyl]ethyl-2-benzofuran (Cpd #17).

* * * * *